(12) United States Patent
Larmagnac et al.

(10) Patent No.: US 10,802,297 B2
(45) Date of Patent: Oct. 13, 2020

(54) LENS COMPRISING AN ADJUSTABLE FOCUS LENGTH

(71) Applicant: OPTOTUNE AG, Dietikon (CH)

(72) Inventors: Alexandre Larmagnac, Widen (CH); Matthias Walser, Zurich (CH); Manuel Aschwanden, Allenwinde (CH); Marcel Suter, Zurich (CH); David Niederer, Kuttigen (CH); Anja Stobbe-Kreemers, Mollis (CH); Stephan Smolka, Zurich (CH); Roman Patscheider, Winterthur (CH); Jochen Hotzel, Kreuzlingen (CH)

(73) Assignee: OPTOTUNE AG, Dietikon (CH)

( * ) Notice: Subject to any disclaimer, the term of this patent is extended or adjusted under 35 U.S.C. 154(b) by 0 days.

(21) Appl. No.: 15/766,818

(22) PCT Filed: Oct. 10, 2016

(86) PCT No.: PCT/EP2016/074248
§ 371 (c)(1),
(2) Date: Apr. 8, 2018

(87) PCT Pub. No.: WO2017/060537
PCT Pub. Date: Apr. 13, 2017

(65) Prior Publication Data
US 2018/0217402 A1 Aug. 2, 2018

(30) Foreign Application Priority Data

Oct. 8, 2015 (EP) .................................... 15188979
Apr. 28, 2016 (WO) ................. PCT/EP2016/059572

(51) Int. Cl.
*G02C 7/02* (2006.01)
*G02C 7/04* (2006.01)
(Continued)

(52) U.S. Cl.
CPC ............ *G02C 7/049* (2013.01); *A61F 2/1635* (2013.01); *G02B 3/14* (2013.01); *G02C 7/041* (2013.01); *G02C 7/085* (2013.01)

(58) Field of Classification Search
CPC ........ G02C 7/049; G02C 7/041; G02C 7/085; G02C 7/04; G02C 7/042; G02C 7/081;
(Continued)

(56) References Cited

U.S. PATENT DOCUMENTS

| 4,816,031 A | 3/1989 | Pfoff |
| 8,422,142 B2 | 4/2013 | Bolis |

(Continued)

FOREIGN PATENT DOCUMENTS

| DE | 102009021702 | 12/2009 |
| WO | 9814820 | 4/1998 |

(Continued)

*Primary Examiner* — William R Alexander
*Assistant Examiner* — Henry A Duong
(74) *Attorney, Agent, or Firm* — JMB Davis Ben-David

(57) ABSTRACT

The invention relates to a lens (1) for vision correction, wherein the lens (1) is particularly configured to be placed directly on the surface of an eye (2) of a person, wherein the lens (1) further comprises: a transparent base element (10) having a back side (12), and a front side (11) facing away from the back side (12), a transparent and elastically expandable membrane (20) connected to said base element (10), wherein said membrane (20) comprises a back side (22) that faces said front side (11) of the base element (10), a ring member (30) connected to said back side (22) of the membrane (20) so that the ring member (30) defines a curvature-adjustable area (23) of the membrane (20), and wherein the lens (1) comprises a lens volume (41) adjacent said curvature-adjustable area (23) of the membrane (20), which lens volume (41) is delimited by the ring member (30), and wherein the lens (1) comprises a reservoir volume (42) arranged in a boundary region (24) of the lens (1), wherein (Continued)

said two volumes (41, 42) are each filled with a transparent liquid (50, 50a, 50b), and a pumping means (700) configured to transfer transparent liquid (50) from the reservoir volume (42) to the lens volume (41) such that the curvature of said curvature-adjustable area (23) of the membrane (22) increases and the focal length of the lens (1) decreases, and optionally a rigid support structure (31) that is configured to reduce or prevent compression of the reservoir volume (42) when an eyelid of the user rests on said boundary region (24) of the lens.

55 Claims, 35 Drawing Sheets

(51) Int. Cl.
*G02C 7/08* (2006.01)
*G02B 3/14* (2006.01)
*A61F 2/16* (2006.01)

(58) Field of Classification Search
CPC .......... G02C 7/083; G02C 7/10; G02C 7/101; G02C 2202/12; G02C 2202/14; G02B 3/14; A61F 2/1635
USPC ................................................. 351/159.03
See application file for complete search history.

(56) References Cited

U.S. PATENT DOCUMENTS

| | | | |
|---|---|---|---|
| 8,755,124 | B2 | 6/2014 | Aschwanden et al. |
| 2004/0184158 | A1 | 9/2004 | Shadduck |
| 2012/0268712 | A1 | 10/2012 | Egan et al. |
| 2014/0002790 | A1 | 1/2014 | Pugh et al. |

FOREIGN PATENT DOCUMENTS

| | | |
|---|---|---|
| WO | 2008/108524 | 9/2008 |
| WO | 2008115251 | 9/2008 |
| WO | 2012/051167 | 4/2012 |
| WO | 2012/061411 | 5/2012 |
| WO | 2016/019359 | 2/2016 |

Fig. 4
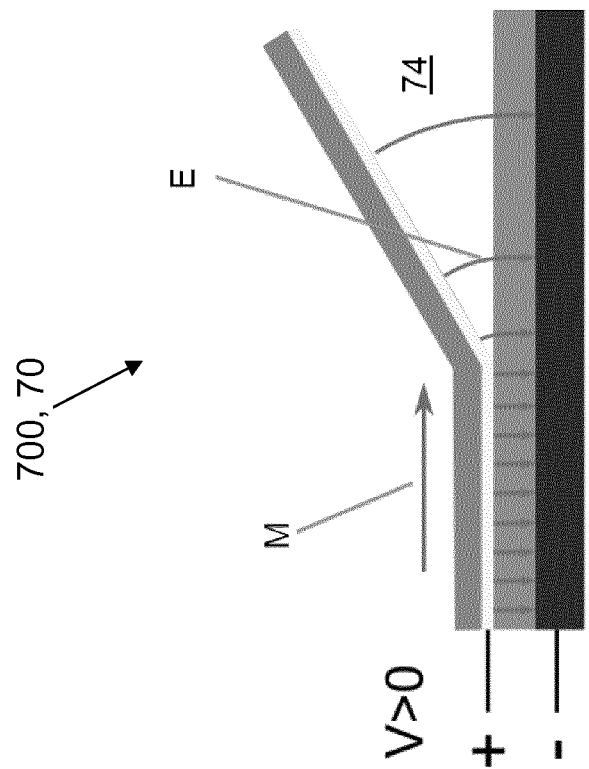
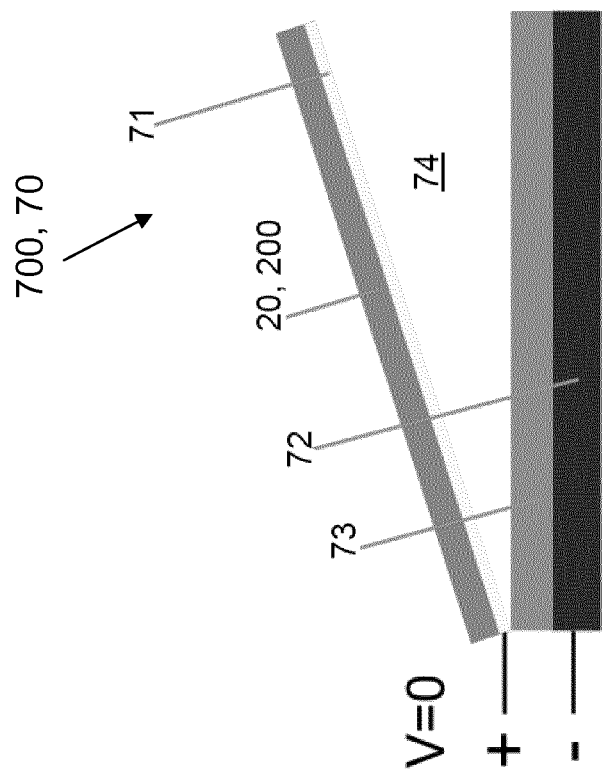

Fig. 15
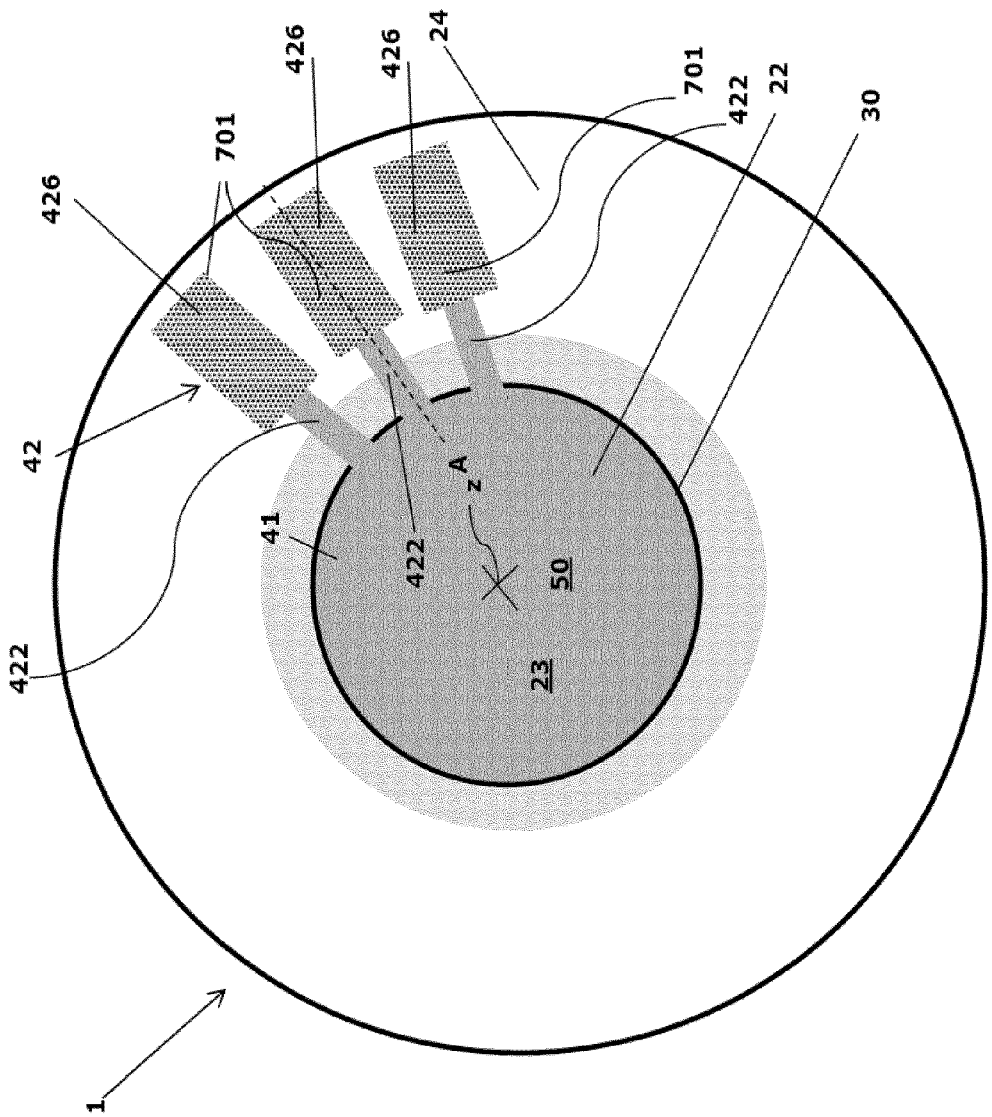
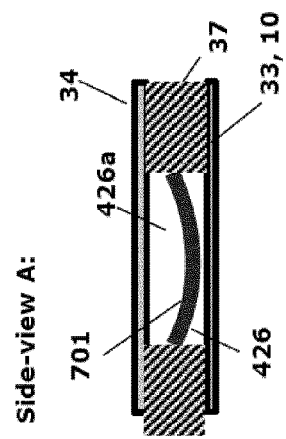

LENS COMPRISING AN ADJUSTABLE FOCUS LENGTH

CROSS-REFERENCE TO RELATED APPLICATIONS

This is the U.S. National Stage of International Application No. PCT/EP2016/074248 filed on Oct. 10, 2016, which was published in English under PCT Article 21(2), which in turn claims priority to European Patent Application No. 15188979.7 filed Oct. 8, 2015 and International Application No. PCT/EP2016/059572 filed on Apr. 28, 2016.

FIELD AND BACKGROUND

The present invention relates to a lens, particularly a contact lens having an adjustable focal length.

More particularly, the present invention relates to designs and methods of how to use and control such dynamic lenses. The present invention is not only applicable to contact lenses but also to other lenses that may be used in a variety of different applications.

In WO2008115251 a soft contact lens is described that has a body with a central zone aligned with the optical axis of the eye when a user wears the lens. In one embodiment the soft lens includes a chamber that extends from a lower portion of the lens to its central axis and is arranged such that when a person looks down, a fluid is squeezed from the reservoir and changes the optical characteristics of the lens.

Further, WO98/14820 describes a variable focus contact lens, which has a body with a first half and an opposite second half. The body also has a first peripheral surface, an opposite second peripheral surface and an associated focal length. The lens includes a first material that is resilient so that when a compressive force is applied to the first surface and the second surface, the focal length of the lens changes in proportion to the compressive force. A force-distributing structure is disposed for distributing forces within the lens so as to inhibit astigmatism in the lens.

Furthermore, the fluid-filled adjustable contact lens of US 2012/0268712 shows an exemplary contact lens which includes a lens chamber configured to be positioned on a pupil of a user wearing the contact lens; a reservoir fluidly connected to the lens chamber, an actuator configured to transfer fluid back and forth between the lens chamber and the reservoir; a sensor configured to sense movement from the user and transmit a control signal when a predetermined movement is performed by the user, and a processor configured to actuate the actuator upon receipt of the control signal from the sensor.

Further, U.S. Pat. No. 8,755,124 describes an adjustable optical lens comprising a membrane, a support for the membrane, a fluid between the membrane and the support, an actuator for deforming the membrane, and a rigid ring connected to the membrane surrounded by the rigid ring where the rigid ring has a defined circumference.

Based on the above, the problem underlying the present invention is to provide an improved contact lens that particularly allows to precisely adjust the focal length of the contact lens and achieves a high optical quality while being insensitive to the pressure of the eye lid.

SUMMARY

This problem is solved by a contact lens having the features of claim 1. Preferred embodiments of the present invention are stated in the corresponding sub claims or are described below.

According to claim 1, a lens for vision correction is disclosed, wherein the lens is particularly configured to be placed directly on the surface of an eye of a person, wherein the lens further comprises:

a transparent base element having a back side, preferably configured for contacting said surface of the eye, and a front side facing away from the back side, a transparent and elastically expandable membrane connected to said base element, wherein said membrane comprises a back side that faces said front side of the base element, a ring member connected to said back side of the membrane so that the ring member defines a curvature-adjustable area of the membrane, and wherein the lens comprises a lens volume adjacent said curvature-adjustable area of the membrane, which lens volume is delimited by the ring member, and wherein the lens comprises a reservoir volume arranged in a boundary region of the lens, wherein said two volumes are each filled with a transparent liquid, and a pumping means for transferring liquid from the reservoir volume to the lens volume (and preferably vice versa) such that the curvature of said curvature-adjustable area of the membrane changes and the focal length of the lens changes, and optionally a protecting means that is configured to reduce or prevent an effect of an eyelid of the user on said focal length when said eyelid rests on said boundary region of the lens.

According to a preferred embodiment (see also below) said protecting means is a rigid support structure that is configured to reduce or prevent (as said effect) a compression of the reservoir volume when an eyelid of the user rests on said boundary region of the lens on top of said reservoir volume.

In an embodiment the pumping means is configured for transferring liquid from the reservoir volume to the lens volume such that the curvature of said curvature-adjustable area of the membrane increases and the focal length of the lens decreases. In a further embodiment, the pumping means is also configured for transferring liquid in the other direction, i.e., from the lens volume to the reservoir volume so that the curvature of said curvature-adjustable area of the membrane decreases and the focal length of the lens increases. However, pumping the liquid back from the lens volume into the reservoir volume may also be accomplished by the tension of the membrane.

According to an embodiment of the contact lens according to the invention, the base element is configured to be placed directly on the surface of an eye of a person or user such that the back side of the base element contacts the eye. Thus, the incident light first passes through the membrane (i.e. through the curvature-adjustable area), then through the lens volume and finally through the base element before entering the eye on which it is placed.

In an alternative embodiment it is also possible that the membrane is configured to contact the eye (with the front side of the membrane facing away from the back side of the membrane). Here, the incident light first passes through the base element then passes through the lens volume and finally through the membrane (i.e. through the curvature-adjustable area) before entering the eye on which it is placed.

In an embodiment of the present invention, the ring member may be integrally formed with the membrane or the base element and may protrude from said back side of the membrane or the front side of the base element.

Further, in an embodiment of the present invention, said curvature adjustable-area of the membrane is configured for passing light through the curvature adjustable-area which deflects the light passing through it according to the current curvature of said area of the membrane. Particularly, said curvature-adjustable area corresponds to the clear aperture of the lens according to the invention.

Further, in an embodiment of the present invention, the base element may form a base lens. Furthermore, in an embodiment of the present invention, the base element is stiffer than the membrane. Likewise, the ring member is preferably stiffer than the membrane so as to be able to define the shape of the lens (i.e. of said curvature adjustable area). Further, in an embodiment of the present invention, said ring member is a circular ring member.

Furthermore, according to an embodiment of the lens according to the invention, the back side of the base element comprises a concave curvature so that the back side of the base element can fully contact the eye of a person.

Particularly, the base element can consist of or comprise one of the following materials:
A glass,
Polymers including elastomers (e.g. TPE, LCE, Silicones, e.g. PDMS, acrylics, urethanes),
A Plastic including thermoplasts (e.g. ABS, PA, PC, PMMA, PET, PE, PP, PS, PVC) and duroplasts,
A Gel (e.g. silicone hydrogel, polymacon or optical gel OG-1001 by Liteway).

Particularly, the membrane can consist of or comprise one of the following materials:
A glass,
A polymer including elastomers (e.g. TPE, LCE, Silicones, e.g. PDMS, acrylics, urethanes),
A plastic including thermoplasts (e.g. ABS, PA, PC, PMMA, PET, PE, PP, PS, PVC) and duroplasts.
A gel (e.g. silicone hydrogel, polymacon or optical gel OG-1001 by Liteway), Further, particularly, the liquid can be or comprise one of the following substances: a fluorinated silicone, water, an ionic liquid, a silicone, a contact lens cleaning solution, a salty water solution, an oil, a solvent. In certain embodiments the liquid may comprise a hydrophobic and a hydrophilic part. Further liquids that can be used in the present invention are stated below.

Furthermore, the pumping means can be formed by any suitable pump such as electrostatic pumps, e.g. peristaltic pumps, zipper actuator (see below), comb drive, resonance electrostatic pump, piezoelectric pumps such as bending piezo, bi-metal pump, bi- or tri-stable pumps, electro-wetting pump, molecular pumps, pumps employing electroactive polymers, S-shaped film actuators. Further, electromagnetic and thermally actuated pumps may be used.

According to a preferred embodiment of the present invention, said support structure comprises a plurality of ridges, wherein each ridge may be connected to the base element and/or the membrane.

Further, according to an embodiment of the present invention said ridges can extend from the ring member outwards and preferably divide the reservoir volume into a plurality of (e.g. elongate) sectors, wherein each sector is arranged between two neighboring ridges.

In an embodiment of the present invention, the pumping means comprises an actuator means that is configured to press liquid from the reservoir volume into the lens volume (e.g. by compressing the reservoir volume) such that the curvature of said curvature-adjustable area of the membrane increases and the focal length of the lens decreases. When the actuator means is turned off or its effect on the reservoir volume is reduced, the tension of the membrane pushes a corresponding amount of liquid from the lens volume back into the reservoir volume.

In an embodiment of the present invention, the actuator means of the pumping means is configured to compress at least one of said sectors, a specific selection of said sectors, or all of said sectors. Thus a varying amount of liquid can be transferred from the reservoir volume into the lens volume so that the focal length of the lens can be adjusted in corresponding increments (e.g. by compressing a sector completely at once) which allows a digital implementation of the actuation. The actuator means may also be configured to provide a continuous adjustment of the focal length by being configured to transfer corresponding precise amounts of liquid from individual sectors into the lens volume.

In an embodiment of the present invention, said sectors are each delimited by a first wall (e.g. ceiling) and a second wall (e.g. bottom) that faces the associated first wall, wherein the first walls are preferably formed by the membrane, and wherein the second walls are preferably formed by the base element or by the support structure.

Further, in an embodiment of the present invention, the actuator (here also denoted as zipper actuator) comprises a plurality of first electrodes, wherein each first electrode is attached to an associated first wall (or surface), and a corresponding number of second electrodes, wherein each second electrode is attached to an associated second wall (or surface) such that pairs of first and second electrodes are formed in each sector, wherein each pair of electrodes delimits an associated gap arranged between the respective first and second electrode in the respective sector, which gap is closable by means of a voltage applied to the respective pair of electrodes such that, when the respective gap is closed, liquid is pressed from the respective sector into the lens volume, and wherein, when the voltage applied to the respective pair of electrodes is decreased or turned off, the respective gap opens and a tension of the membrane causes a corresponding amount of liquid to flow back from the lens volume into the reservoir volume.

Further, in an embodiment of the present invention, each first electrode is electrically insulated with respect to the associated second electrode.

Further, according to an embodiment of the present invention, the electrodes may be actuated individually in a discrete or in a continuous manner. Discrete means that two electrodes forming a pair are either apart from each other forming a gap or contact each other (no gap). Thus a discrete amount of liquid can be transferred between the reservoir volume and the lens volume by such a pair of electrodes depending on the size of the gap. Continuous means that the gap between two electrodes is closed continuously so that an adjustable amount of liquid can be transferred between said volumes.

Further, particularly, the center of the lens (i.e. curvature-adjustable area) is configured to act as a spring that wants to open (e.g. unzip) the actuator(s), i.e. move the first and second electrode(s) apart from each other corresponding to the open state of the actuator in contrast to a closed state where the respective first and second electrode contact each other and the associated gap vanishes in particular.

Therefore, different equilibriums between these forces exist when different voltages are applied.

Further, in an embodiment, the first walls or surfaces are configured to stick to the respective second wall or surface through a compressive force of the actuator, e.g. generated by the respective pair of electrodes. Further, according to an alternative embodiment of the present invention, the electrodes or the insulation layers can be coated or structured such that they do not stick to each other when making contact.

Furthermore, in an embodiment of the present invention, the individual sectors are each fluidly connected or fluidly connectable to the lens volume via at least one opening. In the context of the present invention, fluidly connected means that there exists a flow connection such that liquid can pass via said connection from the lens volume to the reservoir volume and vice versa.

In an embodiment of the present invention, the at least one opening is a circumferential gap defined by a face side of the ring member, which face side faces the front side of the base element, and the base element, wherein particularly, when the curvature-adjustable area of the membrane assumes a maximal convex curvature, said face side of the ring member may contact the front side of the base element.

Further, in an embodiment of the present invention, the ring member is also connected to the front side of the base element, wherein an opening in form of a channel extending through the ring member may be provided for each sector to fluidly connect the respective sector to the lens volume.

Further, in an embodiment of the present invention, the ring member is also connected to the front side of the base element, wherein said openings are channels delimited by the ring member and the front side of the base element.

Furthermore, in an embodiment of the present invention, the ring member is 5 times, particularly 10 times, particularly 50 times, particularly 100 times, particularly 1000 times stiffer than the membrane.

Further, in an embodiment of the present invention, the ring member has a circularity and flatness better than 25 µm, particularly better than 10 µm, particularly better than 5 µm at an interface between the ring member and the membrane.

Furthermore, according to an embodiment of the present invention, the transparent liquid residing in the lens volume is a hydrophobic liquid, and wherein the liquid residing in the reservoir volume is a hydrophilic liquid such as a salty water solution such that in each sector an interface is formed between the hydrophilic liquid and the hydrophobic liquid. Here, preferably, the pumping means is configured to apply a voltage between the hydrophilic liquid residing in the respective sector and a surrounding wall of the respective sector, which wall encloses the respective sector and comprises an electrode (e.g. embedded into the wall), which electrode is electrically insulated from the hydrophilic liquid, such that the respective interface is moved towards the lens volume thus pushing hydrophobic liquid into the lens volume such that the curvature of said curvature-adjustable area of the membrane increases and the focal length of the lens decreases, wherein when said voltage is decreased or turned off, a tension of the membrane causes a corresponding amount of hydrophobic liquid to flow back from the lens volume into the reservoir volume.

Further, according to an embodiment of the present invention, the sectors are in flow connection with each other by means of a circumferential reservoir section formed by the reservoir volume, wherein said reservoir channel comprises a meandering shape at least in sections.

Furthermore, according to an embodiment of the present invention, the protecting means of the lens comprises at least one valve for closing and opening a flow connection between the reservoir volume and the lens volume. Here, the pumping means may be configured to pump a defined amount of liquid from the reservoir volume to the lens volume, wherein the valve may be configured to block a flow connection between the lens volume and the reservoir volume for the passage of fluid in order to maintain the transferred amount of liquid in the lens volume. Due to the tension of the membrane transferred liquid will flow back into the reservoir volume when the at least one valve is opened and the pumping means is not activated. Further, the pumping means may also be configured to pump transferred liquid from the lens volume into the reservoir volume via the opened valve. Particularly, due to the at least one valve, a pressure exerted onto the reservoir volume by means of an eyelid does not have an effect on the focal length of the lens since the flow of liquid from the reservoir volume into the lens volume can be blocked by means of the at least one valve which thus also forms a protecting means according to the present invention.

There are various valves known in the state of the art that can be used within the context of the present invention, for instance mechanical valves which may be actuated using magnetic fields (e.g. external magnetic fields or integrated magnetic inductors, electric fields (e.g. electrostatic forces or electro-kinetic actuation), particularly zipper actuators. Further, the valve may be actuated using the Piezo electric effect. The valve may also be actuated thermally, e.g. by means of a bimetallic material, using thermopneumatic actuation, or shape memory alloys. The valve may further be formed as a bistable system. Furthermore, non-mechanical valves may be used, which may be actuated electrochemically (e.g. by employing a phase change of a hydrogel, a sol-gel or a paraffin) or rheologically (e.g. electro-rheologically, ferrofluids). Particularly one or several electro-osmotic pumps can be used, see also below.

Further, externally actuated valves may be used (e.g. modular valves such as built-in rotary valves or membrane in-line valves).

Furthermore, according to an embodiment of the present invention, said support structure forming the protecting means comprises a rigid top covering the reservoir volume at least in sections from above and a rigid bottom covering the reservoir volume at least in sections form below. Here, in various embodiments, also the actuator elements described below (e.g. Piezo elements) may be arranged between said rigid bottom and said rigid top and may thus be protected by the support structure as well. The rigid bottom can be integrally formed with the base element. Further, the membrane may be connected to the rigid top. The rigid top and rigid bottom may be connected by a post structure or at least one or a plurality of posts.

Further, in an embodiment of the present invention, the lens comprises at least one reservoir channel forming part of the reservoir volume, via which reservoir channel the reservoir volume can be fluidly connected to the lens volume to transfer liquid from the reservoir volume to the lens volume and vice versa.

Further, in an embodiment of the present invention, the reservoir volume comprises a circumferential reservoir section that extends in an annular fashion around the lens volume, wherein this reservoir section is fluidly connected or connectable via the at least one reservoir channel to the lens volume.

Further, according to an embodiment of the present invention, the pumping means comprises a plurality of actuator elements, preferably in the form of Piezo elements, which are configured to be actuated (e.g. by applying a voltage to the individual Piezo element) such that liquid residing in the reservoir volume is pressed into the lens volume.

When the actuator elements are not actuated and the valve is open such that liquid can pass through the at least one reservoir channel from the lens volume to the reservoir volume, the tension of the membrane causes a corresponding amount of liquid to flow back from the lens volume into the reservoir volume.

Further, in an embodiment of the present invention, the actuator elements are arranged along the at least one reservoir channel and are configured to press against a deformable wall (e.g. a soft membrane with a Young's Modulus of e.g. 0.1 MPa to 2 MPa) of the at least one reservoir channel so as to push liquid from the reservoir volume into the lens volume.

Here, in an embodiment, the support structure may comprise a rigid top covering the reservoir volume at least in sections from above as well as a rigid bottom (e.g. a boundary region of the base element of the lens covering the reservoir from below) wherein the actuators may each be connected to the rigid bottom as well as to the rigid top via a deformable material layer that is softer than the rigid top and the rigid bottom. In an embodiment of the present invention, the membrane can be attached to the rigid top.

Further, in an embodiment of the present invention, the rigid top is supported on the rigid bottom via at least one post comprised by said support structure, wherein the at least one post extends between the rigid top and the rigid bottom.

Further, in an embodiment, the actuator elements (e.g. Piezo elements) may be configured to exert a lateral force onto said deformable wall of the at least one reservoir channel in a direction running along the extension plane of the base element.

Further, in an embodiment, the actuator elements (e.g. Piezo elements) may be arranged on opposing sides of the at least one reservoir channel and may be configured to compress the at least one reservoir channel from both sides so as to transfer liquid from the reservoir volume to the lens volume.

Further, in an embodiment, the lens may further comprise a plurality of reservoir channels extending from the lens volume outwards towards the circumferential reservoir section of the reservoir volume, wherein a plurality of said actuator elements (e.g. Piezo elements) is arranged between each two neighboring reservoir channels along the respective reservoir channels, so that each reservoir channel can be laterally compressed from two sides of the respective reservoir channel.

Preferably, the actuator elements that are arranged along the at least one reservoir channel (or between each two neighboring reservoir channels) are actuated in a successive fashion so as to press liquid from the reservoir volume into the lens volume. Particularly, said actuator elements (e.g. Piezo elements) arranged along the at least one reservoir channel may each be actuated by means of a square wave voltage, wherein the square wave voltages all comprise a phase shift with respect to one another such that the actuator elements (e.g. Piezo elements) expand from the outside inwards in succession, so as to press against the deformable wall of the respective reservoir channel and to thereby press liquid from the reservoir volume towards the lens volume. Here, the actuator elements may also be configured to block the flow of fluid through the respective reservoir channel once a desired volume of liquid has been transferred from reservoir volume to the lens volume. Alternatively, the actuating elements may be continuously actuated to prevent backflow of liquid from the lens volume towards the reservoir volume. Preferably, the actuator elements are actuated in a resonant mode to generate a strong liquid flow at a low power consumption.

In another embodiment, the actuator elements (e.g. Piezo elements) may be connected to the rigid top of the support structure and may be arranged between said rigid top and the deformable wall of the at least one reservoir channel on a side of the deformable wall facing away from the base element and are configured to press against the deformable wall (e.g. soft membrane) of the at least one reservoir channel, which deformable wall faces the base element in a direction parallel to the optical axis of the lens.

Further, in an embodiment of the present invention, the actuator elements are formed as ring-shaped (or cylinder-shaped) Piezo elements which are coaxially arranged around the lens volume with respect to the optical axis of the lens.

Here, in an embodiment, the circumferential reservoir section of the reservoir volume is arranged further outward in the radial direction of the lens than the lens volume.

Furthermore, in an embodiment, said ring-shaped (or cylinder-shaped) actuator elements (e.g. Piezo elements) are configured to expand in an axial direction running parallel to said optical axis of the lens when being actuated, such that said actuators press against a deformable wall (e.g. soft membrane) of the at least one reservoir channel so as to push liquid from the reservoir volume into the lens volume.

Here, again, the support structure may comprise a rigid top covering the reservoir volume at least in sections from above as well as a rigid bottom (e.g. a boundary region of the base element of the lens covering the reservoir from below), wherein the actuator elements may each be connected to the rigid bottom via a deformable material layer that is e.g. at least 2 times softer than the rigid top and the rigid bottom, and are arranged between said rigid bottom and the deformable wall of the at least one reservoir channel. Further, between each two neighbouring actuator elements a deformable material (e.g. a soft polymer) may be arranged.

Particularly, the actuator elements (e.g. Piezo elements) may each be actuated by means of a square wave voltage, wherein the square wave voltages all comprise a phase shift with respect to one another such that the actuator elements expand from the outside inwards in succession, so as to press against the deformable wall of the respective reservoir channel and to thereby press liquid from the reservoir volume towards the lens volume according to the principle of a peristaltic pump. Here, the actuator elements may also be configured to block the flow of fluid through the respective reservoir channel once a desired volume of liquid has been transferred from the reservoir volume to the lens volume. Alternatively, the actuator elements may be continuously actuated to prevent backflow of liquid from the lens volume towards the reservoir volume.

Further, in an embodiment the rigid top is supported on the rigid bottom (e.g. boundary region of the base element) of the lens via at least one post comprised by said support structure, wherein said at least one post preferably extends between the rigid top and the rigid bottom and is preferably arranged between neighbouring actuator elements.

Further, in an embodiment, outside the at least one reservoir channel a deformable material (e.g. a soft polymer) may be arranged between the actuator elements and the rigid top.

Further, in yet another embodiment, said ring-shaped actuator elements (e.g. Piezo elements) are configured to expand in a radial direction running perpendicular to said optical axis when being actuated, such that said actuator elements press against a deformable wall (e.g. soft membrane) of the at least one reservoir channel so as to push liquid from the reservoir volume into the lens volume.

Here, again, in an embodiment, the support structure may comprise a rigid top covering the reservoir volume at least in sections from above as well as a rigid bottom (e.g. a boundary region of the base element of the lens), wherein the actuator elements may each be connected to the rigid bottom via a deformable material layer that is softer than the rigid top and the rigid bottom, and are arranged between said rigid bottom and the deformable wall of the at least one reservoir channel. Further, between neighbouring actuator elements a deformable material (e.g. a soft polymer) may be arranged.

Particularly, said ring-shaped actuator elements (e.g. Piezo elements) may each be actuated by means of a square wave voltage, wherein the square wave voltages comprise a phase shift such that the Piezo elements expand from the outside inwards in succession, so as to deform the deformable wall of the respective reservoir channel and to thereby press liquid from the reservoir volume towards the lens volume. Here, the actuating elements may also be configured to block the flow of fluid through the respective reservoir channel once a desired volume of liquid has been transferred from reservoir volume to the lens volume. Alternatively, the actuating elements may be continuously actuated to prevent backflow of liquid from the lens volume towards the reservoir volume.

Further, in an embodiment, the rigid top is supported on the rigid bottom via at least one post comprised by said support structure, wherein said at least one post preferably extends between the rigid top and the rigid bottom. Here, preferably, an inner post may be arranged in the radial direction within the innermost ring-shaped actuator element while an outer post may be arranged in the radial direction outside of the outermost ring-shaped actuator element.

Further, in an embodiment, outside the at least one reservoir channel the ring-shaped actuator elements may be connected to the rigid top via a deformable material layer, that may be connected to a rigid element forming part of the support structure, which rigid element may be connected to said rigid top.

In yet another embodiment of the present invention, the pumping means comprises a single ring-shaped actuator element, preferably in the form of a Piezo element, which is configured to be actuated such that liquid residing in the reservoir volume is pressed into the lens volume, wherein said actuator element is preferably configured to expand outwards in a radial direction running perpendicular an optical axis of the lens when being actuated, such that said actuator element compresses a circumferential reservoir section of the reservoir volume (which preferably surrounds the actuator element), which circumferential reservoir section is fluidly connected to the lens volume (e.g. via at least one reservoir channel), so as to push liquid from the reservoir volume into the lens volume.

Here, in an embodiment, the support structure may comprise a rigid top covering the reservoir volume (e.g. the circumferential reservoir section) at least in sections from above as well as a rigid bottom (e.g. a boundary region of the base element of the lens covering the reservoir from below), wherein the ring-shaped actuator element may be connected to the rigid bottom and the rigid top via a deformable material layer, respectively, which layers are softer than the rigid top and the rigid bottom.

Further, in an embodiment, the actuator element may also be configured to block the flow of fluid through the respective reservoir channel once a desired volume of liquid has been transferred by maintaining the reduced volume of the circumferential section of the reservoir volume.

Further, the rigid top is supported on the rigid bottom via at least one post comprised by said support structure, wherein said at least one post may be arranged in the radial direction outside of the actuator element and may form an (e.g. circumferential) lateral outer wall of the circumferential reservoir section.

In yet another embodiment of the present invention, the actuator elements, preferably in the form of Piezo elements, are arranged along the at least one reservoir channel and are configured to bend towards the at least one reservoir channel when being actuated so as to compress the at least one reservoir channel upon bending of the respective actuator element such that liquid is pushed from the reservoir volume into the lens volume.

Here, in an embodiment, the support structure may comprise a rigid top covering the reservoir volume at least in sections, particularly the at least one reservoir channel, from above as well as a rigid bottom (e.g. a boundary region of the base element of the lens covering the reservoir from below), wherein the actuator elements may each be connected to the rigid top, particularly via a rigid mount, wherein particularly the bending actuator elements form part of a wall of the at least one reservoir channel and may each enclose an air gap with the rigid top.

In an embodiment, the bending actuators elements (e.g. Piezo elements or a bistable bi-metal actuator) may be configured to be bend in a direction towards the base element in order to compress the at least one reservoir channel.

The at least one reservoir channel may extend outwards from the lens volume and may be fluidly connected to a circumferential section of the reservoir volume with the lens volume.

Preferably, actuators that are arranged along a reservoir channel are actuated in a successive fashion so as to press liquid from the reservoir volume into the lens volume. Particularly, in case of Piezo elements, said actuators arranged along the at least one reservoir channel may each be actuated by means of a square wave voltage, wherein the square wave voltages comprise a phase shift such that the Piezo elements expand from the outside inwards in succession, so as to press against the wall of the respective reservoir channel and to thereby press liquid from the reservoir volume towards the lens volume. Here, the actuating elements may also be configured to block the flow of fluid through the respective reservoir channel ones a desired volume of liquid has been transferred from reservoir volume to the lens volume. Alternatively the actuating elements may be continuously actuated to prevent backflow of liquid from the lens volume towards the reservoir volume The lens may further comprise a plurality of reservoir channels extending from the lens volume outwards towards the circumferential section of the reservoir volume, which may be compressed by bending actuator elements as described above.

In a further embodiment of the present invention, the reservoir volume comprises at least one chamber that is connected via the at least one reservoir channel to the lens volume, wherein the pumping means comprises at least one actuator element, preferably in the form of a Piezo element, which is configured to bend towards the chamber when being actuated so as to compress the chamber upon bending of the respective actuator element such that liquid is pushed from the chamber into the lens volume.

Here, in an embodiment, the support structure may comprise a rigid top covering the chamber from above as well as a rigid bottom (e.g. a boundary region of the base element of the lens covering the reservoir from below) wherein the bending actuator element is connected to the rigid top, particularly via a rigid lateral wall of the chamber that connects the rigid top with the rigid bottom, wherein particularly the bending actuator element also forms part of a wall (e.g. ceiling) of the chamber and may enclose an air gap with the rigid top. It is also possible that the actuator element is directly exposed to the outside world.

In a further embodiment, the reservoir volume may comprise several separate chambers that may each be compressed in this way by means of such a bending actuator element (e.g. Piezo element), wherein the respective chamber is connected to the lens volume by an associated reservoir channel that extends outwards from the lens volume to the respective chamber.

Also here, the respective actuator element may also be configured to block the flow of fluid back into the respective chamber once a desired volume of liquid has been transferred from the respective chamber to the lens volume by maintaining the compressed state of the respective chamber or by continuous pumping of liquid to counteract the pressure by the membrane in the lens volume.

Furthermore, according to an embodiment of the present invention, the lens comprises a sensor means that is configured to sense a movement of the person wearing the lens, and to provide an output signal in response to a predetermined movement of said person, wherein particularly said movement is a movement of an eyelid or of an eye of said person or the deformation of the crystalline lens of said person.

The sensor means comprises at least a first sensor comprising a light source, particularly LED, and a photosensitive element, particularly a photodiode, wherein said first sensor is configured to emit light by means of the light source and to detect emitted light by means of said photosensitive element that has been scattered back by the eye and particularly the crystalline lens or eyelid of the user. Preferably, the lens comprises three such sensors namely a further second and third sensor which are preferably arranged on the corners of a virtual triangle.

Further, the sensor means may be one of: a photosensitive element, a pressure sensing element, a capacitive sensing element, a thermal sensor, particularly a resistor. Particularly, said resistor may extend along the periphery of the contact lens. When the person covers the resistor with an eyelid, the temperature of the resistor rises due to heat transferred from the eyelid to the resistor.

Further, according to an embodiment of the present invention, the lens further comprises a processing unit (also denoted controller) that is configured to actuate the pumping means (e.g. the respective actuator or actuating element) and/or valve (when present in the respective embodiment), so as to transfer liquid from the reservoir volume into the lens volume or vice versa in response to the output signal provided by the sensor or in response to an output signal provided by an external device.

The lens comprises an energy source (e.g. a battery), for powering the pumping means, the sensor means, and/or the controller.

Further, according to an embodiment of the present invention, said electric energy source is configured to be charged by means of one of:
  inductive charging;
  light, wherein particularly the contact lens comprises a solar cell or a photo diode;
  using the thermoelectrical effect, wherein particularly the contact lens comprises a Peltier element;
  harvesting eye lid movements, wherein particularly the contact lens comprises a flexible capacitance for transforming eye lid movements into electrical energy that can be stored in said energy source/battery.

According to a further aspect of the present invention, a method for manufacturing a contact lens, particularly according to the invention, is proposed, comprising the steps of:
  providing a base element (e.g. by way of molding, e.g. out of a silicone hydrogel, or a silicone coated with silicone hydrogel) which includes a support structure or protecting means (e.g. as described herein),
  providing an elastically deformable membrane (e.g. by way of molding or coating, e.g. out of a silicone hydrogel or a silicone coated with silicone hydrogel) comprising a ring member connected to a back side of the membrane,
  bonding of the base element including the support structure (or protecting means) to the membrane including the ring member and thereby forming a lens volume and a reservoir volume of the contact lens which is filled with a transparent liquid Furthermore, also the other components described herein, such as the pumping means, the sensor means, and the controller may be mounted to the base element or the deformable membrane before said bonding of the support structure and/or membrane and before said filling of the lens volume.

Particularly, one of the following is applied to the membrane and/or the base element: a coating, at least one electrode, an insulation layer and optionally an anti-stiction layer.

Particularly, the ring member can be plasma bonded to the membrane if it is not an integral part of the membrane. Furthermore, the base element can be plasma bonded or glued to the membrane.

Further, particularly, the ring member can be integrally formed with the membrane (e.g. upon molding of the membrane) and include cut-outs for fluid flow channels, wherein the ring member can be stiffened by means of irradiating it with ultraviolet light or wherein the membrane can be softened by irradiating it with ultraviolet light. Materials that may be used for the ring member and membrane that can be stiffened by irradiating them with ultraviolet light are for example: silicones or urethanes. Further, materials that may be used for the membrane and ring member that can be softened by irradiating them with ultraviolet light are for example: silicones or urethanes).

Alternatively, a primer may be applied to the mold which is designed to chemically stiffen the ring member during molding of the membrane and integral ring member.

Further, according to an embodiment of the present invention, said filling is conducted using osmosis after said bonding has been performed.

For this, particularly, a pre-defined amount of water soluble salt is arranged on the base element or membrane before bonding so that said salt is arranged in the lens volume and/or lens reservoir after bonding, wherein then the bonded base element and membrane is soaked in the transparent liquid which enters the lens volume and reservoir volume by way of osmosis.

Further, according to an alternative embodiment of the present invention, said filling is conducted before said bonding, wherein said liquid is filled into a dent formed by the membrane (the dent may be only a temporal dent formed for the filling process), wherein thereafter said bonding is conducted, and wherein the lens volume and/or reservoir volume is freed from gas residing therein after said bonding.

Here, a glue, particularly a glue ring between the edge of the membrane and the edge of the base element, may be used, which glue is cured after freeing the lens volume/reservoir volume from said gas. This allows to adjust the initial focal length of the contact lens. Here, a glue that can be hardened by irradiating it with ultraviolet light may be used, wherein curing of the glue is then conducted by irradiating the glue with ultraviolet light after said degassing (i.e. freeing said volumes from the gas therein).

Furthermore, the filling might be performed under a vacuum. Additionally, the liquid volume can be defined by overfilling the membrane element and then pushing the base element into the liquid, where excess liquid is pushed out of the lens volume and reservoir volume. When the desired liquid amount is present in the lens volume and the reservoir volume the membrane and the base element are glued together. To facilitate this geometrical fill method, the membrane and base element are supported by rigid holders (e.g. a plastic parts).

Furthermore, in an embodiment where filling is performed before bonding, the membrane may be provided (instead of molding) by vapor coating the liquid arranged on the base element by means of vapor depositing (coating) A material that can be used to vapor-deposit the membrane (the ring member is provided before (e.g. arranged on the base element) is e.g. parylene (i.e. chemically vapor deposited poly(p-xylylene) polymers).

Besides contact lenses, the present invention can be used in a large variety of applications that require an adjustable focal length including ophthalmology equipment such as phoropters, refractometers, pachymeters, biometrie, perimeters, refrakto-keratometers, refractive lens analyzers, tonometers, anomaloscop, contrastometers, endothelmicroscopes, anomaloscopes, binoptometers, OCT, rodatests, ophthalmoscopes, RTA or in lighting, machine vision, laser processing, mobile phone cameras, light shows, printers, metrology, head worn glasses, medical equipment, robot cams, motion tracking, microscopes, telescopes, endoscopes, binoculars, research, surveillance cameras, automotive, projectors, ophthalmic lenses, range finder, bar code readers, web cams.

According to a further aspect of the present invention, an optical assembly is disclosed, comprising: a lens according to the invention, and a transparent enclosure, wherein said lens is arranged or embedded in said enclosure, and wherein preferably said enclosure forms or comprises a further lens. Here, particularly, since the lens is arranged or embedded in said enclosure it does not necessarily have to be configured to be placed directly on the surface of an eye of a user.

According to yet another embodiment of the present invention, the lens comprises a pumping means (e.g. as described herein) and a valve between the reservoir volume and the lens volume to reduce energy demand. Particularly, the lens is configured to close the valve as soon as a desired focal power has been adjusted so that the fluid is held in the lens volume (optical zone). Particularly, the lens can be configured to actuate the valve (e.g. open and close the valve) by means of a valve control signal, wherein the lens is configured to open the valve before every tuning step and to close it after every tuning step. Particularly, the lens is configured to detect a specific movement, e.g. an eye or eye-lid movement, or a head position (e.g. looking down) of the person wearing the lens, wherein the lens is configured to generate the respective valve control signal after detection of an associated pre-defined movement or head position.

Further, according to an embodiment of the present invention, the lens is configured to harvest energy from body and/or eye movements of the person wearing the lens so as to reduce the energy storage (battery or supercapacitor) capacity needed. For this, the lens may comprise a reservoir or channel in which a fluid can be pumped whenever the eye lid or eye is moving to build up a certain pressure, wherein this pressure and fluid can then be used for a next actuation step. Further, the lens may comprise a magnet dynamo system, a pump for pumping of an ionic liquid, or an electroactive polymer (EAP) material.

According to a further embodiment of the present invention, the pumping means is an electro-osmotic pumping means and comprises at least a first electro-osmotic pump or is formed as a first electro-osmotic pump, which first electro-osmotic pump comprises a porous membrane, a first electrode, and a second electrode, wherein the porous membrane is arranged between said electrodes such that the distance between the porous membrane and electrode is particularly less than 100 µm, preferably less than 50 µm. Most preferably the electrodes contact the osmotic membrane, respectively.

Particularly, the first electro-osmotic pump (e.g. the porous membrane and the two electrodes) can comprise an annular porous membrane or can comprise a porous membrane having the shape of a circular arc. However, said first pump/porous membrane may also comprise another contour (e.g. any shape, disk, square or else) and may be located at the periphery of the lens.

Particularly, in case the electrodes are not in contact with the porous membrane, the electrodes can be formed as e.g. thin metal films and can be attached to the base element and to the membrane (e.g. by coating the electrodes onto the base element/membrane) such that said compartments of the reservoir volume are arranged between the respective electrode and the porous membrane and liquid is exchanged from one compartment to the other. Furthermore, the electrodes can be porous and can define the compartments of the reservoir volume or a portion of them.

Further, particularly, the electrodes can be in contact with the porous membrane, wherein particularly the porous membrane is arranged between the two electrodes. Here, the electrodes can be (e.g. thin) metal films that are deposited on the porous membrane (but not in the pores). Alternatively, the electrodes can be porous, and may be formed by or comprise a carbon fabric or a layer of carbon nanotubes (also porous) deposited on the surfaces of the porous membrane, but not in the pores to prevent short circuits.

Particularly, the first electro-osmotic pump (e.g. the electrodes and the porous membrane arranged between the two electrodes) may comprise a thickness that is preferably less than 100 µm, preferably less than 50 µm, most preferably less than 25 µm.

Furthermore, according to an embodiment, the first electro-osmotic pump or at least the porous membrane comprises a curved shape following a curvature of the lens (e.g. contact lens).

Further, according to an embodiment, the active surface of the osmotic membrane (e.g. the surface through which fluid is actually being pumped) is less than 200 $mm^2$, preferably less than 150 $mm^2$, most preferably less than 100 $mm^2$.

Preferably, according to an embodiment, the porous membrane is made of or comprises one of the following materials: polyester (PET), polydimethylsiloxane (PDMS), polycarbonate (PC), polyimide (PI), poly(ether ether ketone) (PEEK), polyvinylidenfluorid (PVDF), polytetrafluorethylen (PTFE), Nafion, polypropylene (PP), polyethersulfone (PES), polyacrylonitrile (PAN), nylon, cellulose acetate, mixed cellulose esther, glass fiber, rubber material, ceramic material, non-conductive nanowires or nanotubes; particularly a surface of each of the above stated materials for the porous membrane can be functionalized by plasma treatment and/or by means of a chemical treatment (e.g. sulfonated) in order to increase the surface charge or zeta potential of the material. The absolute value of the zeta potential carried at the pores walls is particularly larger than 10 mV, more preferably larger than 30 mV, most preferably larger than 50 mV.

Preferably, according to an embodiment, the liquid in the lens volume/reservoir volume that is pumped by the at least one first electro-osmotic pump (or by further electro-osmotic pumps, see below) can be one of: pure water, saline with a concentration smaller than 100 mM, most preferably smaller than 10 mM, an isotonic solution, an isotonic saline solution, a sugar alcohol solved in water, mannitol in pure water, particularly mannitol 5% (weight) in pure water, alcohol, or any combination of the above liquids. Particularly, mannitol in pure water, particularly mannitol 5% (weight) in pure water is beneficial because it is isotonic with tear liquid (no reason for the water to leave the lens due to osmotic pressure) and biocompatible. Particularly, mannitol ($C_6H_{14}O_6$) has the CAS number 69-65-8.

Particularly, if the (e.g. contact) lens is filled with pure water and immersed in saline, then the water in the lens will go through the (e.g. silicone) membrane to balance the difference in salt concentration or tonicity. So, the lens will "dry". Thus it is beneficial that the liquid inside and outside have the same tonicity. Particularly, inner or outer surfaces of the base element and of the membrane can be coated with parylene C to reduce significantly water permeability and avoid or slow down a "drying" effect of the (e.g. contact) lens.

Outer surfaces of the (e.g. contact) lens can be coated with a hydrogel to ensure a permanent liquid film all around the lens and avoid "drying" of the lens. If there is no film of tear liquid around the lens, then the water may evaporate through the membrane in the air.

Preferably, according to an embodiment, the porous membrane comprises pores having a pore size in the region from 1 nm to 10 μm, preferably from 10 nm to 1 μm, most preferably from 100 nm to 400 nm.

Further, according to an embodiment the porous membrane comprise a pore density in the range from $1\times10^7$ to $1\times10^{10}$ pores/cm$^2$ more preferably in the range from $1\times10^8$ to $1\times10^9$ pores/cm$^2$.

Furthermore, according to an embodiment, the electrodes can be made out of or comprise one of the following materials: a metal, carbon, glassy carbon, graphite, carbon nanotubes, graphene, boron-doped diamond, silver, silver chloride, gold, platinum, iridium, a thin film or a nanowire film, conductive polymer (PEDOT), a composite (e.g. microparticles or nanoparticles in a PDMS matrix) or any combination thereof.

Furthermore, according to an embodiment, the porous electrodes comprise a thickness that is less than 150 μm, preferably less than 50 μm, most preferably less than 25 μm.

Furthermore, according to an embodiment, the electrodes are located close to the membrane, particularly at a distance of less than 100 μm, preferably less than 50 μm, most preferably less than 25 μm.

Further, according to an embodiment, said electrodes are configured to let said liquid pass through. Particularly, said electrodes are porous to let the liquid flow through. Particularly in case of electrodes that allow the passage of liquid, the respective electrode can be in contact with the porous membrane (e.g. can be bonded to the porous membrane). In this case the thickness of the first electro-osmotic pump (e.g. the sandwich electrode-membrane-electrode) is less than 300 μm, preferably less than 100 μm, most preferably less than 50 μm.

Preferably, the osmotic membrane assembly is configured to use a voltage for pumping liquid that is less than 10V, preferably less than 5V, most preferably less than 1.2V.

Particularly, the applied voltage is selected such that no electrochemical side reactions occur, to avoid loss of efficiency and formation of gaseous or other side products.

Particularly, the first electro-osmotic pump is configured to achieve a volume flow of the liquid entering or leaving the optical zone that is higher than 0.1 μl/s, preferably higher than 0.5 μl/s, most preferably higher than 1 μl/s.

Furthermore, according to an embodiment, the first electro-osmotic pump is configured to pump liquid at the desired volume flow against a counter pressure being higher than 10 Pa, preferably higher than 100 Pa, most preferably higher than 1000 Pa.

Further, according to an embodiment, said at least one first electro-osmotic pump separates an upper compartment of the reservoir volume from a lower compartment of the reservoir volume, which compartments are arranged on top of one another, wherein the upper compartment is arranged between said first electro-osmotic pump and said membrane having said curvature-adjustable area, and wherein particularly the lower compartment is arranged between said first osmotic membrane assembly and a bottom of said base element. Alternatively, when the porous membrane does not contact the electrodes, the porous membrane may separate an upper compartment of the reservoir volume from a lower compartment of the reservoir volume, which compartments are arranged on top of one another, wherein the upper compartment is arranged between said porous membrane and said membrane having said curvature-adjustable area, and wherein particularly the lower compartment is arranged between said porous membrane and a bottom of said base element.

Particularly, either the lower or the upper compartment is connected to the lens volume by at least one channel.

Further, according to an embodiment of the present invention, in case the lower compartment is connected to the lens volume via at least one channel, the first electro-osmotic pump is configured to pump liquid from the upper compartment into the lower compartment and thereby into the lens volume or from the lower compartment to the upper compartment and thereby from the lens volume into the reservoir volume depending on a voltage applied to said electrodes.

Further, according to an embodiment of the present invention, in case the upper compartment is connected to the lens volume via at least one channel, the first electro-osmotic pump is configured to pump liquid from the lower compartment into the upper compartment and thereby into the lens volume, or from the upper compartment to the lower compartment and thereby from the lens volume into the reservoir volume depending on a voltage applied to said electrodes.

The electro-osmotic pumps described herein particularly work in the following manner. Particularly, the porous membrane of the respective pump comprises pores that form channels (particularly nanochannels) connecting one surface of the porous membrane to the other opposing surface (transversal pores). In the pores, at a liquid/membrane interface, an electrical double layer is formed due to the fact that the surface of the porous membrane always has a certain charge or zeta potential. If the surface is charged negatively (e.g. PET membrane) the positive ions will adsorb at the surface, the higher the charge, the more the positive ions. By applying a voltage between the electrodes, one can generate an electric field across the pores. The positive ions will move towards the negative electrode. By friction, the positive ions will set the bulk liquid in motion also towards the negative electrode. If the surface is charged positively, liquid will flow towards the positive electrode.

Particularly, in case the pore diameter is very small, one can pump against higher pressure. If the pore diameter is larger, one can pump faster but against less pressure. Particularly, the shorter the distance between the electrodes, the higher the electric field and the more efficient the respective electro-osmotic pump is. Preferably, the electrodes are designed such that a tiny fraction of the voltage is lost at the electrode/liquid interface, such that most of the voltage drop is used to generate an electric field across the pores. Also, preferably, the voltage is chosen such that almost no gas bubbles are generated by the electrodes. Particularly, the voltage is less than or equal to 1.2 V.

Further, according to an embodiment of the present invention, the lower or the upper compartment is connected to the lens volume via at least one channel that may extend between the ring member and the base element or may be integrated into the ring member or into the base element.

Further, according to an embodiment of the present invention, said first electro-osmotic pump is arranged adjacent a lateral (particularly circumferential and outwardly facing) surface of the ring member, which lateral surface connects an upper face side of the ring member (via which upper face side the ring member is connected to the membrane) to a lower face side of the ring member, which lower face side faces away from said upper face side.

Further, according to an embodiment of the present invention, said first electro-osmotic pump is connected to a lower face side of the ring member, which lower face side faces away from an upper face side of the ring member, via which upper face side the ring member is connected to said membrane.

Further, according to an embodiment of the present invention, the lens comprises a further ring member surrounding the upper compartment, which further ring member is particularly formed separately regarding said ring member, and wherein said first electro-osmotic pump is connected to a lower face side of the ring member and/or to a lower face side of the further ring member. Particularly, the lower face side of the ring member faces away from an upper face side of the ring member, via which upper face side the ring member is connected to said membrane, and wherein particularly the lower face side of the further ring member faces away from an upper face side of the further ring member, via which upper face side the further ring member is connected to said membrane.

Further, according to an embodiment of the present invention, said first electro-osmotic pump comprises a first contact lead for connecting a battery to the first electrode, and a second contact lead for connecting said battery to the second electrode, wherein particularly said first contact lead is arranged at a first end of the first electro-osmotic pump, and wherein particularly said second contact lead is arranged at an opposite second end of the first electro-osmotic pump.

Further, according to an embodiment of the present invention, the first electro-osmotic pump comprises a curved shape, particularly an elongated curved shape, wherein particularly the course of said pump/assembly follows a circular arc.

Further, according to an embodiment of the present invention, the lens comprises a support structure, which may comprise pillars or may be formed as a grid, arranged in the lower compartment for supporting said first electro-osmotic pump or at least its porous membrane, and/or a support structure (which may comprise pillars or may be formed as a grid) arranged in the upper compartment for supporting said first electro-osmotic pump or at least its porous membrane.

Further, according to an embodiment of the present invention, the base element comprises a recess, which is particularly arranged on the front side of the base element, wherein said lower compartment is arranged in said recess.

Particularly, in an embodiment, said recess is a curved and/or circumferential recess.

Further, according to an embodiment of the present invention, the recess furthers comprises two opposing (e.g. circumferential) steps for aligning said first electro-osmotic pump with respect to the recess. Particularly said first pump is formed to butt against the steps in a form-fitting manner.

Further, according to an embodiment of the present invention, the base element comprises a circumferential step aligning the ring member with respect to the base element.

Further, according to an embodiment of the present invention, the lens comprises a battery, particularly a rechargeable battery (see also above). The battery can comprise a plurality of separate cells.

Further, according to an embodiment of the present invention, the battery is arranged outside the lower and upper compartments. Alternatively, the battery may be arranged in the lower compartment (or in the upper compartment).

Further, according to an embodiment of the present invention, the lens comprises a power interface connected to the battery, e.g. an inductive coil, particularly an RF coil, configured for inductive charging of the battery.

Further, according to an embodiment of the present invention, the lens comprises a sensor assembly configured to detect one of: an eye lid movement, a fully closed eyelid, a partially closed eye lid of the person wearing said lens and to generate a corresponding control signal indicative of said detected movement or eye lid state (fully or partially closed). Particularly, said sensor assembly can be configured to perform a capacitive, inductive, or impedance measurement. Further, the sensor assembly may be an optical sensor (e.g. may comprise one, particularly two or multiple photodiodes).

Particularly, the sensor assembly comprises two spaced apart sensors (e.g. photodiodes), particularly two diametrically arranged sensors, wherein the sensor assembly is configured for differential sensing so as to compensate for ambient conditions, such as external lightening, humidity changes in the air, chemical changes (e.g. ion concentration) in the tear fluid.

Further, according to an embodiment of the present invention, the lens comprises a processing unit configured to control a voltage applied to the electrodes of the first osmotic membrane assembly depending on said control signal of the sensor assembly and/or depending on a control signal in the form of a modulated power supply signal received by said power interface.

Further, according to an embodiment of the present invention, the power interface, the sensor assembly, and the processing unit are mounted to the ring member, particularly so as to form a pre-assembled assembly that can be mounted with respect to the base element as a whole.

Further, according to an embodiment of the present invention, the ring member, the power interface, the sensor assembly and the processing unit are mounted on a carrier, particularly in the form of a flexible printed circuit board (FPC). Particularly, the ring member can be a separate element with respect to the carrier (FPC), but can also be formed by the carrier (e.g. FPC) itself, i.e., the ring member can be an integral portion of the carrier (e.g. FPC).

Particularly, said carrier may comprise one or two protruding regions for carrying said sensor assembly, and processing unit. Particularly, the respective protrusion is arranged in an associated dedicated installation space of the lens, particularly in a channel of the lens, which channel may connect one or two lower compartments to the lens volume.

Further components which may be integrated on the carrier (e.g. FPC) or may be arranged in a dedicated installation space (see above) of the lens can be: a power converter, a rectifier circuit, a voltage stabilization circuit, a battery charging circuit, a data storage device (e.g. EEPROM), circuitry for detection and control of timing for eyelid movement synchronized functions such as eyelid induced charging, eye lid assisted liquid pumping etc. Also functions like automatic standby mode or sleep mode with reduced power consumption (e.g. from maximal switching voltage down to minimum hold voltage), or malfunction detection (e.g. short circuits, empty battery) may be integrated onto said carrier.

Further, according to an embodiment of the present invention, the lens comprises a second electro-osmotic pump, which second electro-osmotic pump comprises a porous membrane, a first electrode, and a second electrode, wherein the porous membrane of the second electro-osmotic pump is arranged between said electrodes of the second electro-osmotic pump such that said electrodes of the second electro-osmotic pump contact the osmotic membrane of the second osmotic membrane assembly, respectively.

Further, according to an embodiment of the present invention, said second electro-osmotic pump separates a further upper compartment of the reservoir volume from a further lower compartment of the reservoir volume, which further compartments are arranged on top of one another, wherein the further upper compartment is arranged between said second electro-osmotic membrane assembly and said membrane comprising said curvature-adjustable area, and wherein the further lower compartment is arranged between said second electro-osmotic pump and a bottom of said base element of the lens according to the invention. Alternatively, when the porous membrane does not contact the electrodes of the second pump, the porous membrane of the second pump may separate a further upper compartment of the reservoir volume from a further lower compartment of the reservoir volume, which compartments are arranged on top of one another, wherein the further upper compartment is arranged between said porous membrane and said membrane having said curvature-adjustable area, and wherein particularly the further lower compartment is arranged between said porous membrane and a bottom of said base element.

Further, according to an embodiment of the present invention, the lens comprises two opposing channels, wherein the lower compartments or the upper compartments of the two electro-osmotic pumps are in fluid communication with the lens volume via both channels.

Further, according to an embodiment of the present invention, (particularly in case the lower compartments are in fluid communication with lens volume via the two channels) said second electro-osmotic pump is in turn configured to pump liquid from the further upper compartment into the further lower compartment and thereby into the lens volume or from the further lower compartment to the further upper compartment and thereby from the lens volume into the reservoir volume depending on a voltage applied to said electrodes of the second osmotic membrane assembly.

Further, according to an embodiment of the present invention, (particularly in case the upper compartments are in fluid communication with lens volume via the two channels) said second electro-osmotic pump is in turn configured to pump liquid from the further lower compartment into the further upper compartment and thereby into the lens volume or from the further upper compartment to the further lower compartment and thereby from the lens volume into the reservoir volume depending on a voltage applied to said electrodes of the second electro-osmotic pump.

Further, according to an embodiment of the present invention, the lens comprises a support structure arranged in each channel for supporting the ring member and/or said membrane.

BRIEF DESCRIPTION OF THE DRAWINGS

The invention will be better understood and objects other than those set forth above will become apparent when consideration is given to the following detailed description thereof. Such description makes reference to the drawings, wherein:

FIG. 4 shows a schematical cross sectional views of an actuator that may be used with the embodiment shown in FIG. 3;

FIG. 15 shows a further embodiment of a lens according to the invention using actuator elements in form of bending Piezo elements;

DETAILED DESCRIPTION

Figure 1:
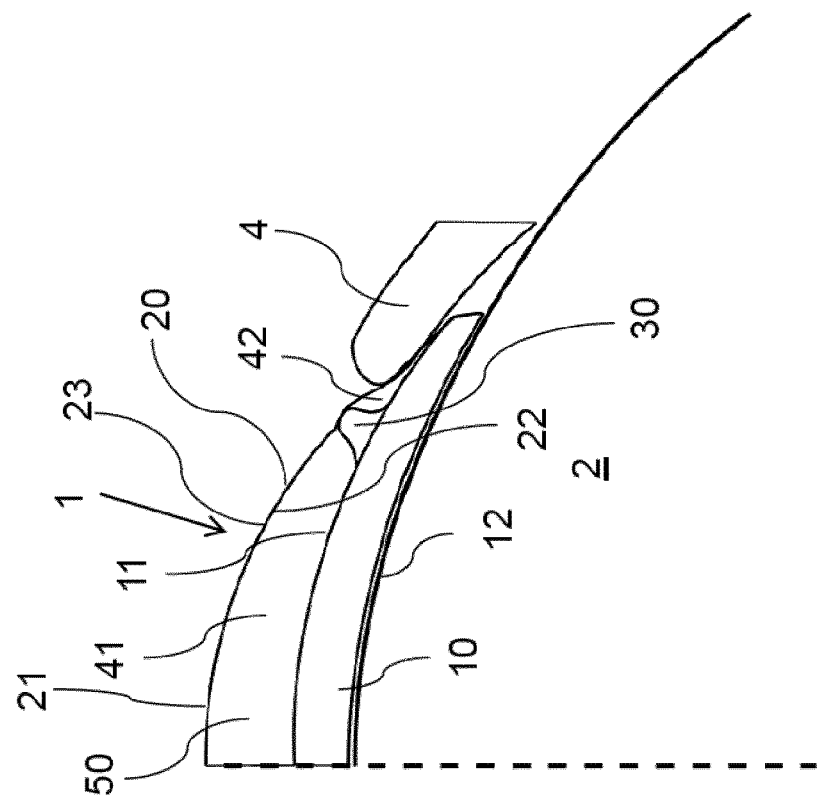
FIGS. 1-2 show that an actuator (e.g. zipper actuator) of a lens according to the invention is influenced by an eyelid of a user of the lens.
Figure 2:
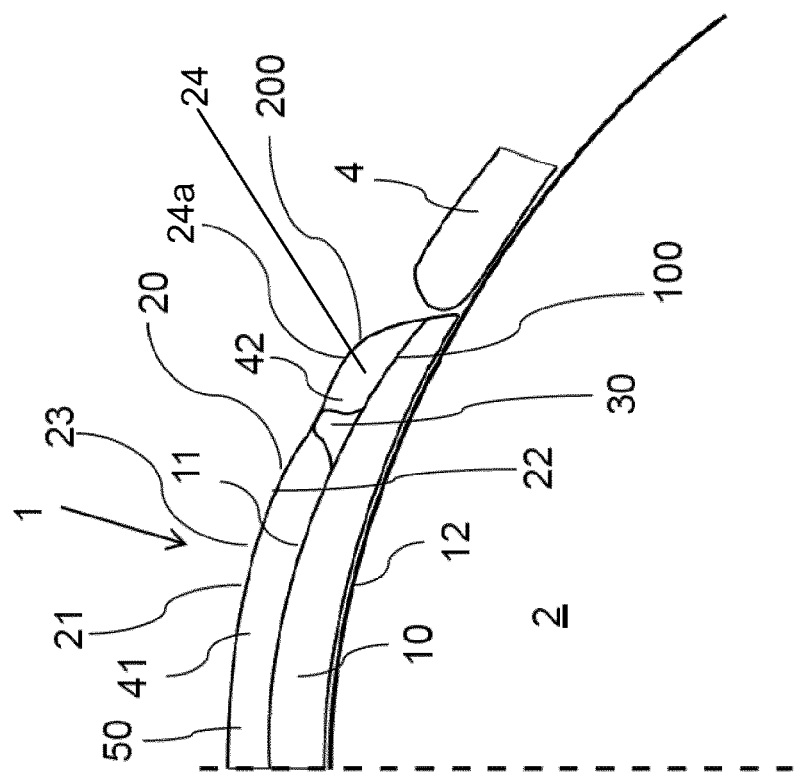

FIGS. 1 and 2 show an embodiment of a contact lens 1 according to the present invention that is designed to be actuated by an actuating means to be described in further detail below. However, the lens 1 may be influenced by an eyelid 4 (e.g. upper and or lower lid) of the person wearing the contact lens on the eye 2 associated to said eyelid due to the fact that the eyelid 4 may temporarily or permanently cover parts of the contact lens 1 upon use of the lens 1 which may exert a pressure on a reservoir volume 42 used for adjusting the focal length of the lens which may interfere with properly adjusting the focal length.

As shown in FIGS. 1 and 2, the contact lens 1 comprises a base element 10 comprising a back side 12 that is adapted to be arranged on a pupil of a person. The base element 10 further comprises a front side 11 facing away from the back side 12 of the base element 10.

Furthermore, a transparent and elastically expandable membrane 20 is connected to said base element 10, wherein said membrane 20 comprises a back side 22 that faces said front side 11 of the base element 10.

For defining the shape of the deflected membrane 20, particularly of a curvature-adjustable (e.g. central) area 23 of the membrane 20, an e.g. circular ring member 30 is provided (also denoted as lens shaper) that is connected to the back side 22 of the membrane 20 and thus defines said (e.g. circular) area 23 of the membrane 20.

Particularly, the ring member 30 extends circumferentially about the optical axis z (indicated by the dashed lines in FIGS. 1 and 2).

Below this area 23, the contact lens 1 comprises a so-called lens volume 41 which is surrounded by the ring member 30. Further, the contact lens 1 comprises a reservoir volume 42 in a boundary region 24 of the lens 1, which reservoir volume may be arranged below a boundary area 24a of said membrane 20. These two volumes 41, 42 of the contact lens 1 are filled with a transparent liquid 50.

To be able to adjust the curvature of the curvature-adjustable area 23 of the membrane 22, which area 23 forms a convex bulge in FIGS. 1 and 2, said volumes 41, 42 are fluidly connected or fluidly connectable to each other such that, when the reservoir volume 42 or a part thereof is compressed or otherwise suitably acted on, liquid 50 residing in the reservoir volume 42 is transferred (e.g. pressed) into the lens volume 41 such that the curvature of said curvature-adjustable area 23 of the membrane 20 increases and the focal length of the contact lens 1 decreases, and wherein, when an actuator means for transferring liquid 50 from the reservoir volume 42 is turned off or its effect reduced, the membrane 20 may—due to its tension—press liquid 50 back into the reservoir volume 42 such that the curvature of said curvature-adjustable area 23 of the membrane 20 decreases and the focal length of the contact lens 1 increases.

As can be inferred from FIG. 1, the reservoir volume 42 is arranged outside of the ring member 30 in a radial direction (i.e. on an outside of the ring member 30) and can be effected by an eyelid 4, when the latter rests on the boundary region 24 top of the reservoir 42 (e.g. on top of area 24a). This may effect an actuator 70 of a pumping means 700 as shown in FIG. 4 since liquid may be squeezed out of the reservoir volume unintentionally by the eyelid 4.

Figure 3:
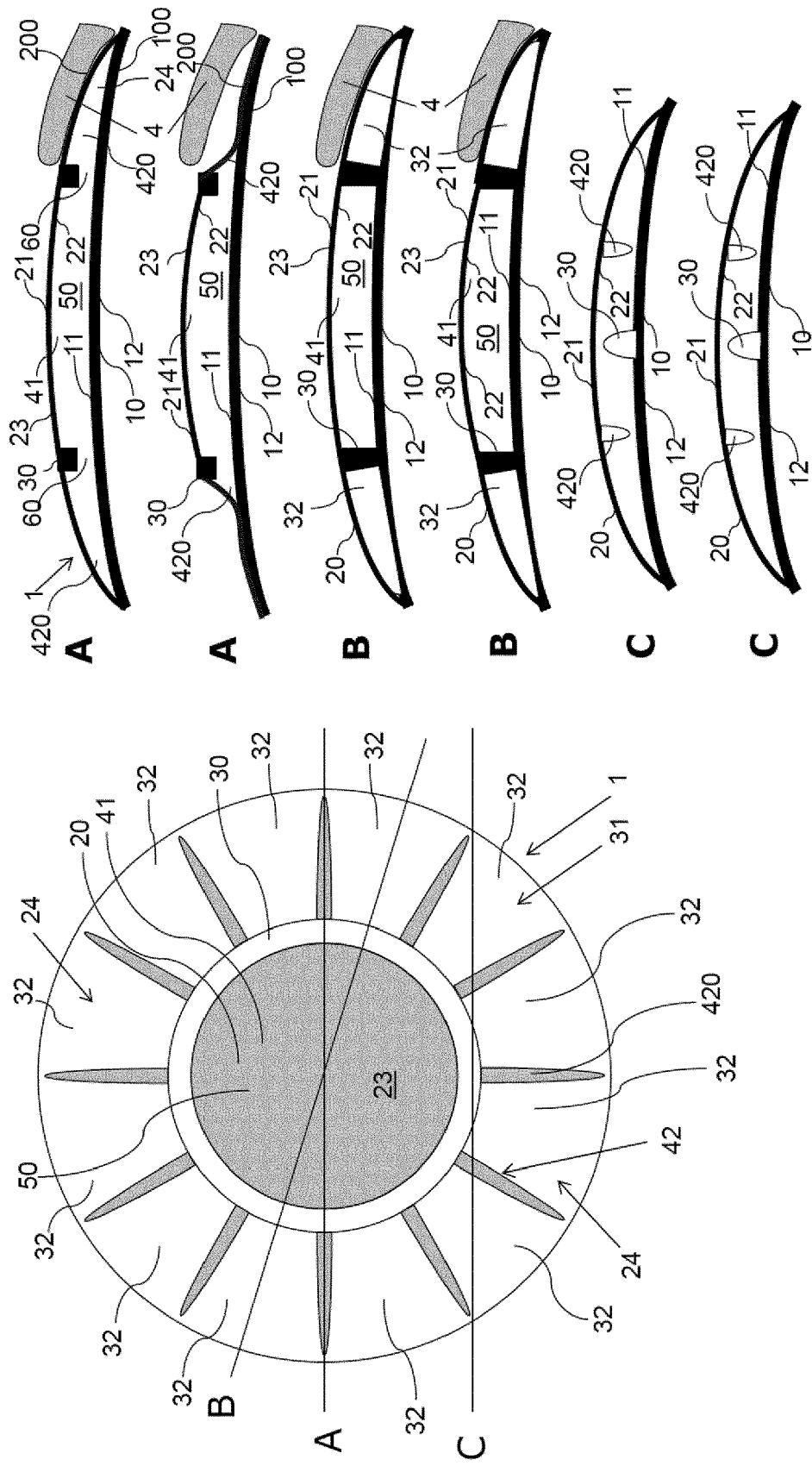
FIG. 3 shows an embodiment of a lens according to the invention that comprises a support structure for protecting the reservoir volume against undue compression because of forces caused by an eyelid of the user.

Therefore, as shown in FIG. 3, to overcome the influence of the eye lid 4 on the tuning of the lens 1, the reservoir volume 42 is split into different sectors 420 and the membrane 20 is supported by a support structure 31 forming a protecting means according to the invention, where the distance between the individual sectors 420 and support features is smaller than the size of the eye lid 4. This prevents the eye lid 4 to influence the focal length of the lens 1 to a large degree. This passive support gives a rigidity to the lens 1, but also prevents the influence of the eye lid 4 on the focal length of the lens 1. Furthermore, this structure also allows for a digital focus power adjustment of the lens by pumping all liquid in an individual sector 420 into the lens volume 41.

In detail, the support structure 31 may be connected to the front side 11 of the base element 10 and comprises a plurality of ridges 32, wherein said ridges 32 divide the reservoir volume 42 into a plurality of separate sectors 420 (i.e. each two neighboring rides 32 enclose a sector 420 which may be covered from above by the membrane 20 that may be connected with its back side 22 to the support structure 31 (e.g. ridges 32).

In order to transfer liquid 50 from the respective sector 420 of the reservoir volume, the lens comprises a pumping means 700 having e.g. an actuator means 70 of the type shown in FIG. 4, which is configured to press liquid 50 from the reservoir volume 42, namely the respective sector 420, into the lens volume 41, in order to adjust the focal length of the lens 1 as described herein.

As indicated in FIG. 4 for a single sector 420, said sectors 420 are each delimited by a first wall or surface 200 formed e.g. by the membrane 20 and a second surface or wall 100 formed by the support structure 31 (or the base element 10), wherein the two wall 200, 100 face each other, and wherein the actuator 70 comprises in each sector 420 a first electrode 71 attached to said first wall 200 and a second electrode 72 insulated by means of an insulation layer 73, which second electrode 72 is attached to said second surface or wall 100 such that an e.g. tapered gap 74 is formed between the two electrodes 71, 72 in each sector 420. Now, in case a voltage is applied by a processing unit 90 (see below) to said electrodes 71, 72 as indicated in FIG. 4 (E denotes the generated electric field) said gap 74 is continuously reduced in a direction M by an amount depending on the magnitude of the applied voltage and liquid 50 is pressed from the respective sector 420 of the reservoir volume 42 into the lens volume 41 which increases the curvature of the curvature-adjustable area 23 of the membrane 20. Preferably, when the voltage applied to the respective pair of electrodes 71, 72 is decreased or turned off, the respective gap 74 opens and a tension of the membrane 20 causes a corresponding amount of liquid 50 to flow back from the lens volume 41 into the reservoir volume 42. The electrodes 71, 72 may be controlled such that the gap 74 is closed at once (adjustment of focal power of the lens 1 in discrete steps) or continuously (continuous adjustment of the focal power of the lens).

The closing of a sections gap 74 is also shown in details A of FIG. 3, which details correspond to cross sections of the lens 1 along the line A in FIG. 3. Here, the upper detail A shows the situation where the voltage is off and the sector 420 or gap has its full volume. The lower detail A shows the situation where the two electrodes 71, 72 are close together and have pushed the liquid 50 out of the respective gap 74/sector 420 through the channels 60 in the ring member 30 into the lens volume 41. Due to the support structure 31 which comprises ridges 32 that are shown in the details B corresponding to cross sections along the line B (again the upper detail B corresponds to "voltage off" and the lower one to "voltage on"), the sectors 420 do not become compressed when the eyelid 4 rests on top of them. Thus the support structure protects the reservoir volume/pumping means 700. Further details C show the cross section along the line C for "voltage off" (upper detail C) and "voltage on" lower detail C in FIG. 3.

Preferably, the electrodes 71, 72 (also 71e below) are deformable without being damaged. Advantageously, the first electrodes are therefore preferably manufactured from one of the following materials:

Carbon nanotubes (see "Self-clearable carbon nanotube electrodes for improved performance of dielectric elastomer actuators", Wei Yuan et al, Proc. SPIE, Vol. 6927, 69270P (2008));

Carbon black (see "Low voltage, highly unable diffraction grating based on dielectric elastomer actuators", M. Aschwanden et al., Proc. SPIE, Vol. 6524, 65241N (2007));

Carbon grease/conducting greases;

Boron-doped diamond coating

Metal ions (Au, Cu, Cr, . . . ) (see "Mechanical properties of electroactive polymer microactuators with ion-implanted electrodes", S. Rosset et al., Proc. SPIE, Vol. 6524, 652410 (2007)); implanted in a polymeric material Liquid metals (e.g. Galinstan);

Metallic powders, in particular metallic nanoparticles/nanowires (Gold, silver, copper, platinum, etc.);

Metal films

Figure 17:
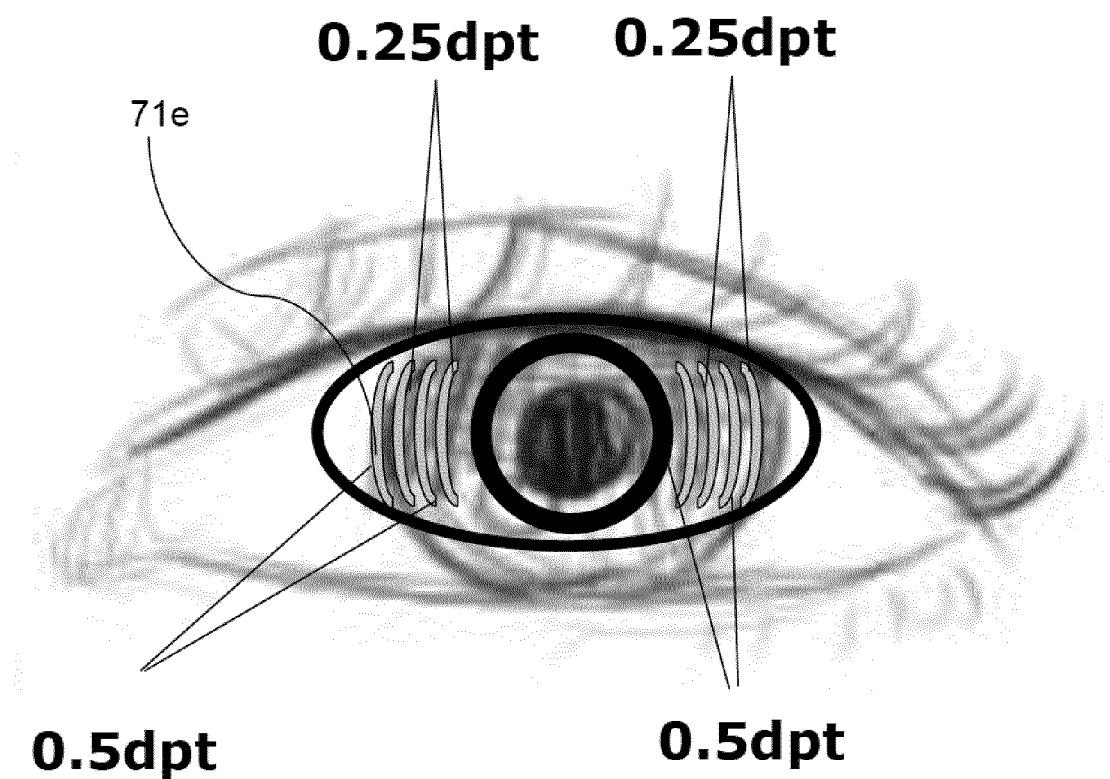
FIG. 17 shows a further embodiment of a lens according to the invention that allows to change the focal power of the lens by discrete amounts.

Conducting polymers (intrinsically conducting or composites);

The electrodes 71 and 72 may be deposited by means of any of the following techniques:

Spraying;

Ion-implantation (see "Mechanical properties of electroactive polymer microactuators with ion-implanted electrodes", S. Rosset, Proc. SPIE, Vol. 6524, 652410 (2007));

PVD, CVD;

Evaporation;

Sputtering;

Photolithography;

Printing, in particular contact printing, inkjet printing, laser printing, and screen printing;

self-assembly (see e.g. "Local surface charges direct the deposition of carbon nanotubes and fullerenes into nanoscale patterns", L. Seemann, A. Stemmer, and N. Naujoks, Nano Letters 7, 10, 3007-3012, 2007);

Brushing;

Electrode plating;

Further, to control a stiction behavior of the membrane 20 and the base element 10 the following coatings can be applied to the membrane 20, base element 10, electrodes 71, 72 or insulation layer 73:

Self assembled monolayer
Teflon
Perfluorocarbons.
The self assembled monolayer (SAM) can, e.g., comprise molecules with molecule tail groups comprising or consisting of regular or perfluorinated alkyl chains and/ormolecule head groups comprising or consisting of silane or phosphoric acid.
Surface roughness adjustment by nano-structuring.
Further, the insulation layer 73 can, e.g., comprise or consist of:
$Al_2O_3$, $SiO_2$, $Si_3N_4$
Parylene
Epoxy, PVDF (Poly Vinylidene diFluoride)
Electric resins: SU-8, Cyclotene (BCB based),
High-k dielectrics such as $TiO_2$, $HfO_2$ or $ZrO_2$
Nanocomposites consisting of high-k nanoparticles (such as $BaTiO_3$) in a polymer matrix.
Polymers
Plastic
Furthermore, the insulation layer 73 can, e.g., be deposited by means of any of the following techniques:
PVD (Evaporation, sputtering)
CVD (ALD, PECVD, . . . )
Spin-coating
Anodization
Spray pyrolysis Further, FIG. 17 shows a discrete operation of the pumping means as mentioned above by means of an actuator 70 having first electrodes 71e and corresponding second electrodes (not shown since covered by the first electrodes) forming pairs of electrodes (e.g. arranged on either side of the central lens volume 41) so that a discrete change in curvature of the membrane 20 can be achieved by actuating such actuator segments or electrode pairs individually as described above (e.g. 71e in FIG. 17). It is for example possible to avoid a continuous adjustment of the actuator by fully closing or opening individual actuator segments. Closing one actuator segment 71e results in a refractive power change of 0.25 dpt or 0.5 dpt. By powering different combinations of actuator segments a broad range of focal power combinations are achievable. These discrete changes may be triggered by a certain movement pattern (e.g. of the eyelid 4 of the user or the deformation of the crystalline lens of the person wearing the lens) that can be processed accordingly by the processing unit 90 described further below.

Figure 5:
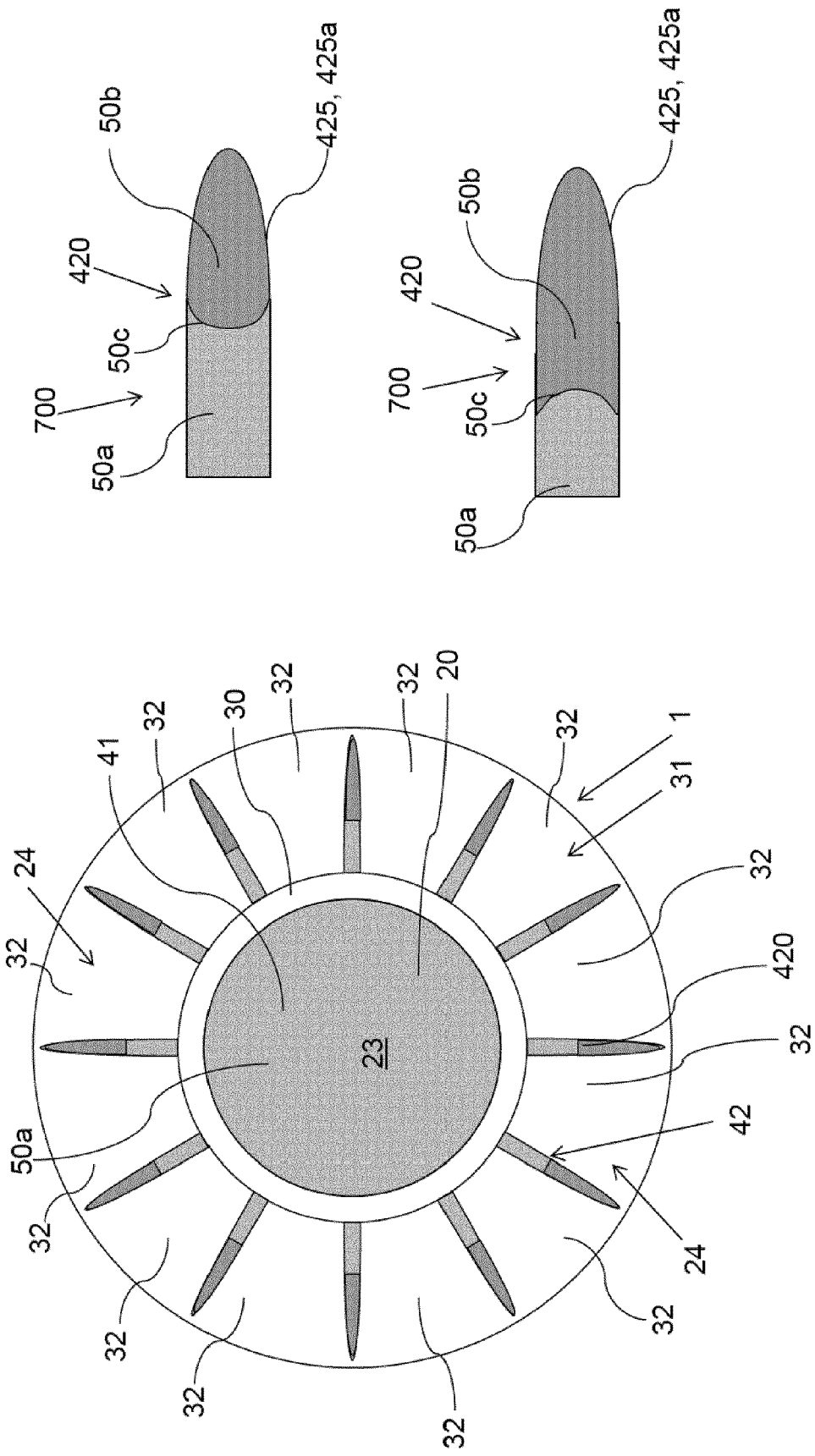
FIG. 5 shows a further embodiment of a contact lens according to the present invention comprising a support structure and a pumping means utilizing a hydrophobic and a hydrophilic liquid.

FIG. 5 shows a further way of transferring liquid from the reservoir volume 42 to the lens volume 41. In contrast to FIG. 3, the lens volume 41 is now filled with a transparent hydrophobic liquid 50a, and wherein the liquid residing in the reservoir volume 42 is a hydrophilic liquid 50b such that in each sector 420 an interface 50c is formed between the hydrophilic liquid 50a and the hydrophobic liquid 50b.

Here, the pumping means 700 is configured to apply a voltage between the hydrophilic liquid 50b residing in the respective sector 420 and a surrounding electrode embedded in the wall 425 and electrically insulated towards the hydrophilic liquid 50b and enclosing the respective sector 420 such that the respective interface 50c is moved towards the lens volume 41 thus pushing hydrophobic liquid 50a into the lens volume 41 such that the curvature of said curvature-adjustable area 23 of the membrane 20 increases and the focal length of the lens decreases, wherein when said voltage is decreased or turned off, a tension of the membrane 20 causes a corresponding amount of hydrophobic liquid 50a to flow back from the lens volume 41 into the reservoir volume 42.

Figure 6:
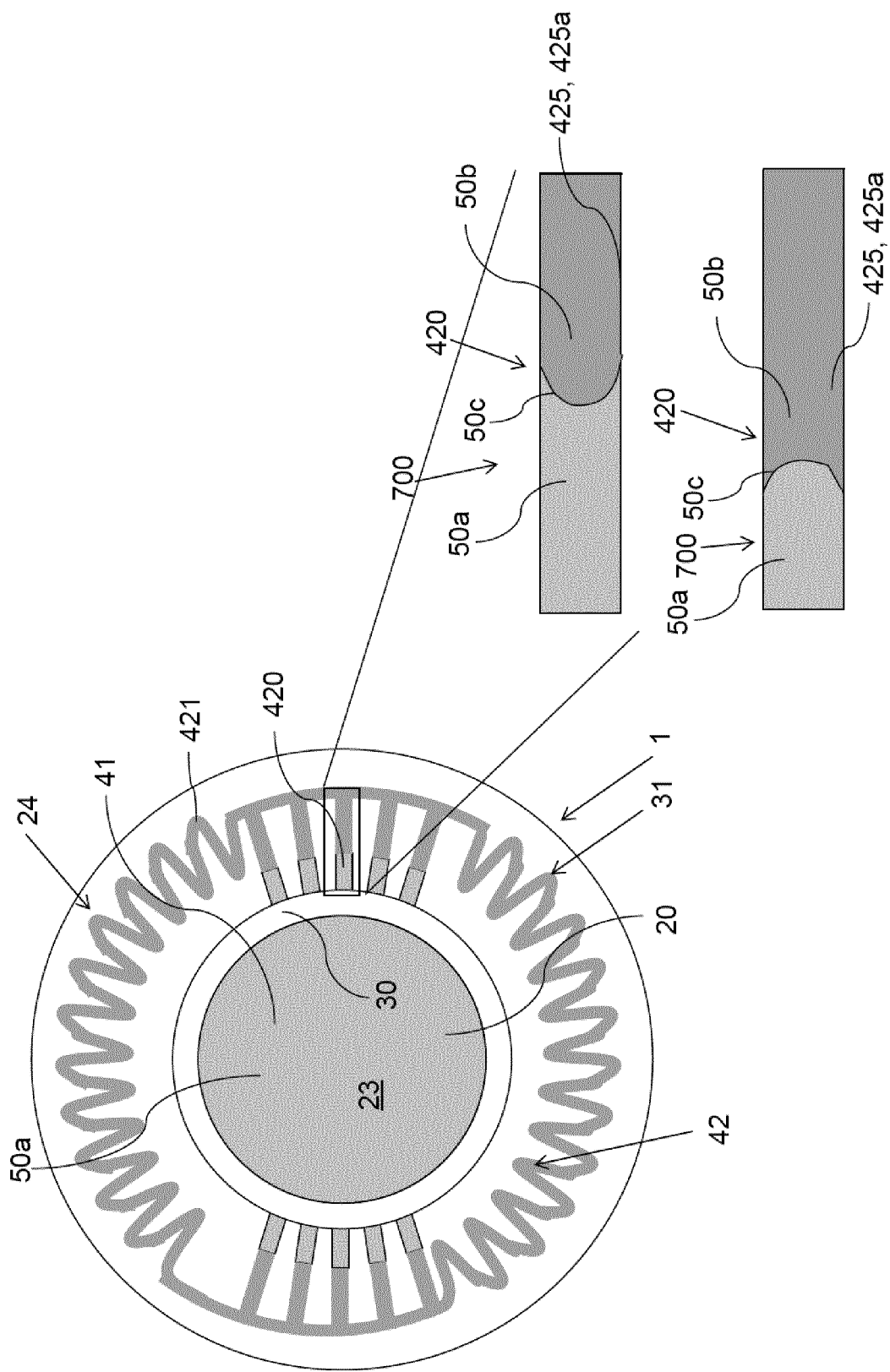
FIG. 6 shows a further embodiment of a contact lens according to the present invention comprising a support structure and pumping means utilizing a hydrophobic and a hydrophilic liquid.

FIG. 6 shows a variant of the embodiment shown in FIG. 5, wherein now in contrast to FIG. 5, the reservoir volume 42 comprises a circumferential reservoir section 421 which extends circumferentially along the lens volume 41 further outwards in a radial direction R of the lens 1 and is connected to the lens volume 41 via said sectors 420. The sectors 420 and the reservoir section 421 are preferably embedded into a support structure 31 that prevents compression of the reservoir volume 21 by means of an eyelid 4 of the user of the lens 1. As shown in FIG. 6, the reservoir section 421 may comprise a meandering shape at least in sections.

Figure 7:
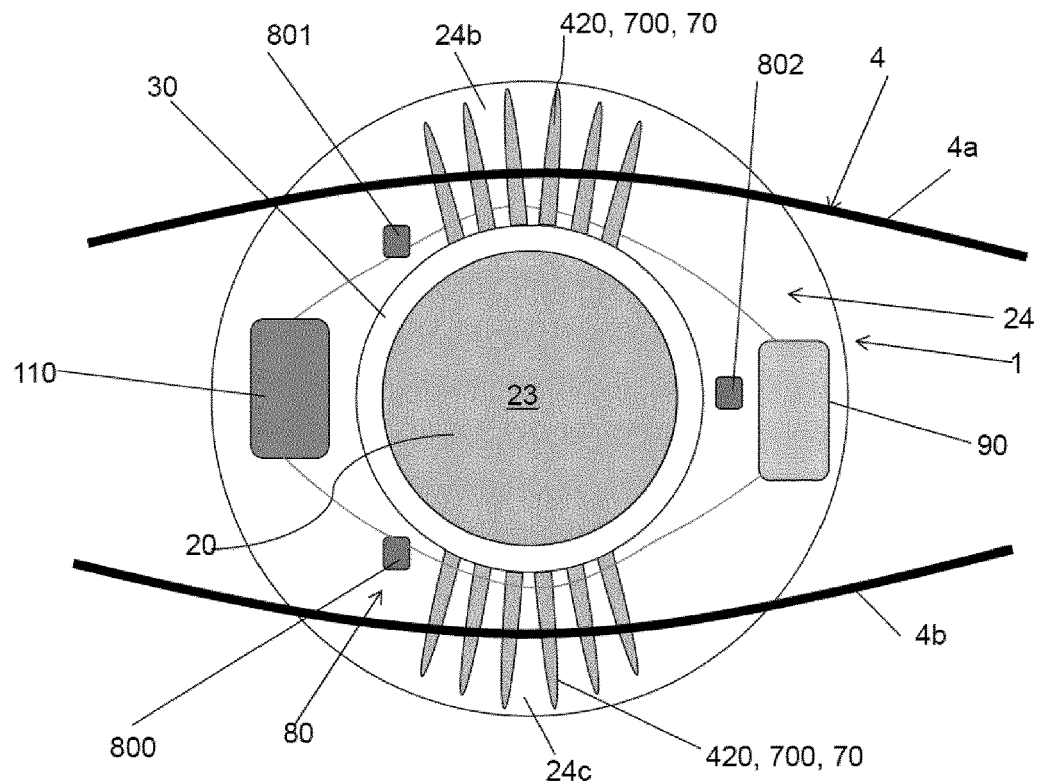
FIG. 7 shows a further embodiment of a lens according to the invention.

Furthermore, FIG. 7 shows an embodiment of the present invention of the type showing in FIG. 3, wherein in contrast to FIG. 3 the lens 1 now comprises a first group of neighboring sectors 420 that are arranged in a first portion 24b of the boundary region 24 of the lens 1 and a second group of neighboring sectors 420 which are arranged in an opposing second portion 24c of said boundary region 24 of the lens, wherein, when the lens 1 is attached to the surface of the eye of the user, the upper lid 4a of the eyelid 4 of the user rests on said first portion 24b of the boundary region 24 and at least partially covers the first group of sectors 420 while the lower lid 4b rests on said second portion 24c of said boundary region 24 and at least partially covers the second group of sectors 420 when the eye is in an open position. The remaining boundary region 24 between the first and the second portion 24b, 24c is preferably free of sectors 420 in order to provide space for an electric energy source 110 (e.g. battery) and a controller 90, as well as a sensor means 80. The sensor means 80 comprises three sensors 800, 801, 802, wherein each of these sensors comprises a light source (e.g. LED) and a photosensitive element (e.g. photodiode).

Preferably, these three sensors 800, 801, 802 are configured to emit light by means of the respective light source and to detect emitted light by means of the respective photosensitive element that has been scattered back by the eye or eyelid or crystalline lens of the user.

As shown in FIG. 7, these three sensors 800, 801, 802 are preferably arranged on the corners of a virtual triangle.

Further, said sensor means 80, said battery 110 and said processing unit 90 are arranged in a region of the lens 1 that is not covered by the upper and lower lid 4a 4b when the eye is in the open position, wherein particularly the energy source 110 and the processing unit 90 are arranged on opposing sides of the lens volume 41 and wherein said three sensors 800, 801, 802 of the sensor means 80 are arranged around the lens volume 41 on the corners of said virtual triangle, wherein one sensor 802 is arranged on a centerline of the lens besides the lens volume 41, and wherein one of the remaining two sensors 801 is arranged closer to the upper lid 4a and the other sensor 800 of the remaining two sensors 800, 801 is arranged closer to the lower lid 4b (related to an open position of the eye and a lens 1 being attached to the surface of the eye).

Figure 8:
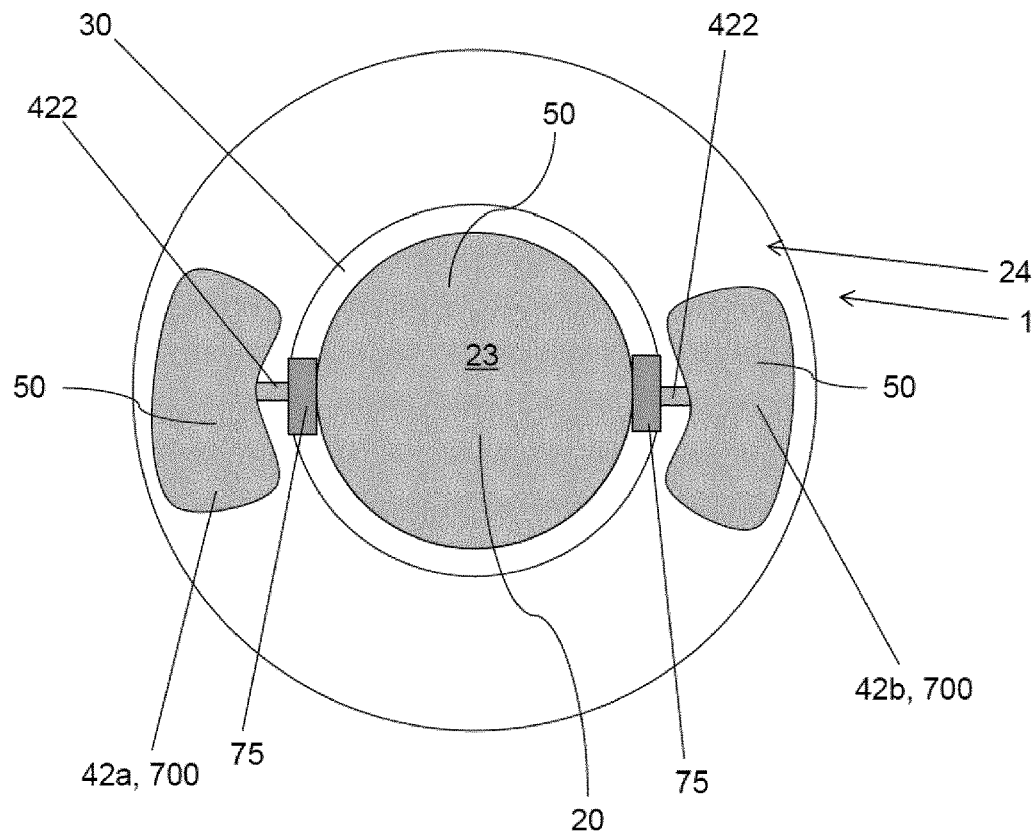
FIG. 8 shows a further embodiment of a lens according to the invention comprising a reservoir volume with a pumping means and a valve.

Further, FIG. 8 shows an embodiment of a lens 1 according to the invention comprising a reservoir volume 42 comprising two separate chambers 42a and 42b which are arranged on opposing sides of the lens 1, so that the lens volume 41 is arranged between these two chambers 42a, 42b. Further, the chambers 42a, 42b each comprise a pumping means 700 for pumping liquid 50 into the lens volume 41 via a reservoir channel 422, respectively, in order to adjust the focal length of the lens 1 as described herein.

In order to separate the lens volume 41 from the respective chamber 42a, 42b (e.g. so as to prevent backflow of the transferred liquid into the chambers 42a, 42b due to the tension of the membrane 20, each reservoir channel 42 comprises a valve 75 (e.g. as described herein). By means of these valves the liquid flow between the reservoir volume and the lens volume can be blocked so that these valves 75 also form a protecting means according to the invention.

Figure 9:
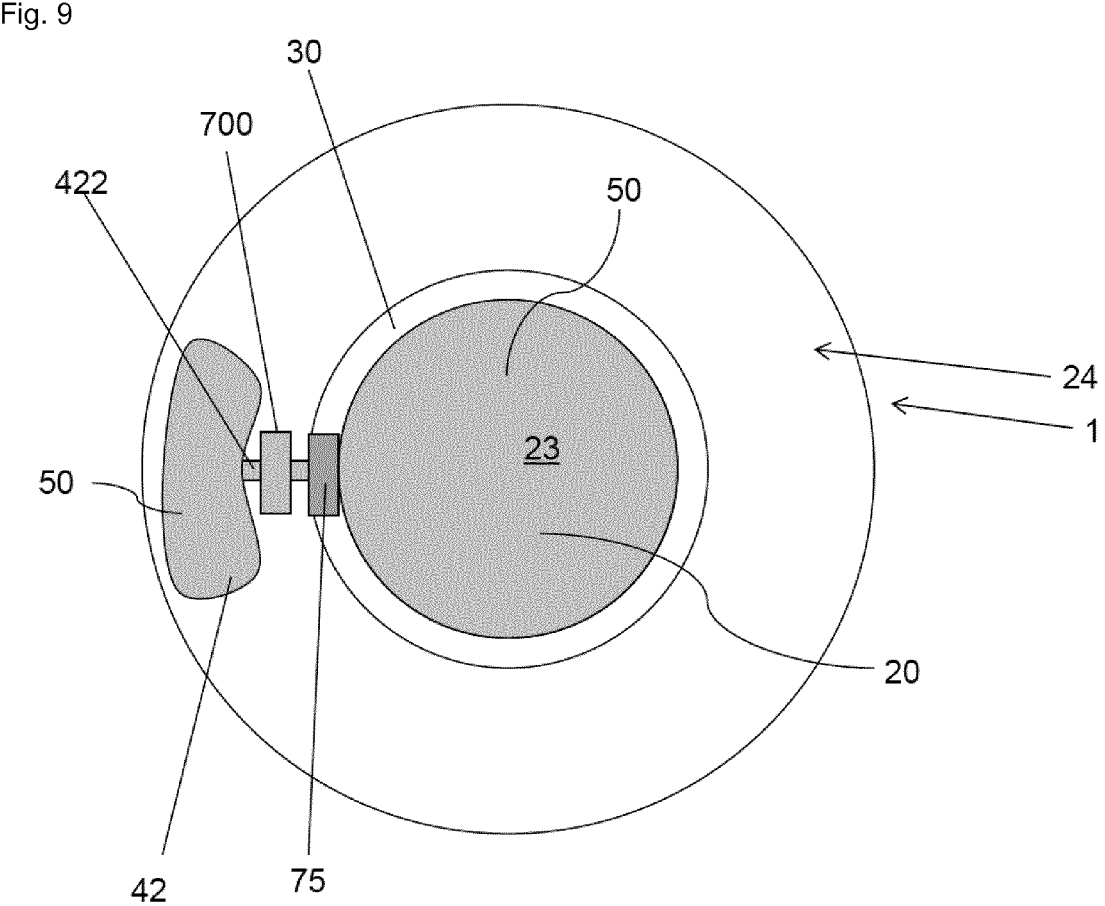
FIG. 9 shows a further embodiment of a lens according to the invention comprising a pumping means and a valve.

In this context, FIG. 9 shows a modification of the embodiment shown in FIG. 8, wherein now the lens 1 comprises a single chamber or reservoir volume 42 and both, the pumping means 700 and the valve 75 forming a protecting means according to the invention are arranged in the reservoir channel 422 that connects the reservoir volume with the lens volume 41.

Figure 10:
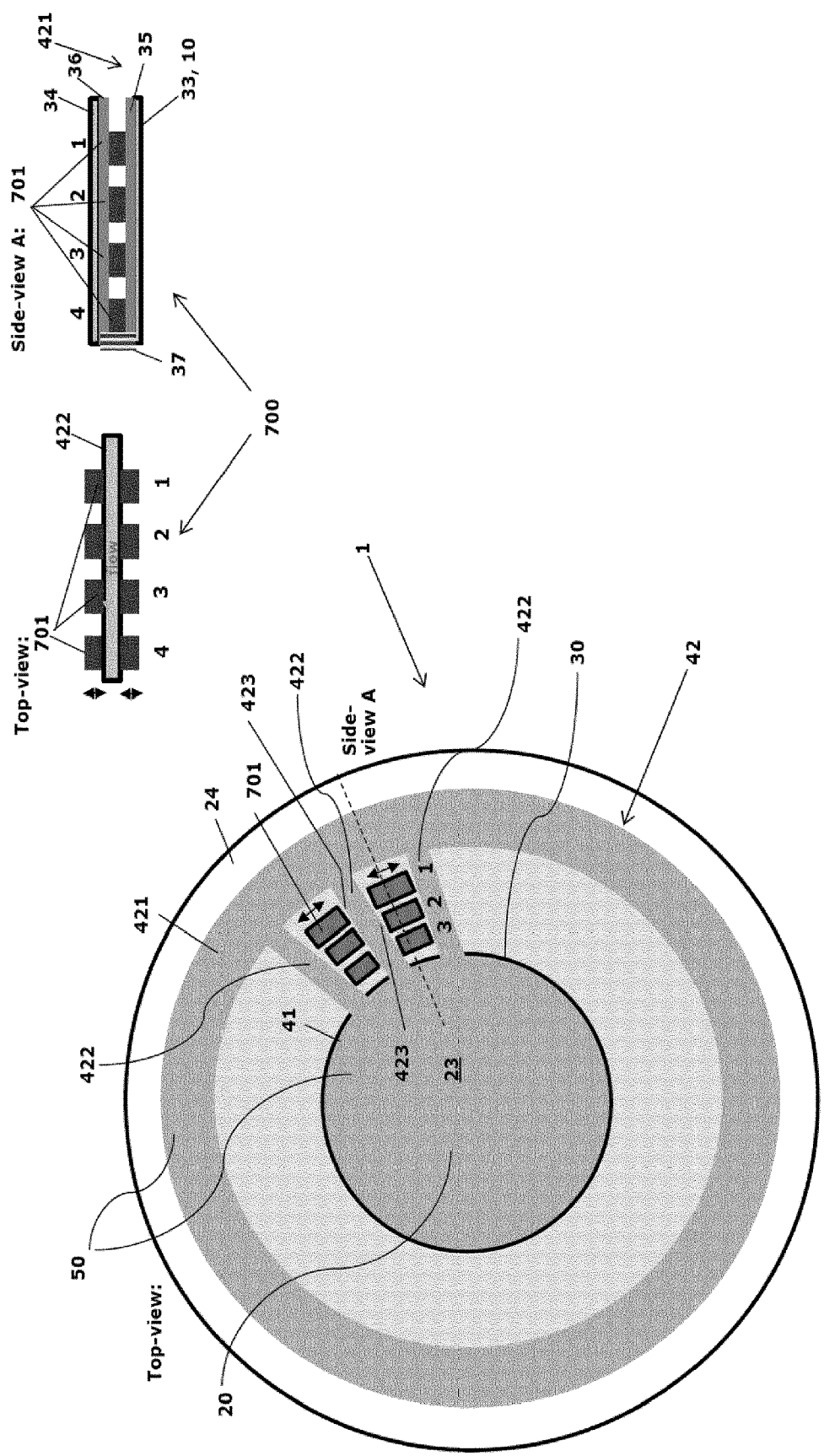
FIG. 10 shows a further embodiment of a lens according to the invention using actuator elements in form of Piezo elements.

FIG. 10 shows a further embodiment of a lens 1 according to the invention, wherein the lens 1 comprises at least one reservoir channel 422 forming part of the reservoir volume 42, via which reservoir channel 422 the reservoir volume 42, namely a circumferential reservoir section 421, can be fluidly connected to the lens volume 41.

For transferring liquid 50 from the reservoir volume 42 to the lens volume 41, the lens 1 comprises a plurality of actuator elements 701 in the form of Piezo elements 701 which are arranged along the at least one reservoir channel 422 on both sides of the latter and are each configured to press laterally (e.g. in the extension plane of the base element 10 or membrane 20 against an associated deformable lateral wall (e.g. a soft membrane) 423 of the at least one reservoir channel 422 so as to push liquid 50 from the reservoir volume 42 into the lens volume 41.

In order to protect the reservoir volume 42 from loads exerted onto the reservoir volume (particularly onto the circumferential section 421) by eyelids of the user wearing the lens 1, the lens 1 comprises a protecting means in form of a support structure that comprises a rigid top 34 (to which the membrane 20 may be connected) covering the reservoir volume 42 at least in sections from above as well as a rigid bottom 33 (e.g. formed by the base element 10 of the lens 1 covering the reservoir volume 42 from below). The actuator elements 701 may each be connected to the rigid bottom 33 as well as to the rigid top 34 via a deformable material layer 35, 36, respectively, which material layers are softer than the rigid top 34 and the rigid bottom 33.

Further, in an embodiment of the present invention, the rigid top 34 is supported on the rigid bottom 33 via at least one post 37 comprised by said support structure, wherein the at least one post 37 extends between the rigid top 34 and the rigid bottom 33.

Preferably, the actuator elements 701 of the pumping means 700 that are arranged along the at least one reservoir channel 422 on both sides of the channel 422 are actuated in a successive fashion so as to press liquid from the reservoir volume 42 into the lens volume 41.

Figure 11:
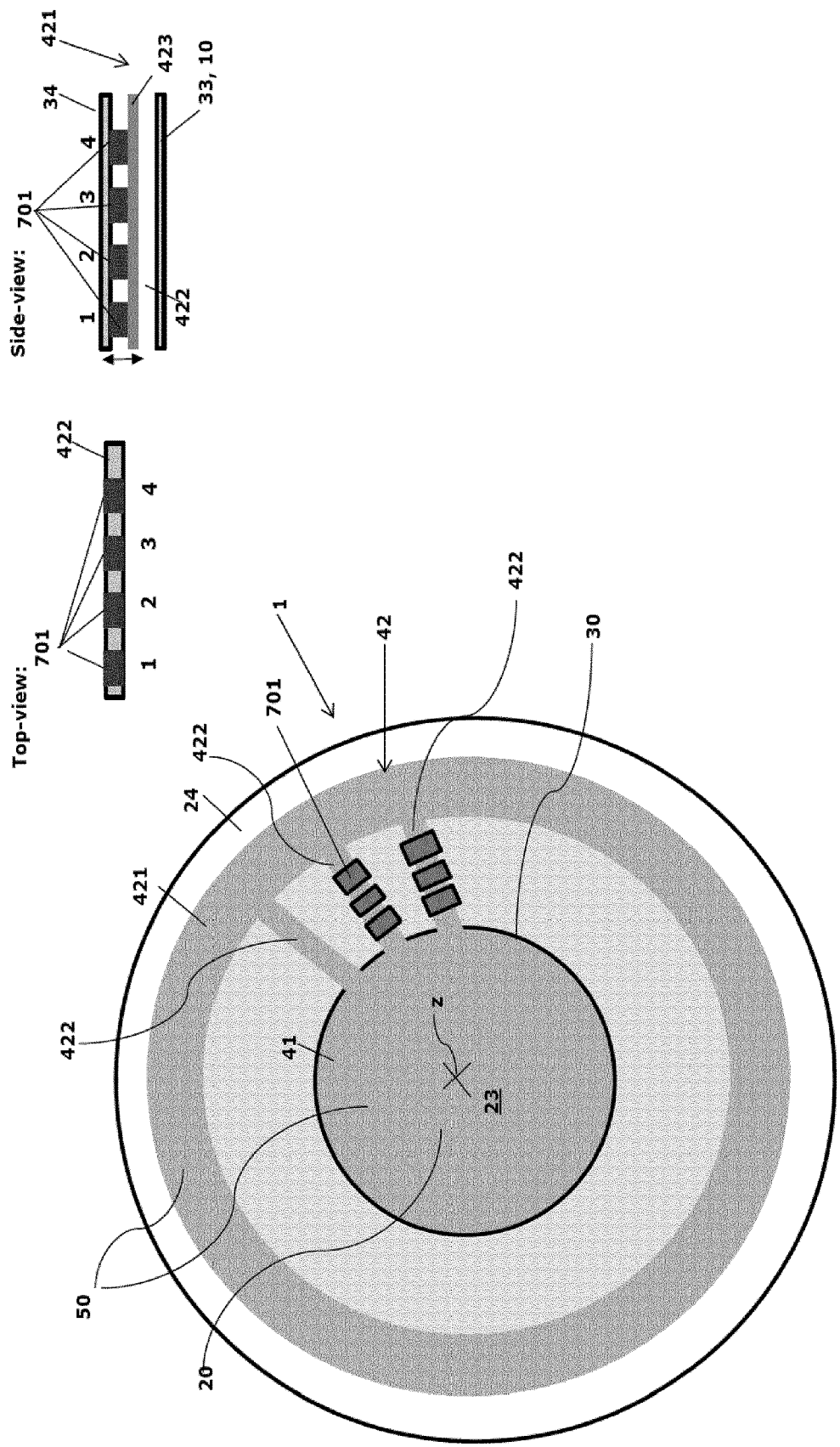
FIG. 11 shows a variant of the embodiment shown in FIG. 10.

FIG. 11 shows a variant of the embodiment shown in FIG. 10, wherein in contrast to FIG. 10 the actuator elements (e.g. Piezo elements) 701 are connected to the rigid top 34 of the support structure and are arranged between said rigid top 34 and a deformable wall 423 (e.g. deformable ceiling, particularly soft membrane) of the at least one reservoir channel 422 on a side of the deformable wall 423 facing away from the base element 10. Here, the actuator elements 701 are connected to the deformable wall 423 of the at least one channel 422 and are configured to press against the deformable wall 423 of the at least one reservoir channel 422 so as to e.g. compress the at least one reservoir channel from above and to press liquid from the reservoir volume 422 into the lens volume 41. Further, the deformable wall or ceiling 423 faces the base element 10 in a direction parallel to the optical axis z of the lens 1.

Figure 12:
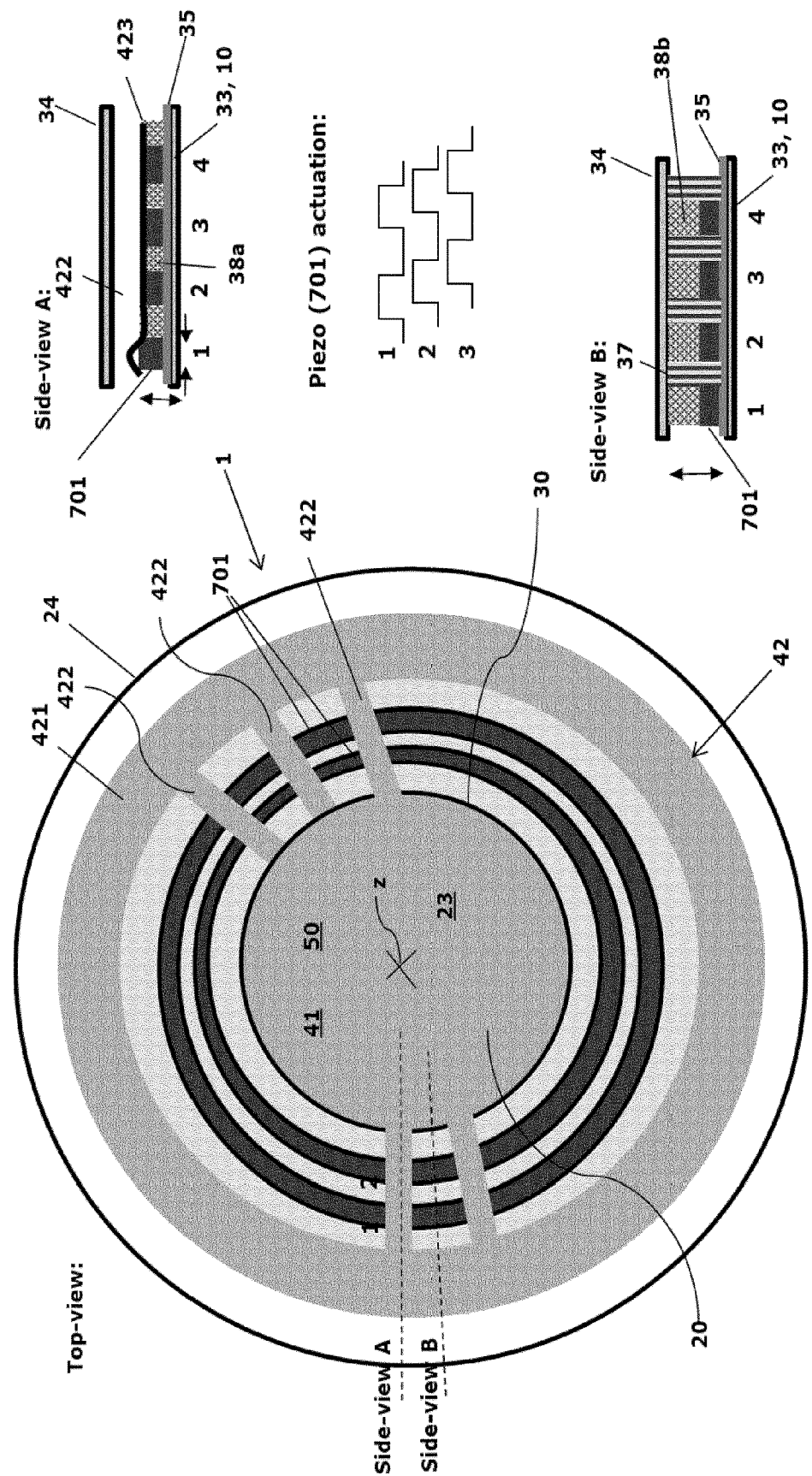
FIG. 12 shows a further embodiment of a lens according to the invention using actuator elements in form of ring-shaped Piezo elements.

In yet another embodiment shown in FIG. 12, the actuator elements 701 are formed as ring-shaped (or cylinder-shaped) Piezo elements 701 which are coaxially arranged around the lens volume 41 with respect to the optical axis z of the lens 1. Here, the Piezo elements 701 are arranged radially further out than an outermost edge of the lens volume, while the circumferential reservoir section 421 is arranged radially further out than the outermost Piezo element 701, while the at least one reservoir channel 422 extends from the reservoir section 421 to the lens volume and crosses the Piezo elements 701.

Particularly, in FIG. 12, said actuator elements 701 are configured to expand in an axial direction coinciding with said optical axis z of the lens 1 when being actuated, such that said actuator elements 701 press against a deformable wall (e.g. bottom) 423 of the at least one reservoir channel 422 from below so as to push liquid from the reservoir volume 422 into the lens volume 41.

Also here, the support structure of the lens 1 comprises a rigid top 34 covering the reservoir volume 42 at least in sections from above as well as a rigid bottom 33 (e.g. formed by the base element 10 of the lens covering the reservoir volume 42 from below). The actuator elements 701 are now each connected to the rigid bottom 33 via a deformable material layer 35 that is softer than the rigid top 34 and the rigid bottom 33 and are arranged between said rigid bottom 33 and the deformable wall (e.g. bottom) 423 of the at least one reservoir channel 422. Further, between each two neighboring actuator elements a deformable material (e.g. a soft polymer) 38a may be arranged below the at least one reservoir channel 422.

Particularly, as indicated in FIG. 12 (this may also be done in FIGS. 10 and 11) the actuator elements (e.g. Piezo elements) 701 may each be actuated by means of a square wave voltage, wherein the square wave voltages all comprise a phase shift with respect to one another such that the actuator elements 701 expand from the outside inwards in succession, so as to press against the deformable wall 423 of the respective reservoir channel 422 and to thereby press liquid from the reservoir volume 422 towards the lens volume 41.

As further shown in FIG. 12, the rigid top 34 may be supported on the rigid bottom 33 of the lens 1 via at least one post 37 comprised by said support structure, wherein said at least one post 37 preferably extends between the rigid top 34 and the rigid bottom 33 and is preferably arranged between neighboring actuator elements 701 outside the respective channel 422.

Further, also outside the at least one reservoir channel 422, a deformable material 38b (e.g. a soft polymer) may be arranged between the actuator elements 701 and the rigid top 34.

Figure 13:
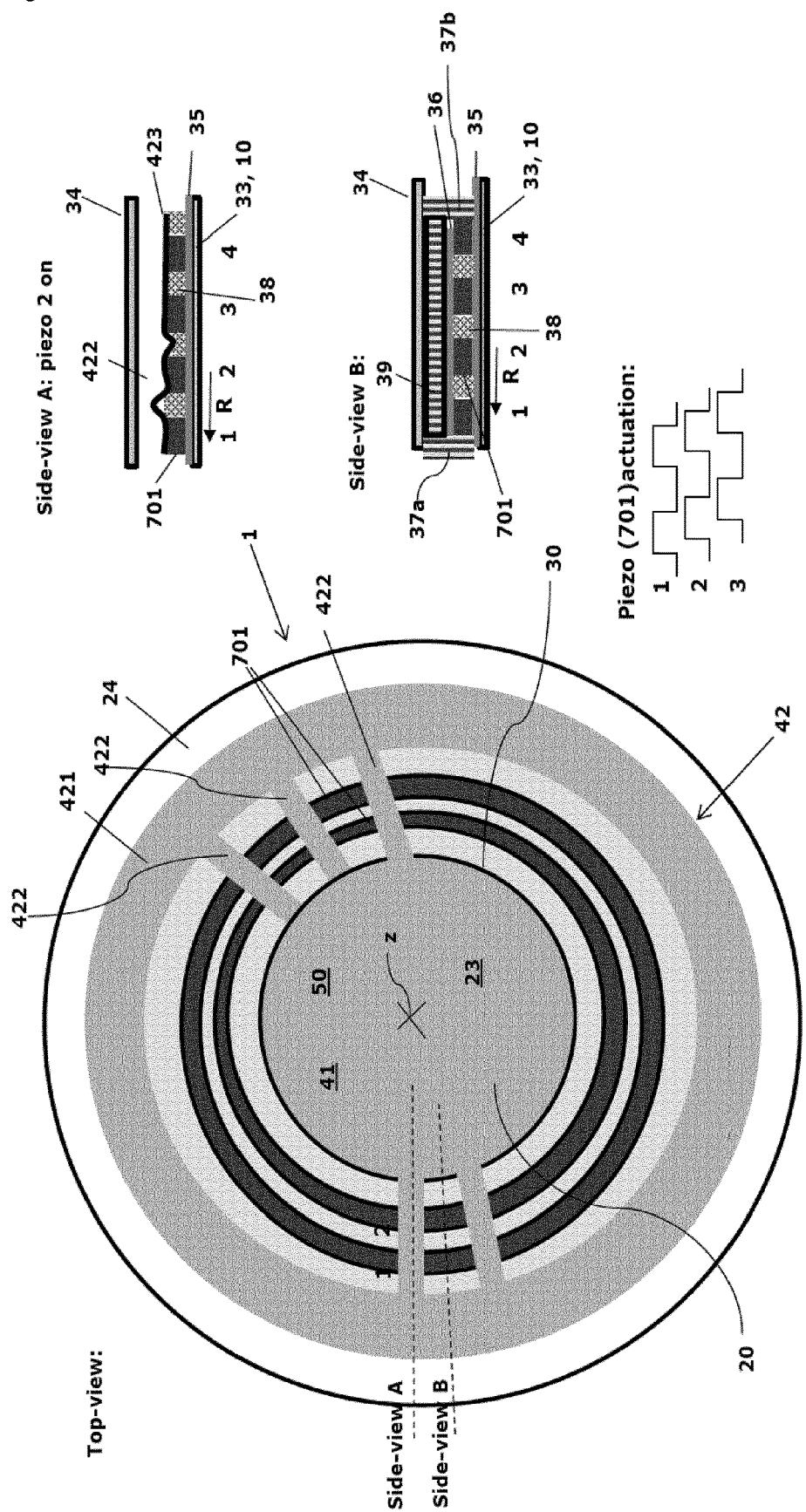
FIG. 13 shows a variant of the embodiment shown in FIG. 12.

FIG. 13 shows a modification of the embodiment shown in FIG. 12, wherein now said ring-shaped Piezo elements 701 are configured to expand in a radial direction R running perpendicular to said optical axis z (namely inwards towards the lens volume 41) when being actuated, such that said actuator elements 701 deform a deformable wall (e.g bottom) 423 of the at least one reservoir channel 422 so as to push liquid from the reservoir volume 422 into the lens volume 41. This is possible since due to the movement of the Piezo elements 701 said deformable wall 423 may form bulges that travel towards the lens volume 41 thus pushing the liquid 50 into the lens volume 41.

Again, the support structure of the lens 1 may comprise a rigid top 34 covering the reservoir volume 42 at least in sections from above as well as a rigid bottom (e.g. formed by base element 10 of the lens 1) 33, wherein the actuator elements 701 may each be connected to the rigid bottom 33 via a deformable material layer 35 that is softer than the rigid top 34 and the rigid bottom 33, and are arranged between said rigid bottom 33 and the deformable wall (e.g. bottom) 423 of the at least one reservoir channel 422. Further, between neighboring actuator elements 701 a deformable material (e.g. a soft polymer) 38 may be arranged.

Particularly, said ring-shaped actuator elements (e.g. Piezo elements) 701 may again each be actuated by means of a square wave voltage as indicated in FIG. 13, wherein the square wave voltages comprise a phase shift such that the Piezo elements 701 expand from the outside inwards in succession, so as to deform the deformable wall 423 of the respective reservoir channel 422 and to thereby press liquid from the reservoir volume 422 towards the lens volume 41.

Further, as shown in FIG. 13 the rigid top 34 may be supported on the rigid bottom 33 via at least one post 37a, 37b comprised by said support structure, wherein said at least one post preferably extends between the rigid top 34 and the rigid bottom 33. In detail, an inner post 37a may be arranged in the radial direction R within the innermost ring-shaped actuator element 701 while an outer post 37b may be arranged in the radial direction outside of the outermost ring-shaped actuator element 701.

Further, outside the at least one reservoir channel 422, the ring-shaped actuator elements 701 may be connected to the rigid top 34 via a deformable material layer 36 that may be connected to a rigid element 39 forming part of the support structure, which rigid element 39 may in turn be connected to said rigid top 34.

Figure 14:
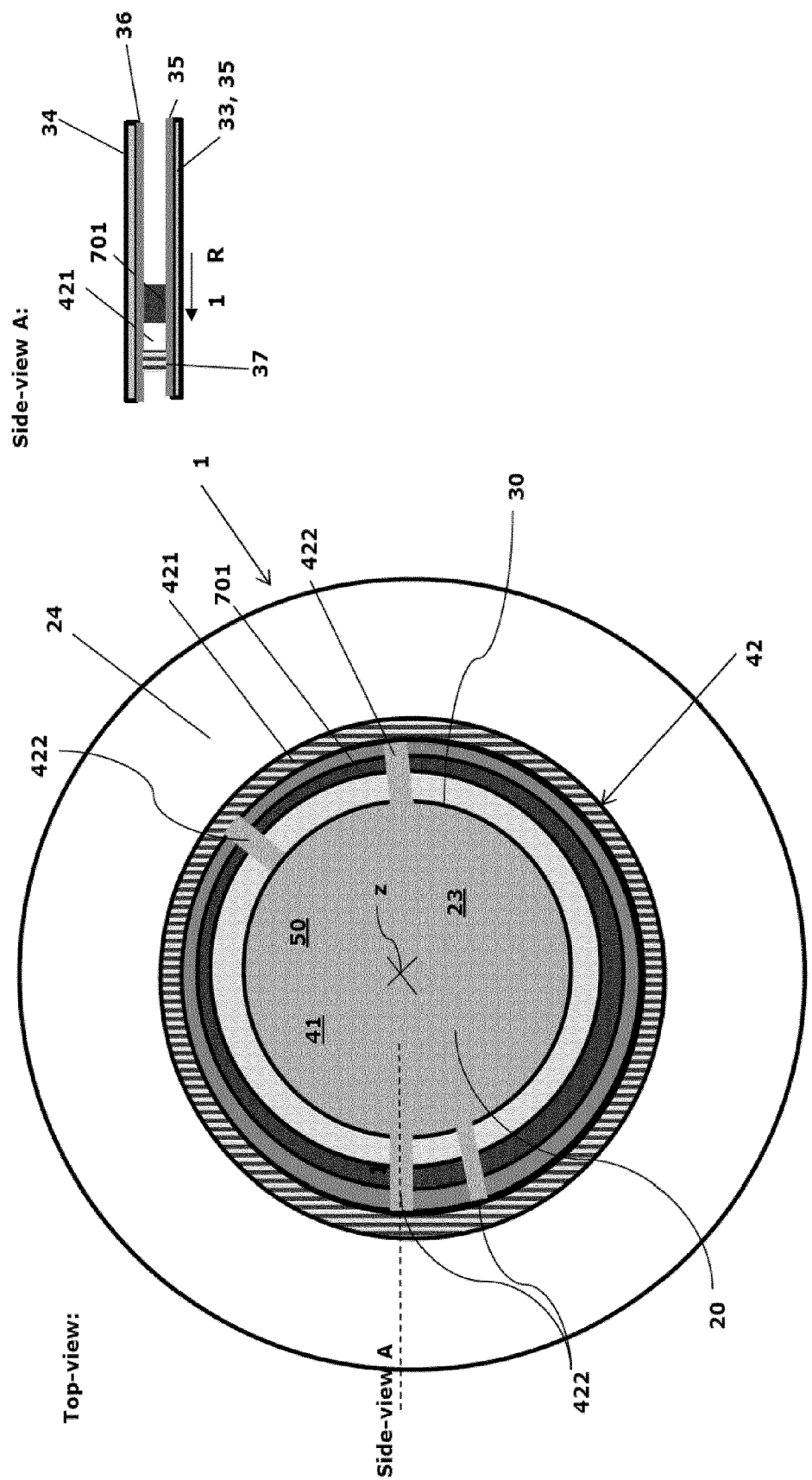
FIG. 14 shows a further embodiment of a lens according to the invention using a single actuator element in form of ring-shaped Piezo element.

FIG. 14 shows a further embodiment having a ring-shaped actuator element 701 for driving the pumping means 700, wherein here, a single ring-shaped actuator element 701, preferably in the form of a Piezo element 701, is used, which is configured to be actuated such that liquid residing in the reservoir volume 42 is pressed into the lens volume 41, wherein said actuator element 701 is configured to expand outwards in a radial direction R running perpendicular to the optical axis z of the lens 1 when being actuated, such that said actuator element 701 compresses a circumferential reservoir section 421 of the reservoir volume 42, which circumferential reservoir section 421 is fluidly connected to the lens volume 41 via at least one reservoir channel 422, so as to push liquid from the reservoir volume 42 into the lens volume 41.

Here, the support structure may comprise a rigid top 34 covering the reservoir volume 42 (e.g. the circumferential reservoir section 422 and at least parts of the at least one reservoir channel 422) at least in sections from above as well as a rigid bottom 33 (e.g. formed by the base element 10 of the lens 1 covering the reservoir volume 42 from below), wherein the ring-shaped actuator element 701 may be connected to the rigid bottom 33 and the rigid top 34 via a deformable material layer 35, 36, respectively, which layers 35, 36 are softer than the rigid top 34 and the rigid bottom 33.

Further, the rigid top 34 is supported on the rigid bottom 33 via at least one post 37 comprised by said support structure, wherein said at least one post 37 may be arranged in the radial direction outside of the actuator element 701 and may form an (e.g. circumferential) lateral outer wall 37 of the circumferential reservoir section 421.

Figure 16:
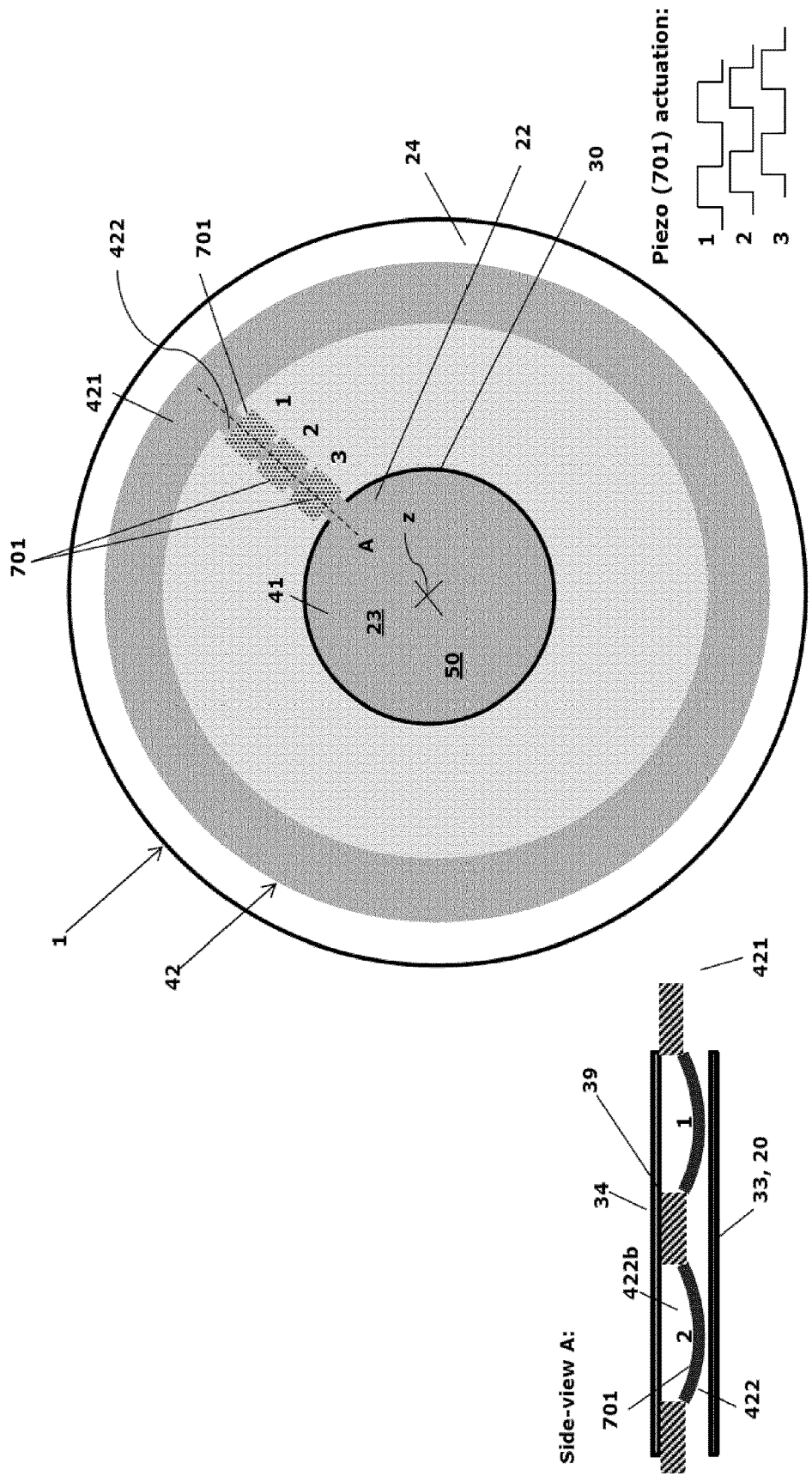
FIG. 16 shows a variant of the embodiment shown in FIG. 15.

Furthermore, FIGS. 15 and 16 show embodiments of the lens 1 according to the invention using pumping means 700 that comprise bending actuator elements 701.

Particularly, according to FIG. 15, these bending actuator elements 701 are arranged above separate chambers 426 of the reservoir volume which chambers 426 are connected via reservoir channels 422 to the lens volume 41. Here, the actuator elements (Piezo elements) 701 are configured to bend towards the respective chamber 426 when being actuated so as to compress the respective chamber 426 upon bending of the respective actuator element 701 such that liquid 50 is pushed from the reservoir volume 42 into the lens volume 41.

Here, the support structure may comprise a rigid top 34 covering the respective chamber 426 from above as well as a rigid bottom 33 (e.g. a formed by the base element 10 of the lens 1 covering the reservoir volume 42 from below) wherein the bending actuator elements 701 are connected to the rigid top, particularly via a rigid but still deformable lateral wall 37 of the respective chamber 426 that connects the rigid top 34 with the rigid bottom 33, wherein particularly the respective bending actuator element 701 also forms part of a wall (e.g. ceiling) of the respective chamber 426 and may enclose an air gap 426a with the rigid top 34.

Furthermore, FIG. 16 shows a variant of the embodiment shown in FIG. 15, wherein here, in contrast to FIG. 15, the bending actuator elements 701 are arranged on top of and along a reservoir channel 422 connecting a circumferential reservoir section 421 of the reservoir volume 42 fluidly to the lens volume 42, and are configured to bend towards the at least one reservoir channel 422 when being actuated so as to compress the at least one reservoir channel 422 upon bending of the respective actuator element 701 such that liquid 50 is pushed from the reservoir volume 422 into the lens volume 41.

Here, the support structure may comprise a rigid top 34 covering the reservoir volume 42 at least in sections, particularly the at least one reservoir channel 422, from above as well as a rigid bottom 33 (e.g. formed by the base element 10 of the lens 1 covering the reservoir volume from below), wherein the actuator elements 701 may each be connected to the rigid top 34, particularly via a partially deformable mount 39, wherein particularly the bending actuator elements 701 form part of a wall (e.g. ceiling) of the at least one reservoir channel 422 and may each enclose an air gap 422b with the rigid top 34.

Figure 19:
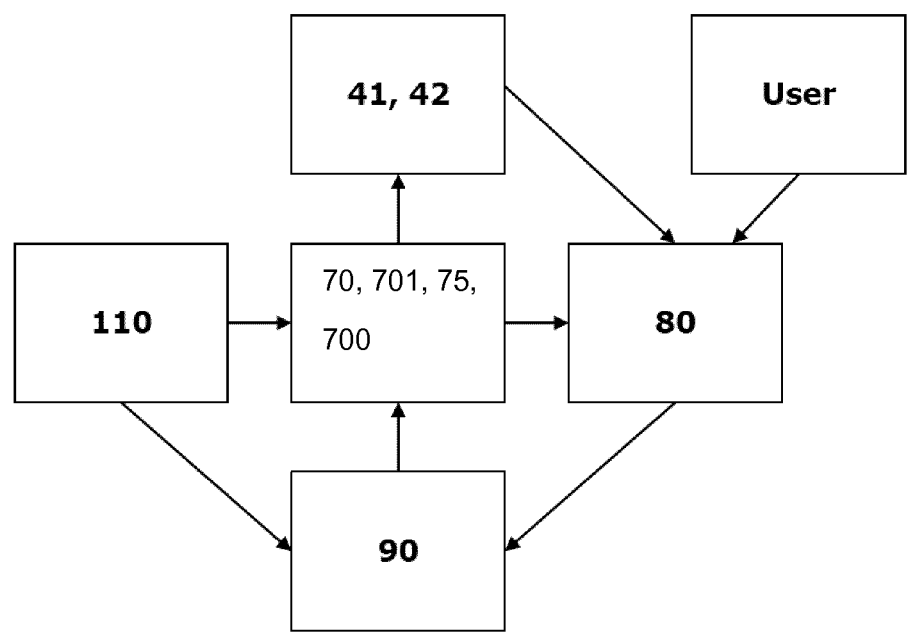
FIG. 19 illustrates an interaction between a contact lens according to the invention and its sensor, actuator, and processing unit.

The individual pumping means 700 described herein (particularly its actuator 70 or individual actuating elements 701 such as the Piezo elements described herein, as well one or several valves 75) may be actuated/controlled as indicated in FIG. 19. According thereto, the contact lens 1 comprises a sensor means 80 (e.g. according to an embodiment of the present invention) configured to sense a movement of the person (user) wearing the contact lens 1, and to provide an output signal in response to a pre-determined movement of said person that is made accessible to a processing unit 90. Particularly said movement is a movement of a crystalline lens or an eyelid 4 of an eye 2 of said user that wears the contact lens 1. The processing unit 90 is configured to actuate the pumping means 700 (i.e. the respective actuator 70, actuating element 701, or valve(s) 75) in response to the output signal provided by the sensor 80 in order to transfer liquid from the reservoir volume 42 to the lens volume 41 or vice versa. Further, an electrical energy source 110 is arranged in the contact lens 1 that provides the necessary power for the components 70, 80, 90.

Particularly, the sensor means 80 is one of: a photosensitive element, a pressure sensing element, a capacitive sensing element, a thermal sensor, particularly a resistor or an arrangement of three sensors 800, 801, 802 as shown in FIG. 7. Further, for instance, a photosensitive element is arranged such in the contact lens 1 that it can be covered by an eyelid and may thus generate a signal that can be used to control the processing unit 90. The resistor can be used to determine a position of the eyelid 4 since it is sensitive to heat that will be transferred from the eyelid 4 to the resistor. For instance, the resistor can extend along a periphery of the contact lens 1.

Further, the electric energy source 110 can be a battery that can be charged in a variety of different ways, already described above, for instance by means of inductive charging. Further, a solar cell 120 may be used in order to charge the battery 110, which solar cell can be arranged, like the battery 110, besides the lens volume 41 outside the ring member 30, for instance.

Further, the sensor 80 can also sense the status of the contact lens by for example measuring a capacitance of the actuator 70. This can be done by superimposing a high frequency sensing signal to the actuator signal. The sensing signal allows to measure the capacitance of the actuator.

Figure 18:
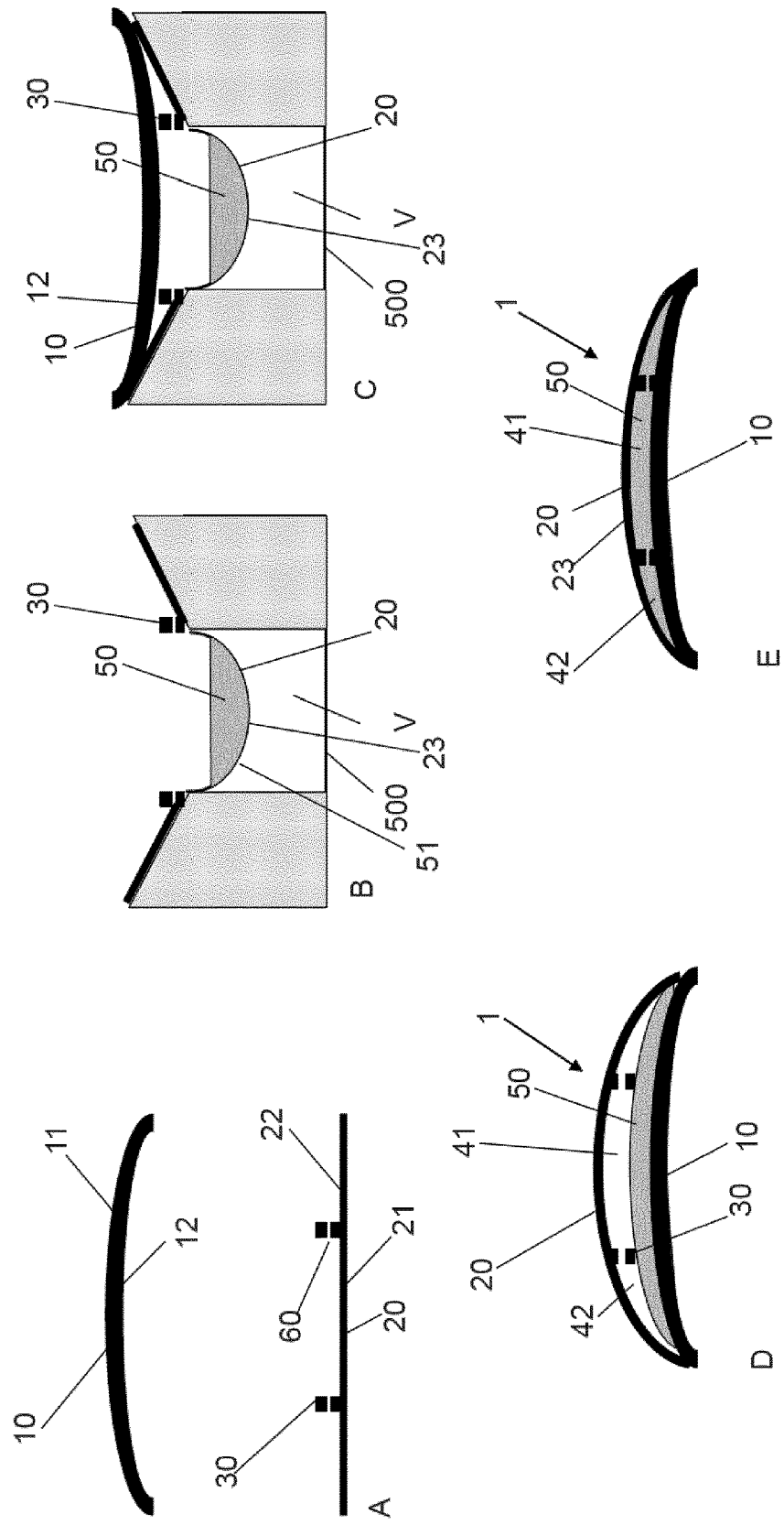
FIG. 18 schematically shows a method for manufacturing a contact lens according to the invention.

Finally, FIG. 18 shows a method for manufacturing a contact lens 1 according to the invention.

According thereto, a base element 10 is provided, as well as a transparent and elastically deformable membrane 20 (cf. FIG. 19A) comprising a ring member 30 connected to a back side 22 of the membrane 20, further components as described above (e.g. a support structure 31, a pumping means 700, a controller 90, a sensor means 80, and/or an energy source 110) may be provided and mounted to the base element 10 (FIG. 19A).

Next, the membrane 20 is filled with said liquid 50 before bonding the membrane 20 to the base element 10, wherein said liquid 50 is filled into a dent 51 formed by the membrane 20, which dent 51 may be formed using a vacuum V acting on the front side 21 of the membrane 20 (FIG. 19B), wherein thereafter the base element 10 is bonded to the membrane 20 (FIG. 19C). Finally, the lens volume 41 and/or reservoir volume 42 is freed from gas residing therein, which is denoted as degassing (cf. FIGS. 19 D and E).

Figure 20:
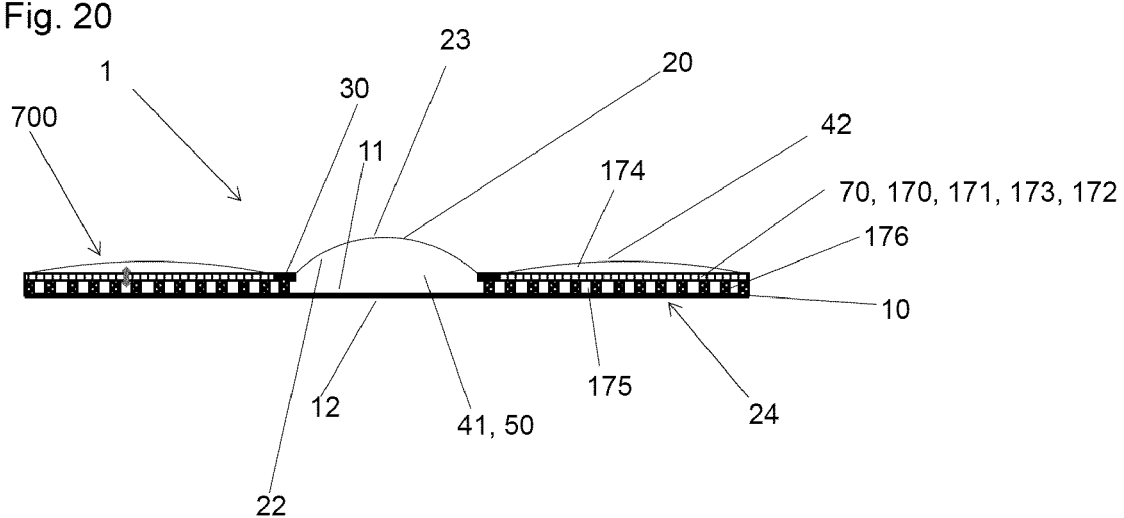
FIG. 20 shows a schematical cross section of an embodiment of the lens according to the invention comprising an electro-osmotic pump for pumping liquid from the reservoir volume to the lens volume and vice versa.
Figure 21:
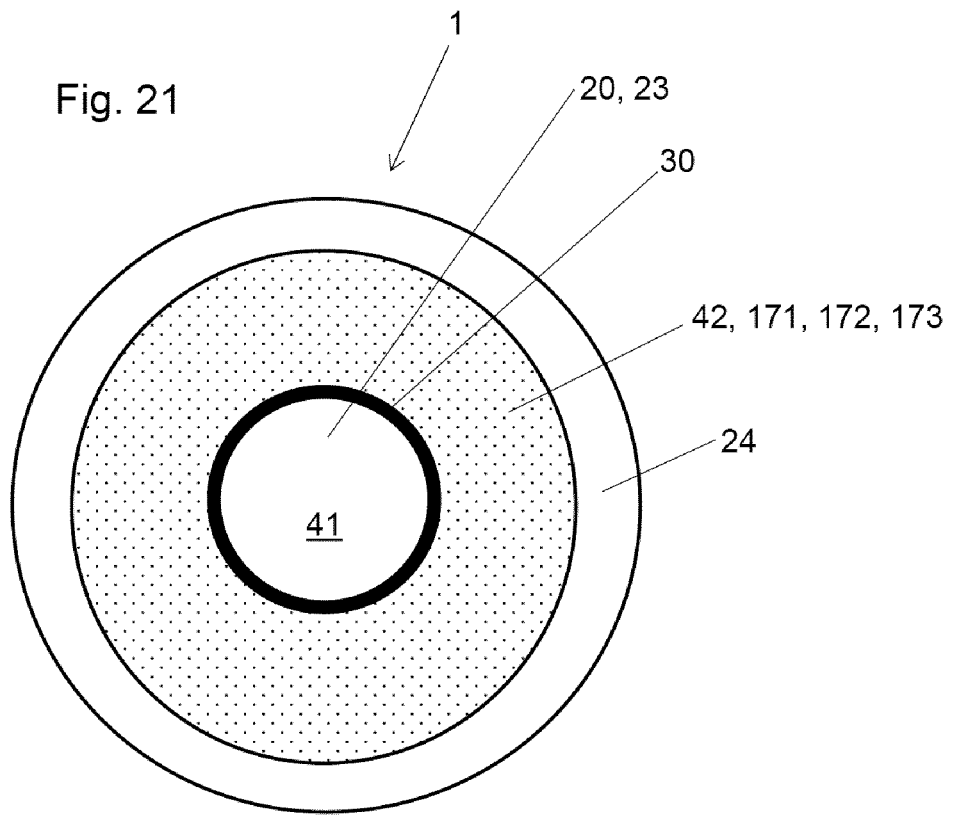
FIG. 21 shows a schematical top view of the embodiment according to FIG. 20.
Figure 22:
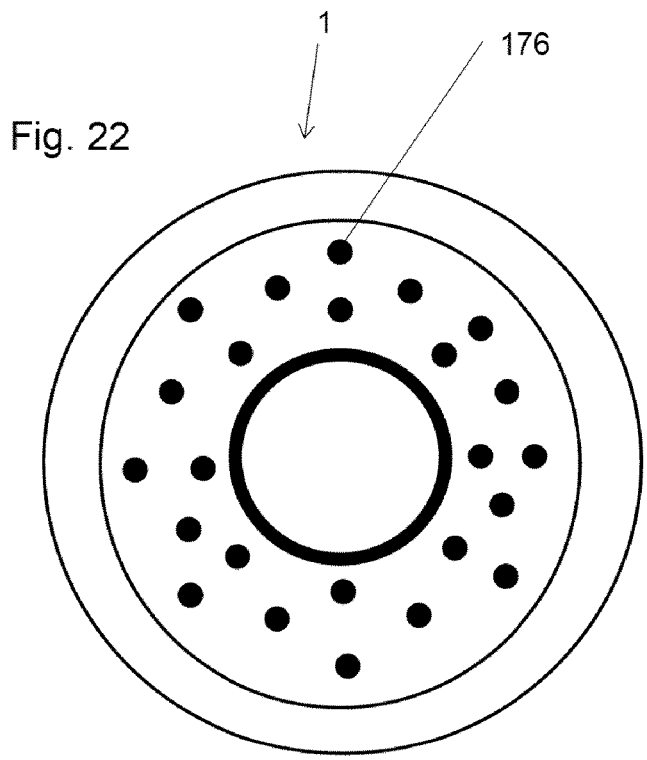
FIG. 22 shows a schematical cross sectional view of a lower compartment of the reservoir volume of the lens of FIGS. 20 and 21.

FIG. 20 shows in conjunction with FIGS. 21 and 22 a further embodiment of a lens 1, particularly in form of a contact lens 1, according to the present invention. Here, the lens 1 comprises in turn a transparent base element 10 having a back side 12, and a front side 11 facing away from the back side 12, a transparent and elastically expandable membrane 20 connected to said base element 10, wherein said membrane 20 comprises a back side 22 that faces said front side 11 of the base element 10, and a ring member 30 (lens shaper) connected to said the membrane 20 so that the ring member 30 defines a curvature-adjustable area 23 of the membrane 20. Further, the lens 1 comprises a lens volume 41 adjacent said curvature-adjustable area 23 of the membrane 20, which lens volume 41 is delimited by the ring member 30, by the membrane 20, and by the base element 10. Furthermore the lens 1 comprises an (e.g. circumferential) reservoir volume 42 arranged in a boundary region 24 of the lens 1, wherein said two volumes 41, 42 are each filled with a transparent liquid 50.

In order to adjust the curvature of said area 23 of the membrane 20, the lens 1 further comprises a pumping means 700 in the form of an electro-osmotic pump 170 configured to transfer transparent liquid 50 from the reservoir volume 42 to the lens volume 41 or vice versa such that the curvature of said curvature-adjustable area 23 of the membrane 20 changes and the focal length of the lens 1 changes. Thus, light passing through the lens volume 41 (e.g. via the area 23, the liquid 50 and the base element 10) can be influenced in a variable manner according to the adjusted focal power of the lens 1.

Particularly, the electro-osmotic pump 170 comprises a porous membrane 173 sandwiched between a first (top) electrode 171 and a second (bottom) electrode 172 of the assembly 170.

The electro-osmotic pump 170 separates an upper compartment 174 of the reservoir volume 42 from a lower compartment 175 of the reservoir volume 42, which lower (or upper) compartment 175 is in fluid communication with the lens volume 41. The lower compartment 175 may comprise a support structure 176 for supporting the osmotic pump 170/porous membrane 173. The support structure may be formed as multiple pillars 176.

By applying an appropriate voltage to the porous membrane 173 via said electrodes 172, 173, the porous membrane 173 pumps liquid 50—in a known manner—from the upper compartment 174 to the lower compartment 175 (or vice versa) and therefore into the lens volume 41, or from the lower compartment 175 into the upper compartment 174 (or vice versa) and therefore from the lens volume 41 into the reservoir volume 42. The pumping can be controlled according to the principles described herein, see also below.

Figure 23:
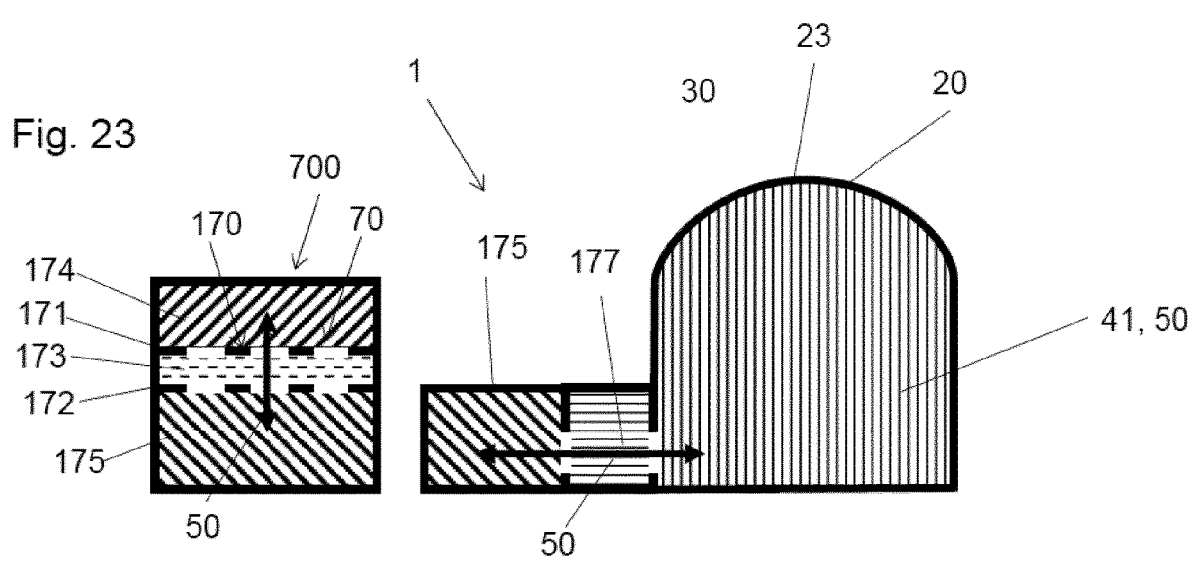
FIG. 23 shows a further embodiment of a lens according to the present invention comprising an electro-osmotic pump for pumping liquid from the reservoir volume to the lens volume and vice versa.
Figure 24:
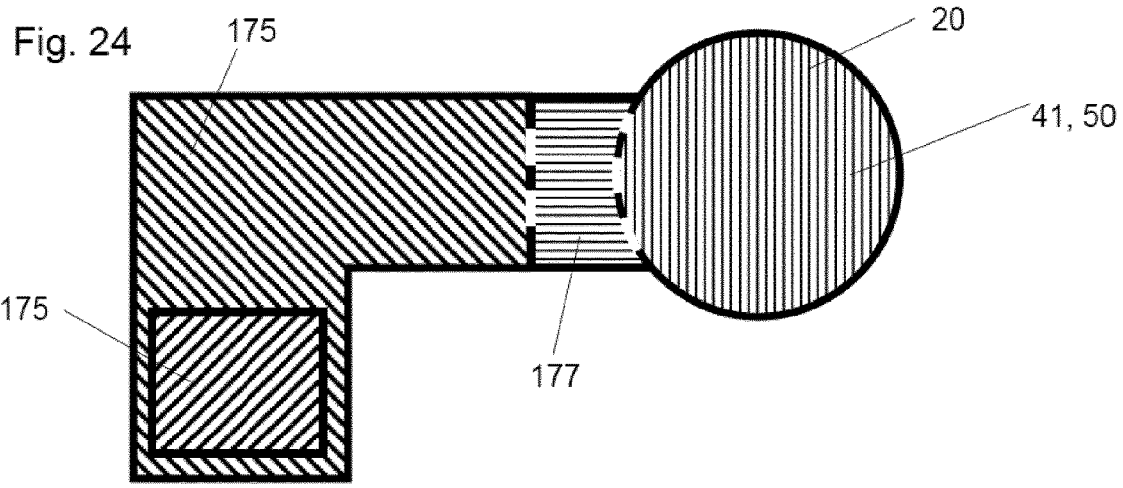
FIG. 24 shows a top view of the embodiment shown in FIG. 23.

FIG. 23 shows in conjunction with FIG. 24 a further, more general embodiment of the present invention. Here, the reservoir volume 42 can have an arbitrary shape and can be placed somewhere at the periphery of the lens 1. The reservoir volume 42 is connected to the lens volume 41 via at least one channel 177, which lens volume 41 is again delimited by a membrane 20 having said curvature adjustable area 23 that can be defined by means of a ring member (lens shaper) which is not shown in FIGS. 23 to 24.

Also here, the reservoir volume 42 comprises an upper compartment 174 that is separated from a lower compartment 175 that is connected to the lens volume 41 via said channel 177 by an electro-osmotic pump 170, which comprises again a first (upper) electrode 171 and a second (lower) electrode 172 on either side of a porous membrane 173. Also here, by applying a suitable voltage to the electrodes 171, 172, liquid 50 can be pumped in both directions across the porous membrane 173 so that the curvature of the area 23 of the membrane 20 can be adjusted and therewith the focal power of the lens 1 that affects the light that travels through the lens volume 41 and the liquid 50 therein via said area 23 of the membrane 20.

Figure 25:
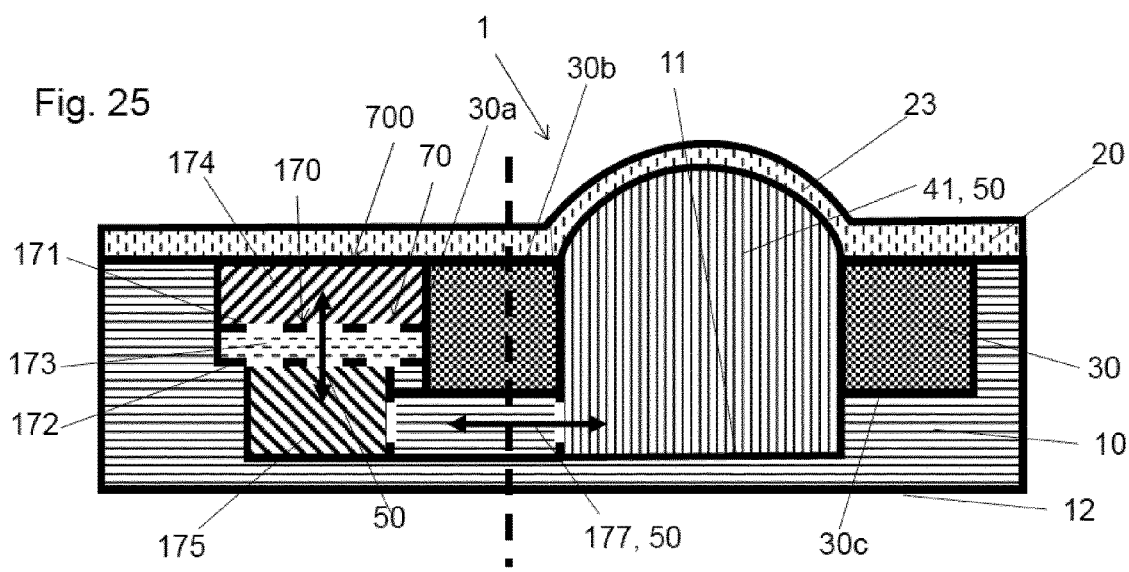
FIG. 25 shows a further embodiment of a lens according to the present invention comprising an electro-osmotic pump for pumping liquid from the reservoir volume to the lens volume and vice versa.

According to the embodiment shown in FIG. 25, the lens 1 may comprise a base element 10 that comprises recesses for receiving the ring member 30, and the electro-osmotic pump 170, so that the reservoir volume 42 is formed/enclosed by the membrane 20 and the base element 10, and so that the lens volume 41 is enclosed by the membrane 20, the ring member 30 and the base element 10. Said channel 177 connecting the lower compartment 175 to the lens volume 41 may be formed in the base element 10 or between the base element 10 and the ring member 30.

Further, as shown in FIG. 25, the electro-osmotic pump 170 may be arranged or attached to a lateral surface 30a of the ring member 30, which surface 30a connects an upper face side 30b of the ring member 30 to a lower face side 30c of the e.g. circular ring member 30.

Figure 26:
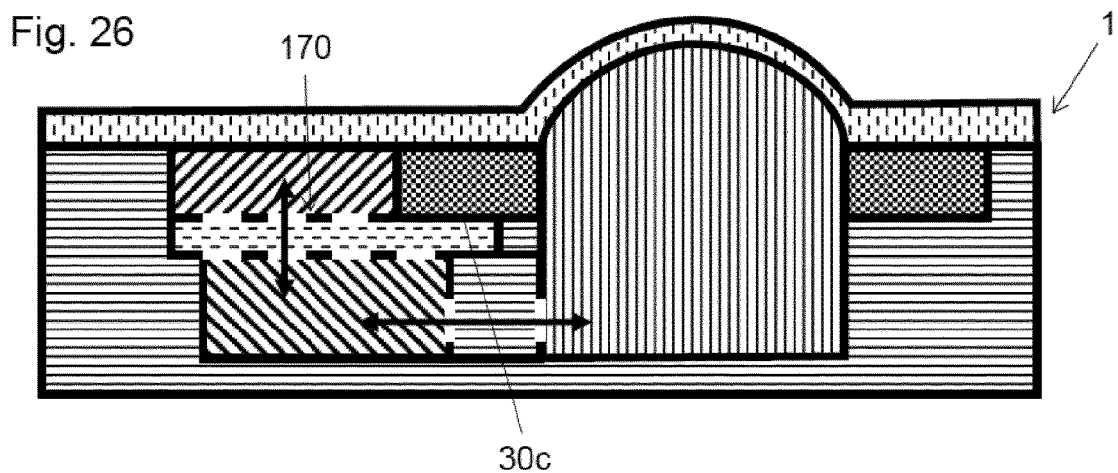
FIG. 26 shows a further embodiment of a lens according to the present invention comprising an electro-osmotic pump for pumping liquid from the reservoir volume to the lens volume and vice versa.

Alternatively, as shown in FIG. 26, the electro-osmotic pump 170 can be attached to said lower face side 30c of the ring member 30. Such a configuration is beneficial for mounting components of the lens 1 during production of the lens 1 as will be explained below with respect to FIGS. 28 and 29.

Figure 27:
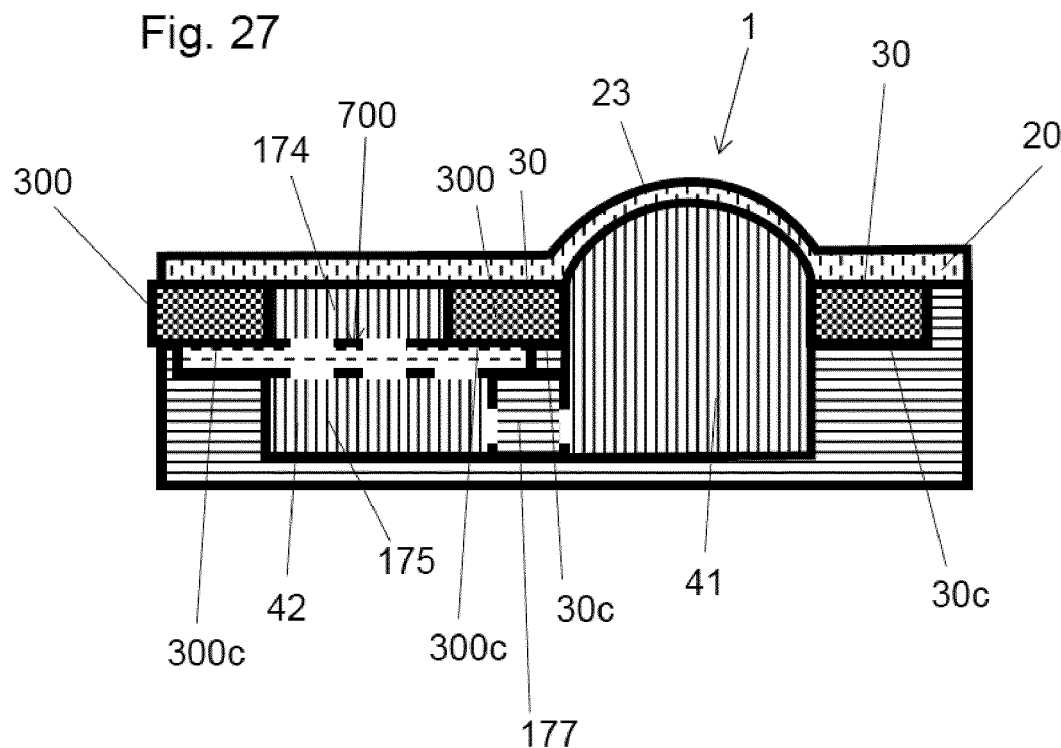
FIG. 27 shows a further embodiment of a lens according to the present invention comprising an electro-osmotic pump for pumping liquid from the reservoir volume to the lens volume and vice versa.

Furthermore, FIG. 27 shows a variant of the embodiment shown in FIG. 26, wherein here the lens 1 comprises a further ring member 300 that is particularly separate from the ring member 30. Such a configuration with two ring members 30, 300 allows to pick and place the fluidic cell, i.e., lens volume 41.

Figure 28:
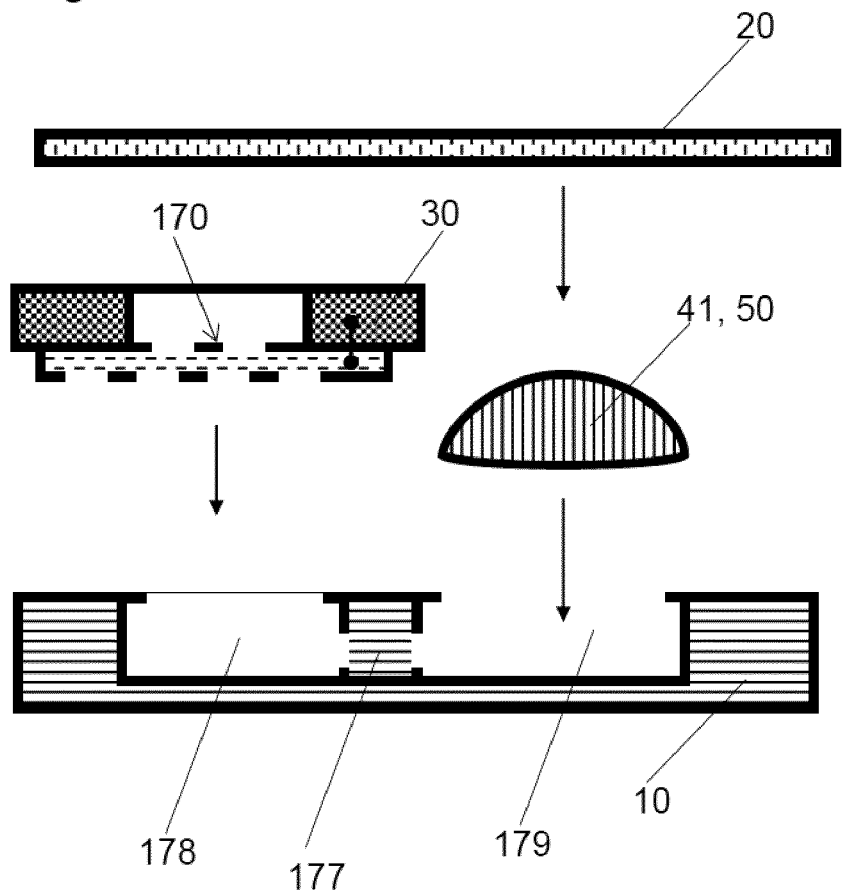
FIG. 28 shows a method for mounting component of a lens according to the invention.

Now, regarding assembly options, FIG. 28 shows the possibility to pre-assemble the electro-osmotic pump 170 on ring member 30 or 300, wherein no electronic component is arranged on the membrane 20 or on the base element 10. Rather, particularly, all electronics are mounted to the ring member 30, as well as all electric connections from the power interface 185 (not shown), battery 110 (not shown), and to the electro-osmotic pump 170 are fully integrated into this block, so that no additional wiring is required after a marriage of the lens element 10 and the ring member 30. Particularly, the ring member 30 with integrated components and the liquid 50 or an enclosed volume (e.g. lens volume 41) of liquid 50 are arranged on the base element 10. Thereafter, the membrane 20 is put on top of the ring member 30, liquid 50 and base element 10 to finalize the lens 1.

Figure 29:
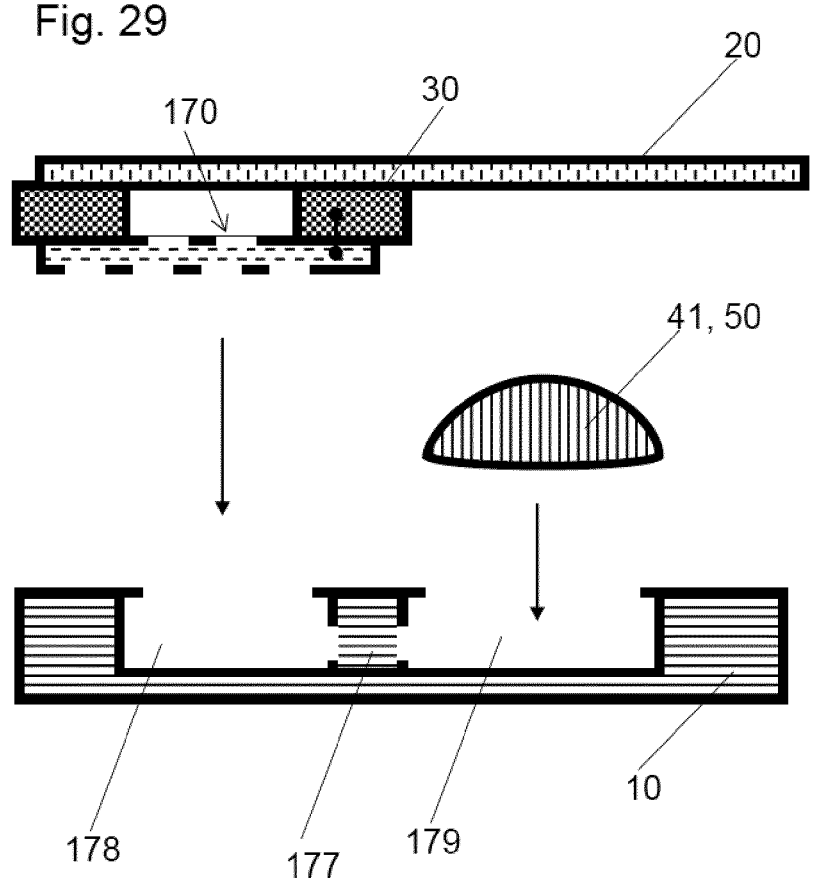
FIG. 29 shows a further method for mounting components of a lens according to the invention.

According to the modification shown in FIG. 29, the integration can be taken one step further, by also pre-mounting the ring member 30 with its integrated components (particularly pump assembly 170) on the membrane 20. Here liquid 50 is arranged on the base element 10 and then the base element 10 is sealed by bonding the membrane 20 with attached ring member 30 to the base element 10.

Figure 30:
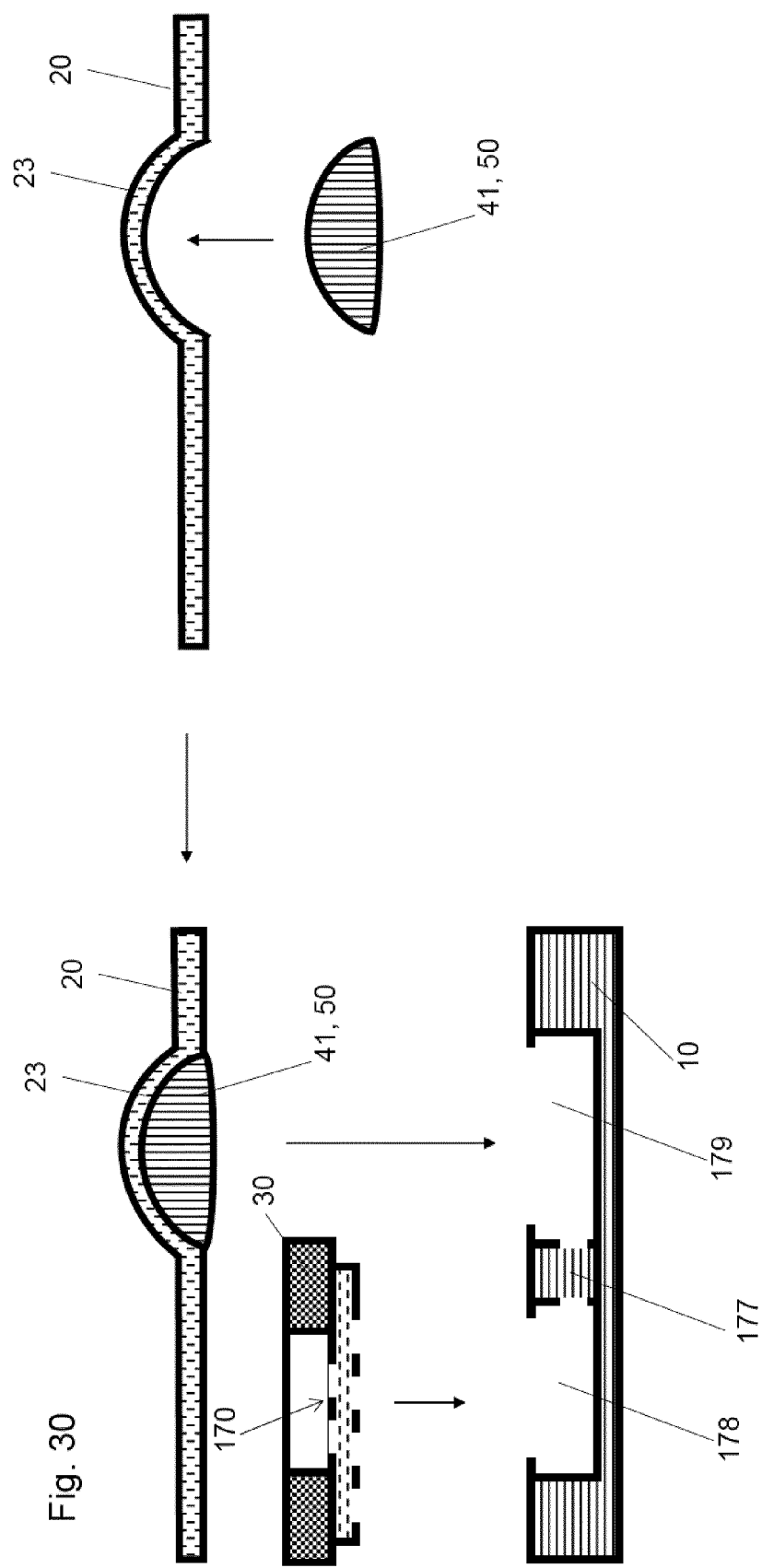
FIG. 30 shows a further method for mounting components of a lens according to the invention.

FIG. 30 shows a further variant of the assembly process. Here, the liquid 50 is filled into/attached to the membrane 20 and the ring member 30 with integrated electro-osmotic pump 170 is arranged on the base element 10. Thereafter, the membrane 20 together with the liquid 50 is bonded to the base element 10.

Figure 31:
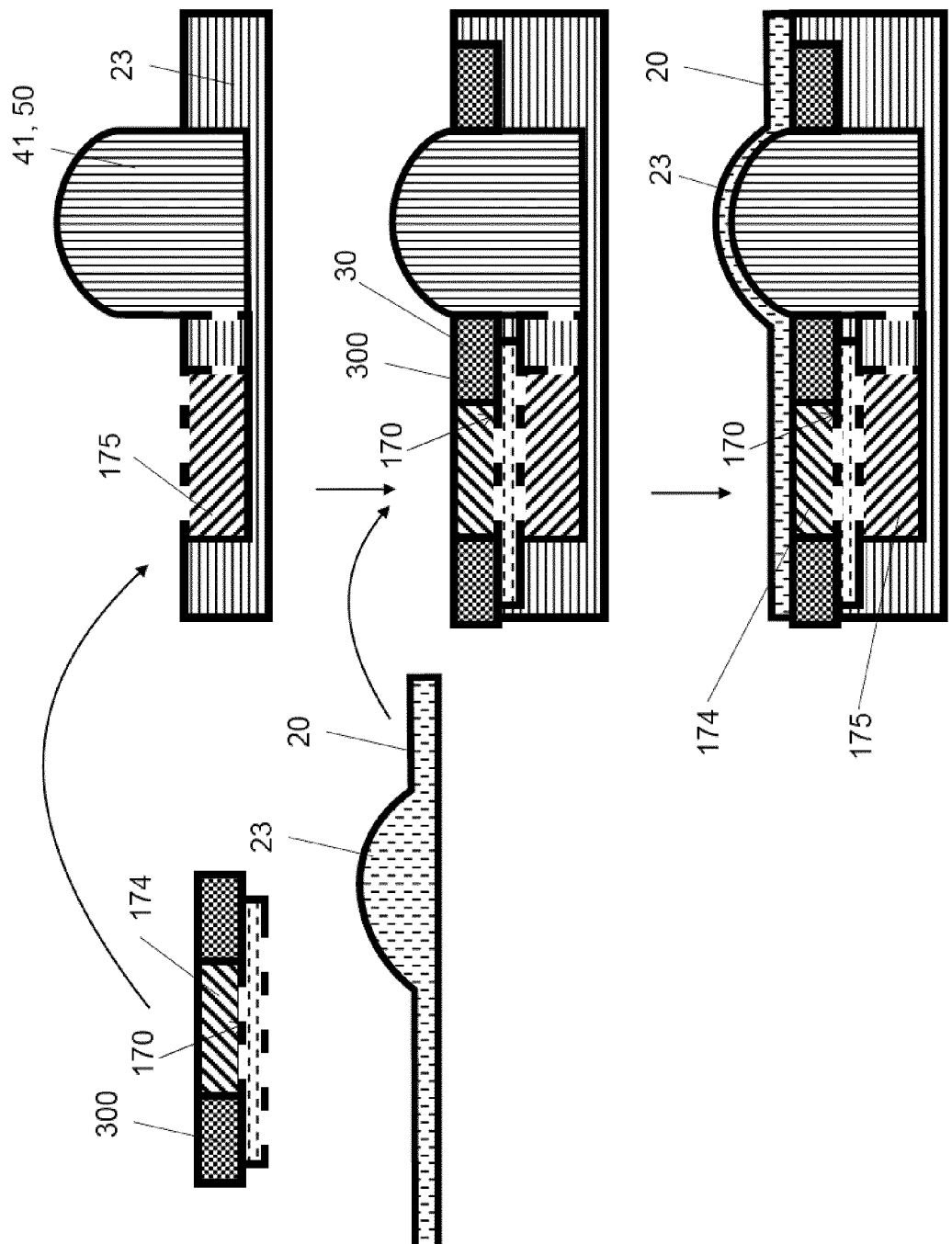
FIG. 31 shows a further method for mounting components of a lens according to the invention.

FIG. 31 shows yet another variant of the assembly process. Here, liquid 50 is filled into the base element 10 and the further ring member 300 with integrated electro-osmotic pump 170 is arranged on the base element 10. Further, the ring member 30 is arranged on the base element 10. Thereafter, the membrane 20 is arranged on the base element 10 covering the ring members 30, 300 and sealing the lens 1.

Figure 32:
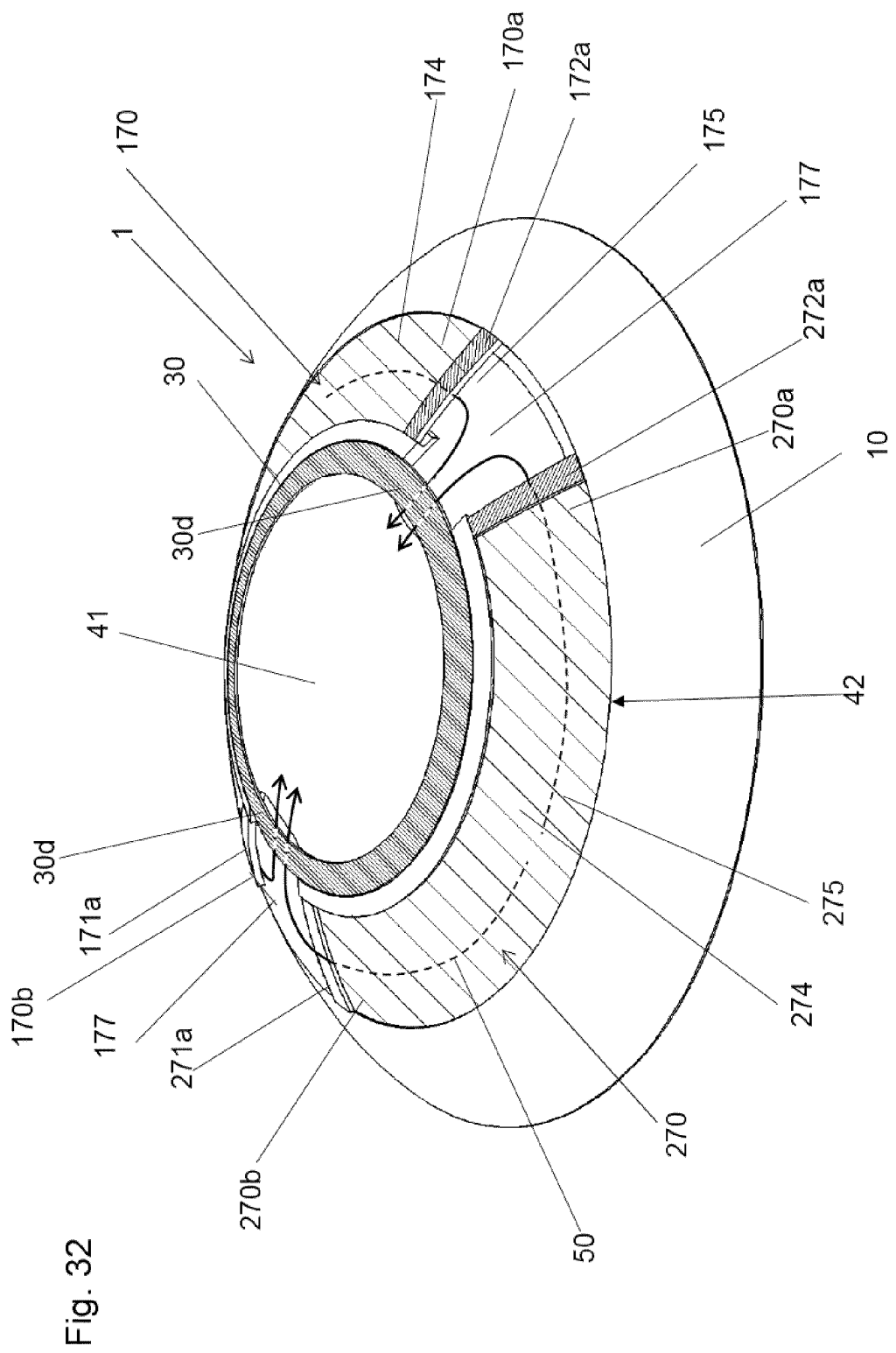
FIG. 32 shows a perspective view of a further embodiment of a lens according to the invention using an electro-osmotic pump for pumping the lens liquid.
Figure 33:
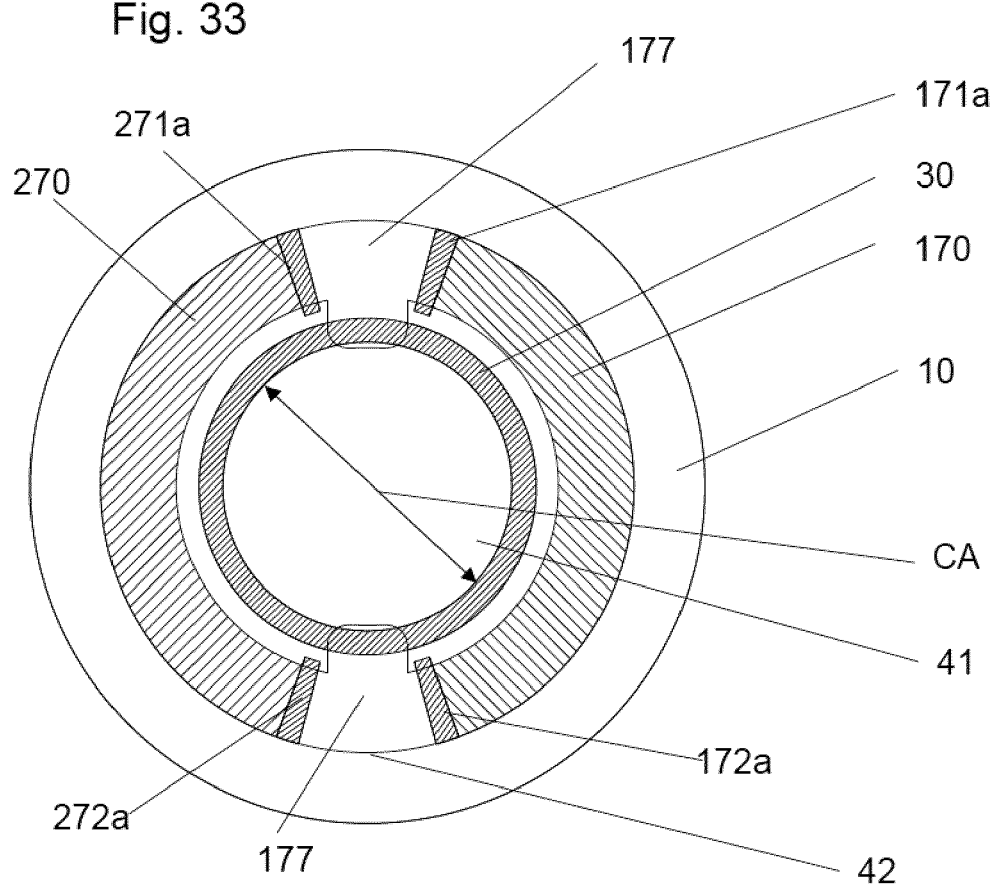
FIG. 33 shows a top view of the embodiment shown in FIG. 32.
Figure 34:
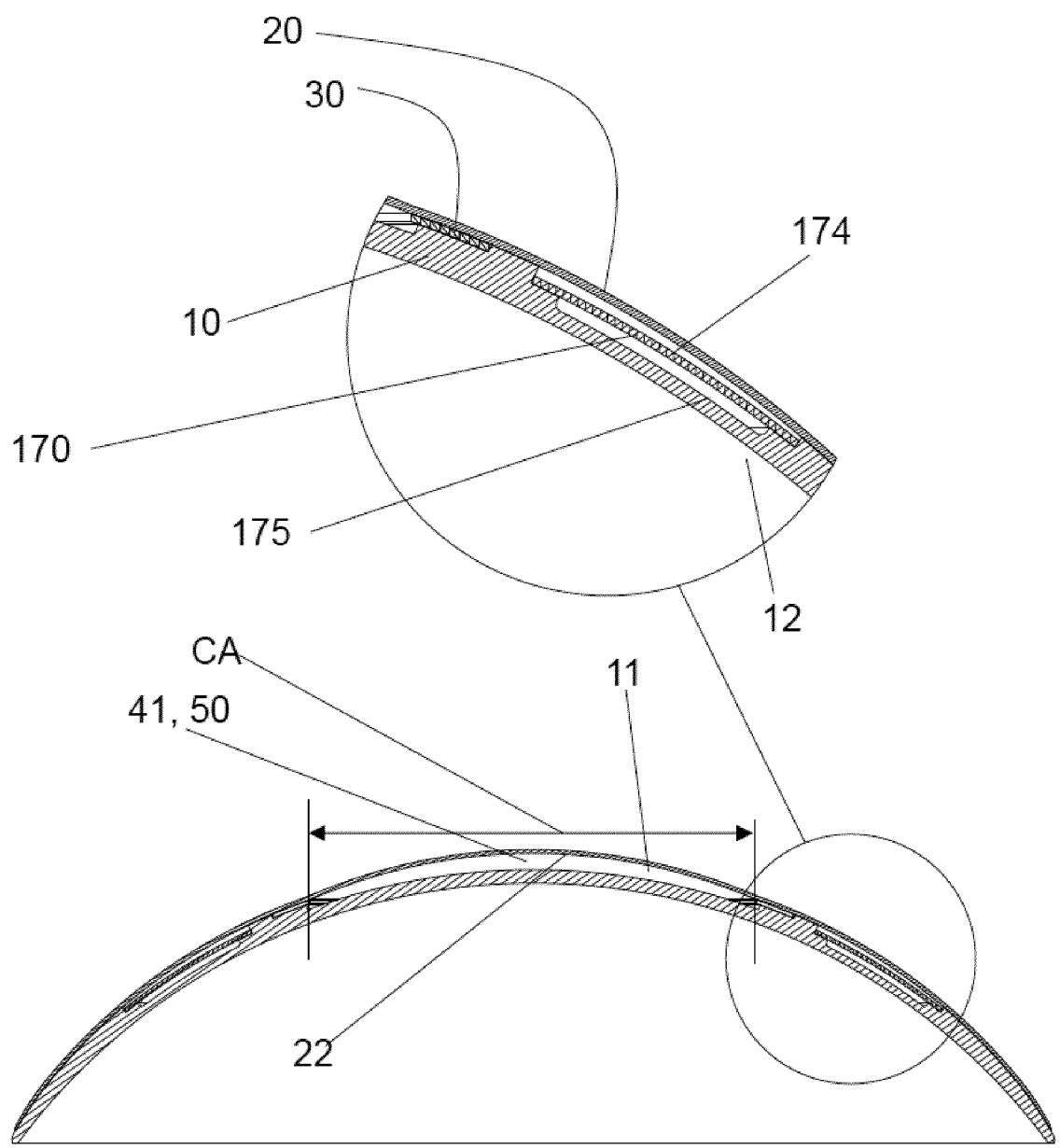
FIGS. 34-35 show cross sectional views of the embodiment shown in FIGS. 32 and 33.
Figure 35:
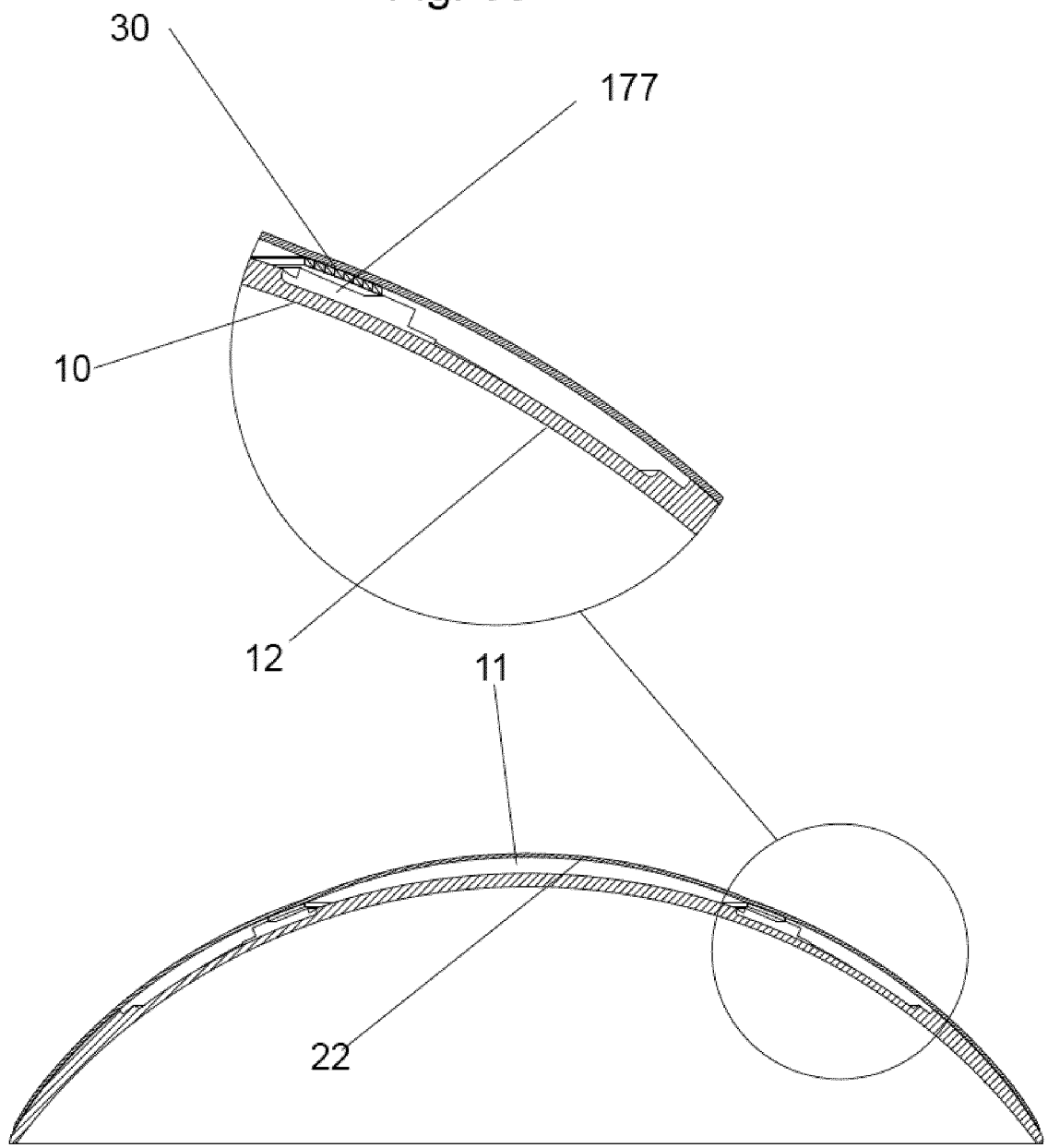
Figure 36:
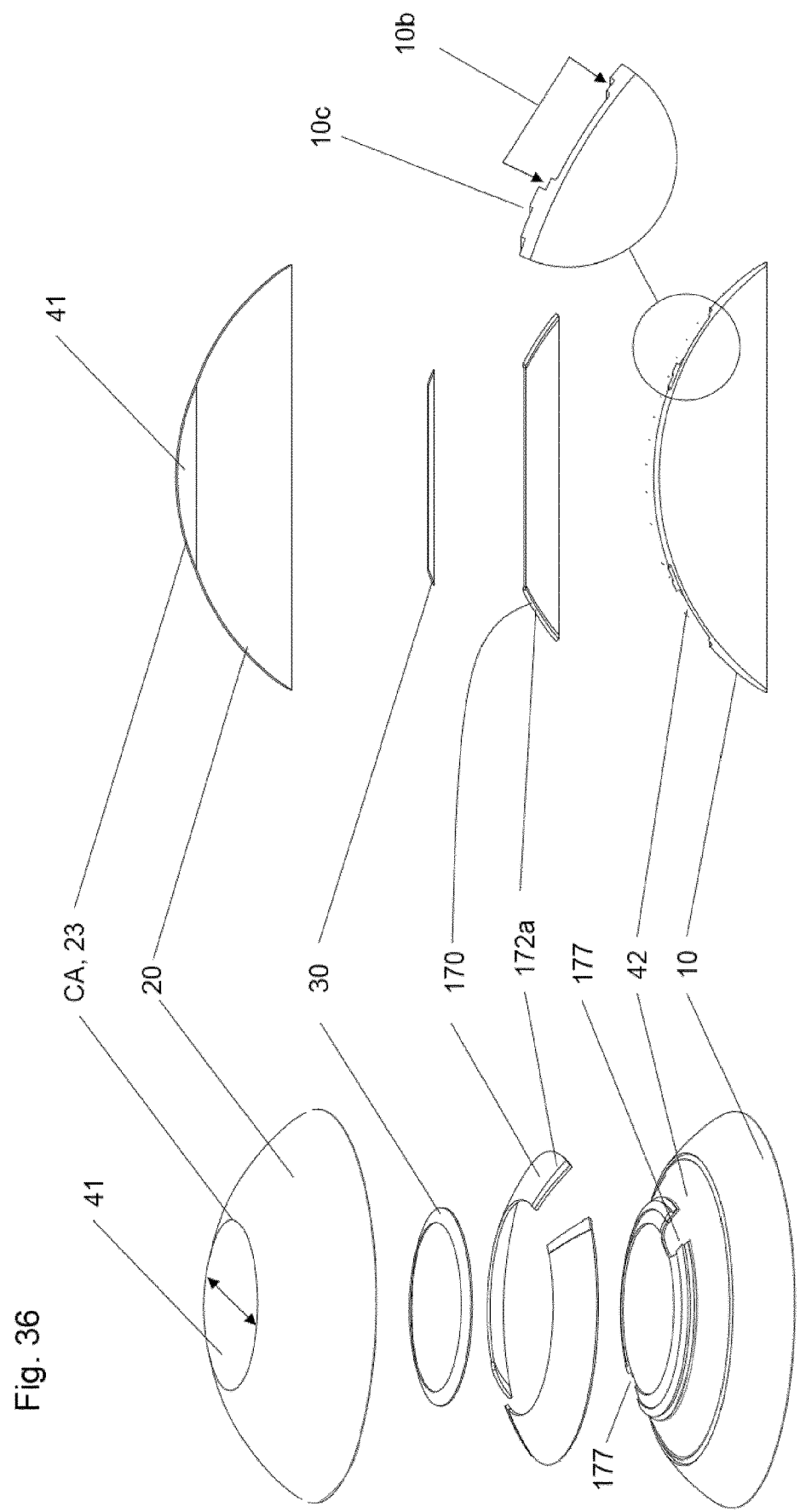
FIG. 36 show exploded views of the embodiment shown in FIGS. 32 to 35.

FIG. 32 shows, in conjunction with FIGS. 33 to 36 a further embodiment of a lens 1 according to the invention, wherein particularly CA denotes the so called clear aperture.

Here, again, the lens 1 comprises a transparent base element 10 having a back side 12, and a front side 11 facing away from the back side 12, a transparent and elastically expandable membrane 20 connected to said base element 10, wherein said membrane 20 comprises a back side 22 that faces said front side 11 of the base element 10, and a ring member 30 connected to said the membrane 20 so that the ring member 30 defines a curvature-adjustable area 23 of the membrane 20. Further, the lens 1 comprises a lens volume 41 adjacent said curvature-adjustable area 23 of the membrane 20, which lens volume 41 is laterally delimited by the ring member 30, upwards by the membrane 20, and downwards by the base element 10. Furthermore, the lens 1 comprises a reservoir volume 42 arranged in a boundary region 24 of the lens 1/base element 10, wherein said two volumes 41, 42 are each filled with a transparent liquid 50.

In order to adjust the curvature of said area 23 of the membrane 20, the lens 1 further comprises a pumping means configured to transfer transparent liquid 50 from the reservoir volume 42 to the lens volume 41 or vice versa such that the curvature of said curvature-adjustable area 23 of the membrane 20 changes and the focal length of the lens 1 changes. Thus, light passing through the lens volume 41 (e.g. via the area 23, the liquid 50 and the base element 50) can be influenced in a variable manner according to the adjusted focal power of the lens 1.

Figure 41:
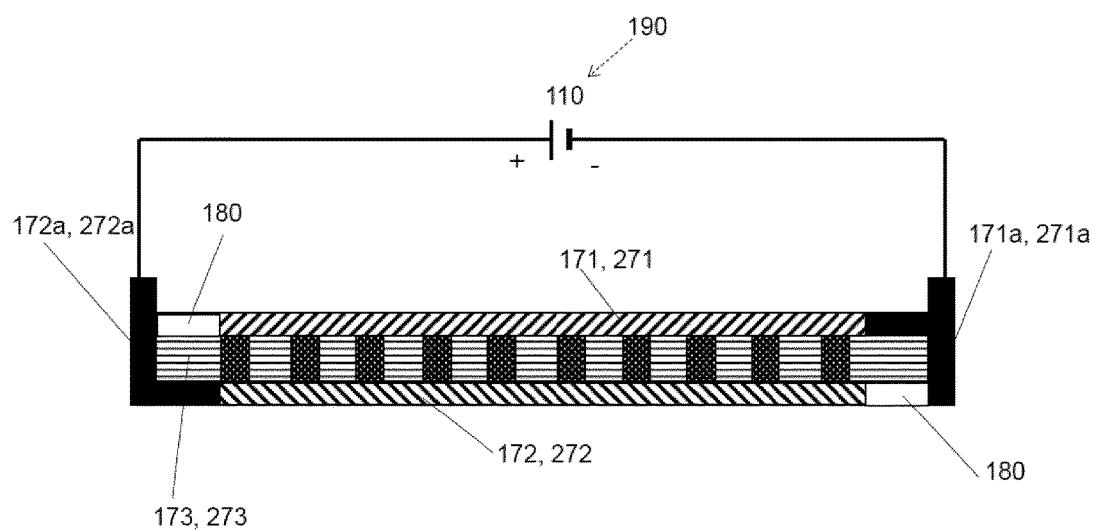
FIG. 41 shows a schematical cross sectional view of an electro-osmotic pump according to the invention.
Figure 42:
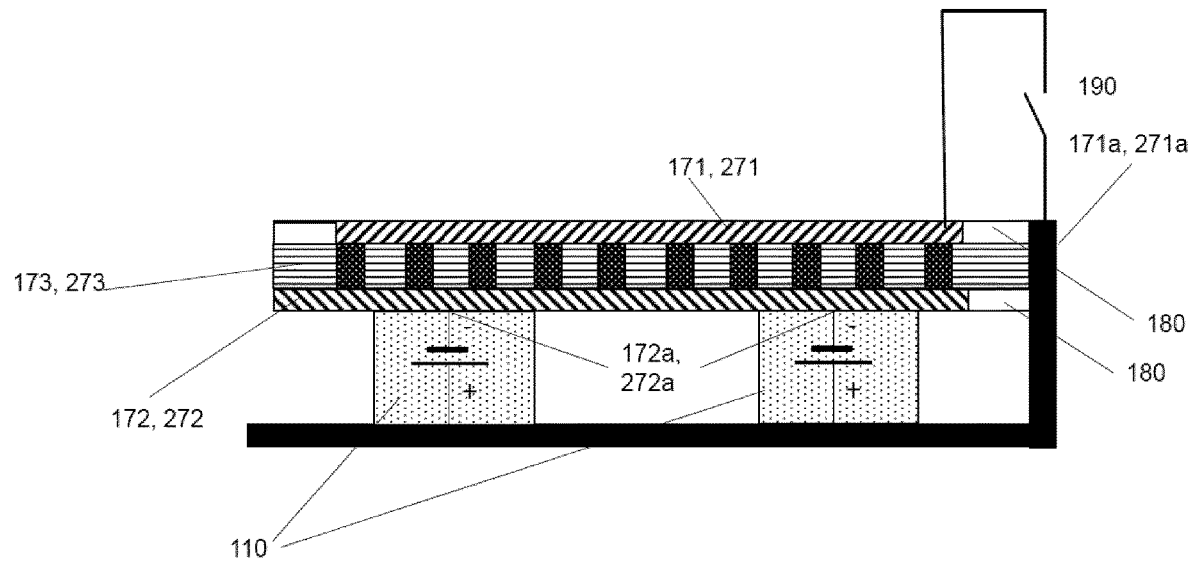
FIG. 42 shows a modification of the embodiment shown in FIG. 41.

Particularly, the pumping means comprises or is formed by a first electro-osmotic pump 170 that comprises a porous membrane 173 sandwiched between a first (top) electrode 171 and a second (bottom) electrode 172 of the first pump 170, as well as a further second electro-osmotic pump 270 that also comprises a porous membrane 273 sandwiched between a first (top) electrode 271 and a second (bottom) electrode 272 of the second pump 270 (cf. FIG. 41 or 42).

Both electro-osmotic pumps 170, 270 separate an upper compartment 174, 274 of the reservoir volume 42 from a lower compartment 175, 275 of the reservoir volume 42, respectively, wherein the respective upper compartment 174, 274 is arranged on the associated lower compartment 175, 275.

Particularly, the respective pump 170, 270 is configured to pump liquid 50 from the respective upper compartment 174, 274 into the associated lower compartment 175, 275 and thereby into the lens volume 41 or from the respective lower compartment 175, 275 to the respective upper compartment 174, 274 and thereby from the lens volume 41 into the reservoir volume 42 depending on a voltage applied to said electrodes 171, 172, 271, 272 of the respective pump 170, 270.

In order to apply a suitable voltage to the porous membranes 173, 273, the respective electro-osmotic pump 170, 270 comprises a first contact lead 171a, 271a for connecting a battery 110 to the respective first electrode 171, 271, and a second contact lead 172a, 272a for connecting said battery 110 to the respective second electrode 172, 272, wherein particularly the respective first contact lead 171a, 271a is arranged at a first end 170a, 270a of the respective electro-osmotic pump 170, 270, and wherein particularly the respective second contact lead 172a, 272a is arranged at an opposite second end 170b, 270b of the respective electro-osmotic pump 170, 270.

Preferably, both pumps 170, 270 comprise a curved shape and particularly follow the course of a circumferential arc, respectively.

As shown in FIG. 32, the base element 10 comprises a circumferential (e.g. circular) recess 10a on the front side 11 of the base element 10 on top of which the membrane assemblies 170, 270 are placed such that recess 10a forms a bottom and side wall of the lower compartments 175, 275 while the upper compartments 174 are arranged on top of the respective pump 170, 270 and below the membrane 20.

Particularly, the first ends 170a, 270a of the electro-osmotic pumps 170, 270 face each other. Likewise, the second ends 170b, 270b of the pumps 170, 270 face each other, wherein a channel 177 is arranged between said first ends 170a, 270a and said second ends 170b, 270b, respectively, wherein each channel 177 extends below the ring member 30 into the lens volume 41 so that the lower compartments 175 are in fluid communication with the lens volume 41 via the channels 177. A possible liquid flow is indicated in FIG. 32 by dashed lines.

Further, preferably, for aligning the electro-osmotic pumps 170, 270 with respect to the recess 10a, the recess 10a comprises two opposing steps 10b (cf. FIG. 36) for aligning said first and second electro-osmotic pumps 170, 270 with respect to the recess 10a. Further, preferably, the base element 10 comprises yet another a circumferential step 10c (cf. FIG. 36) for aligning the ring member 30 with respect to the base element 10.

Figure 37:
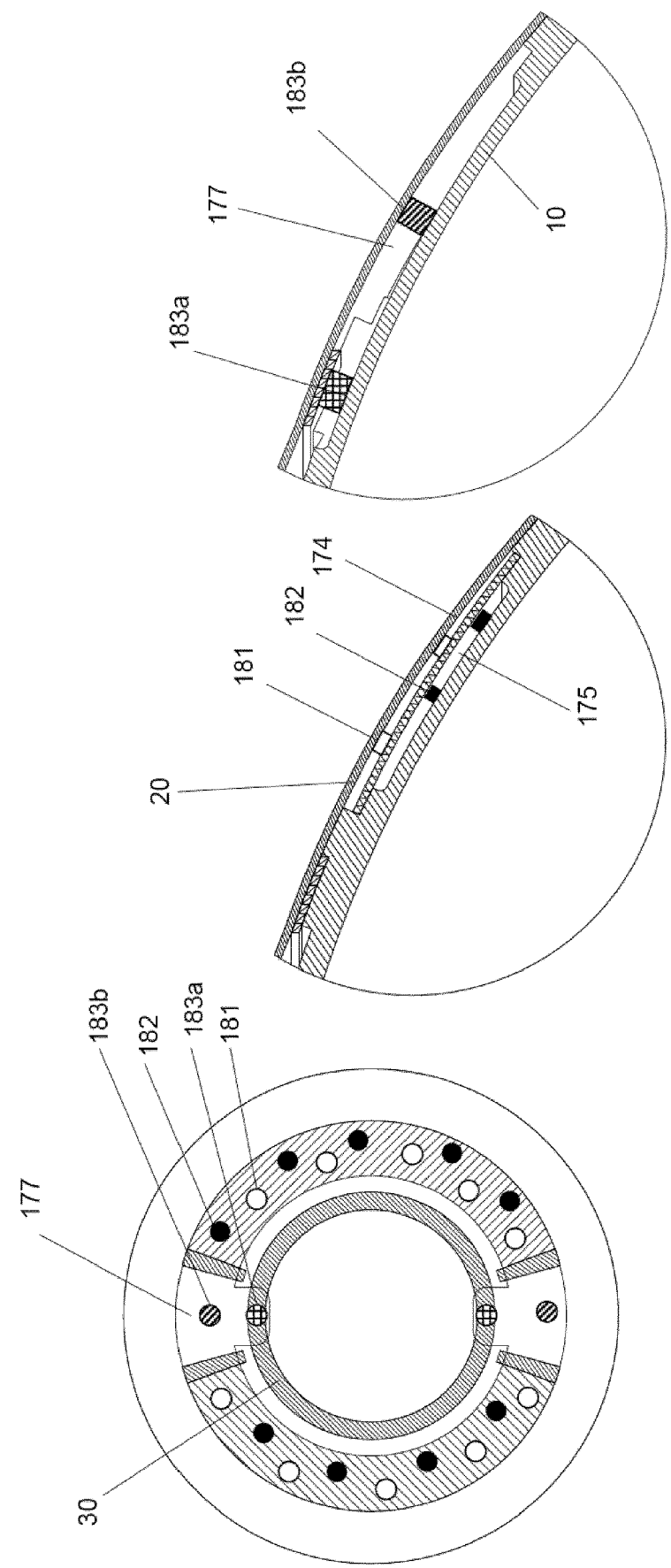
FIG. 37 shows a variant of the embodiment shown in FIGS. 32 to 36 having support structures.

As before, also the embodiments according to FIG. 32 may comprise a support structure as indicated in FIG. 37. Particularly, the lens 1 may comprise a support structure 182 arranged in the lower compartments 175 for supporting said first and second electro-osmotic pumps 170, 270. Furthermore, the lens 1 may comprise a support structure 181 arranged in the upper compartment 174 for supporting said first and second electro-osmotic pumps 170, 172. Particularly, the support structures 181, 182 protect the integrity of the compartments 174, 175, 274, 275. According to the embodiment shown in FIG. 37, the respective support structure 181, 182 may be formed by a plurality of pillars 181, 182.

Furthermore, the lens 1 may also comprise support structures in the channels 177 for supporting the ring member 30 and/or said membrane 20. Also here, the respective support structure 183 may comprise a pillar 183a for supporting the ring member 30 or a pillar 183b for supporting the membrane 20, which protects the integrity of the respective channel 177.

Figure 38:
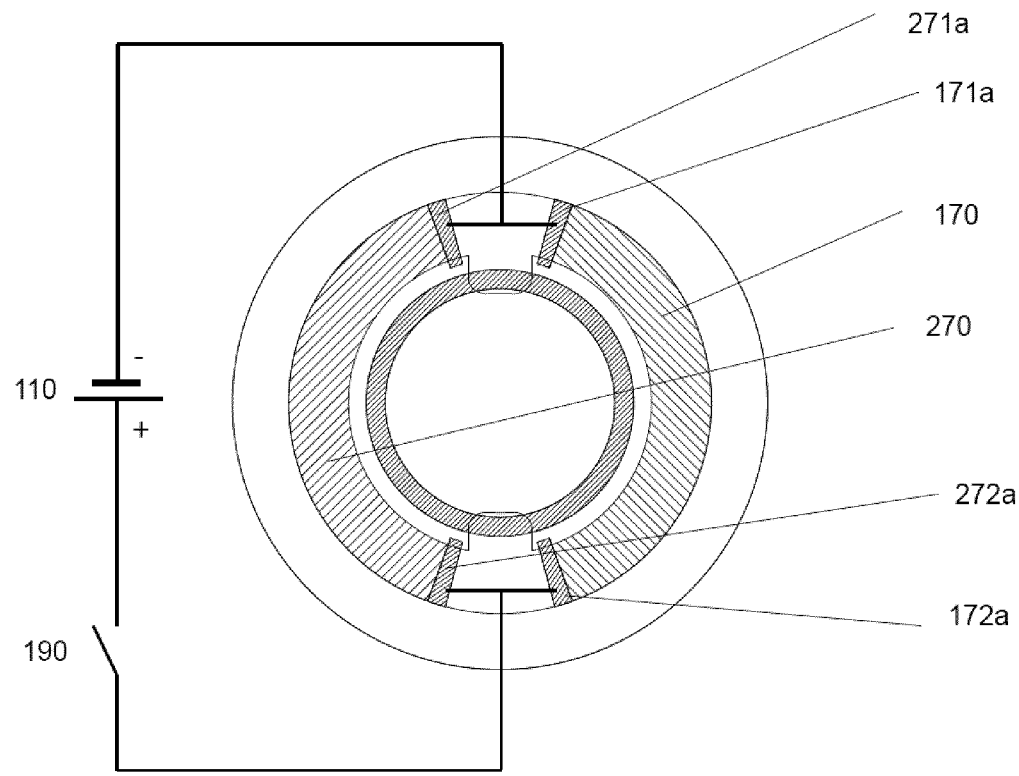
FIG. 38 shows a possible wiring of an external battery and the electrodes of the electro-osmotic pump assemblies of the embodiments shown in FIGS. 32 to 37.

Furthermore, as shown in FIG. 38, the leads 171a, 271a, 172a, 272a may be wired to an external battery 110 or any other battery 110 which may be controlled by a processing unit 190 so as to adjust the focal power on demand.

Here, particularly, the first or second pump 170, 270 can be configured as shown in FIG. 41, i.e., a porous membrane 173, 273 sandwiched between a first (upper) electrode 171, 271 and a (lower) second electrode 172, 272, wherein a first contact lead 171a, 271a connects to the first electrode 171, 271 and is insulated from the second electrode 172, 272 via an insulator 180, while a second contact lead 172a, 272a at an opposing end connects to the second electrode 172, 272 and is insulated from the first electrode 171, 172 by means of a further insulator 180.

Figure 39:
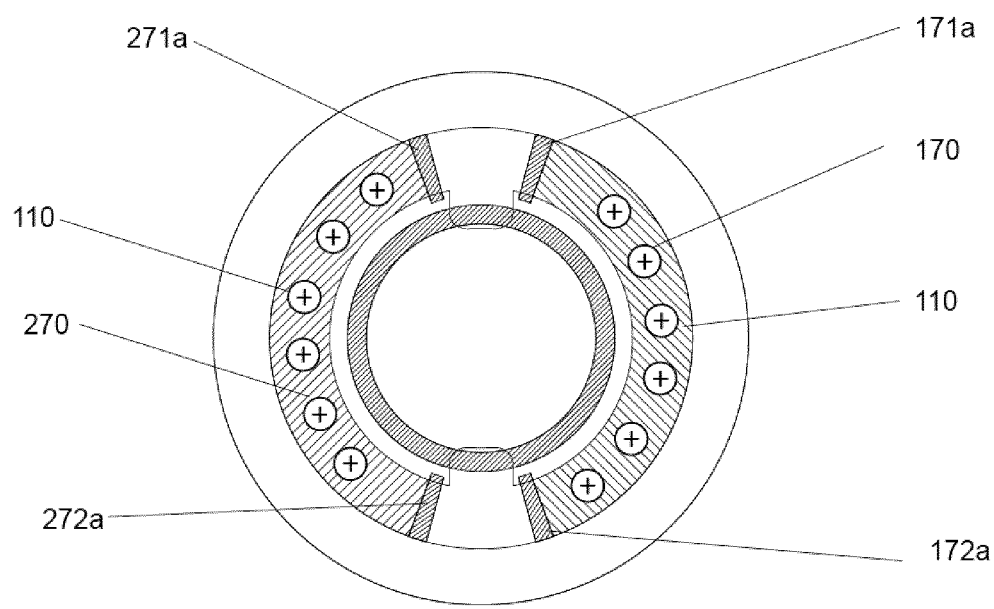
FIG. 39 shows a variant of the lens shown in FIGS. 32 to 37 having an internal battery.
Figure 40:
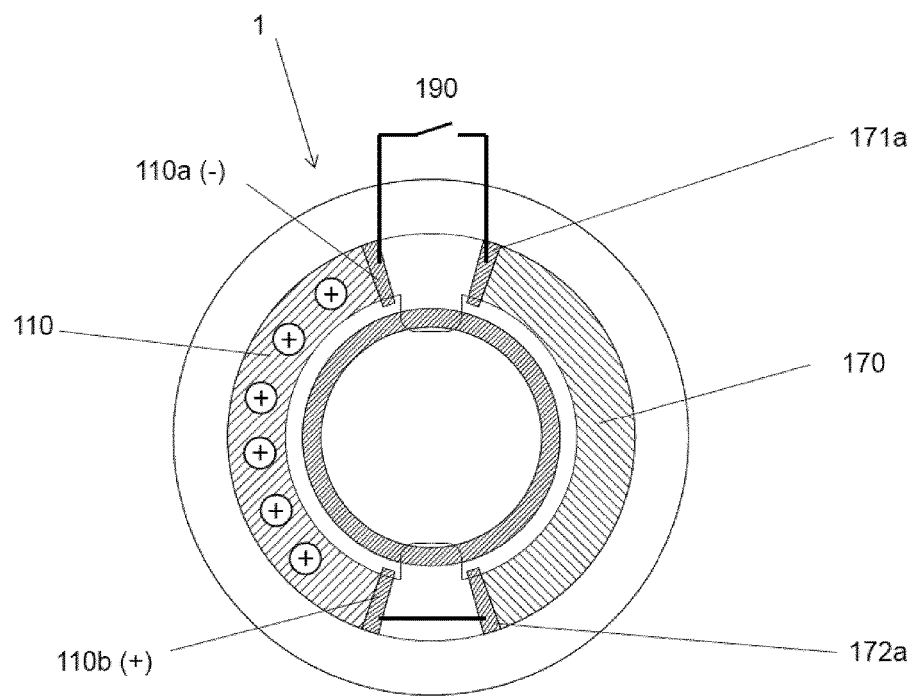
FIG. 40 shows a modification of the embodiment shown in FIG. 39.

However, a battery 110 (or a number of separate battery cells 110), may also be arranged in the reservoir volume 42, particularly in the lower compartments 175, 275 as shown in FIG. 39.

Here, particularly, the pumps 170, 270 can be configured as shown in FIG. 42. Again, the respective porous membrane 173, 273 is sandwiched between a first (upper) electrode 171, 271 and a (lower) second electrode 172, 272, wherein a first contact lead 171a, 271a connects to the first electrode 171, 271 via a conductor and a control element that can be controlled by means of a processing unit 190, wherein insulators 180 are arranged between the electrodes 171, 271, 172, 272 and the first lead 171a, 271a. Further, the battery 110 (or multiple cells 110) is arranged between the first lead 171a, 271a and the second electrode 172, 272. Here, the second lead(s) 172a, 272a may be formed by contact points of the battery 110 with the second electrode 172, 272. However, the individual minus poles of the batteries 110 may also be wired to a common second contact lead 172a, 272a (not shown), e.g. at the opposing end of the second electrode 172, 272.

Figure 44:
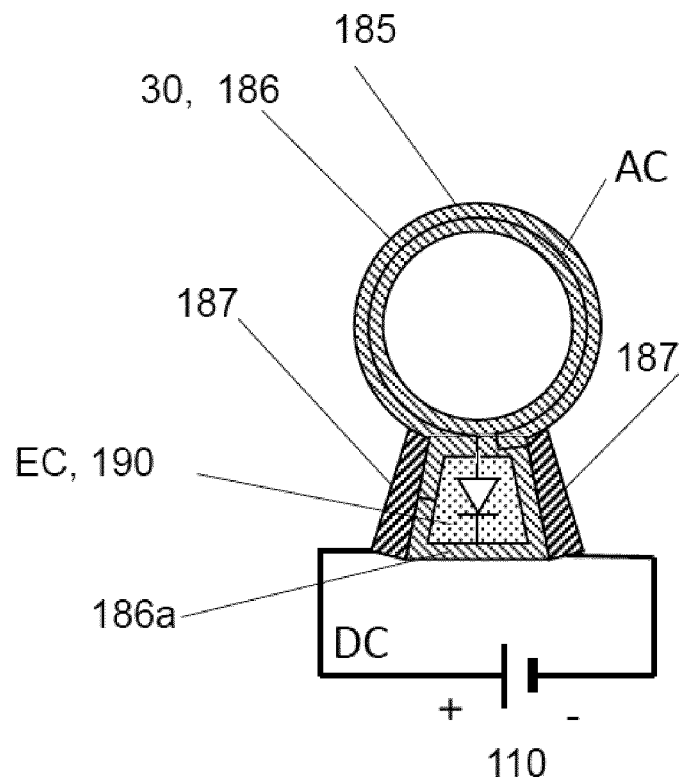

Furthermore, as shown in FIG. 44, the lens 1 may comprise a power interface 185 (e.g. an inductive or RF coil) configured for inductive charging of the battery 110. Such a power interface may be present in all embodiments of the osmotic pumping lens 1.

Figure 43:
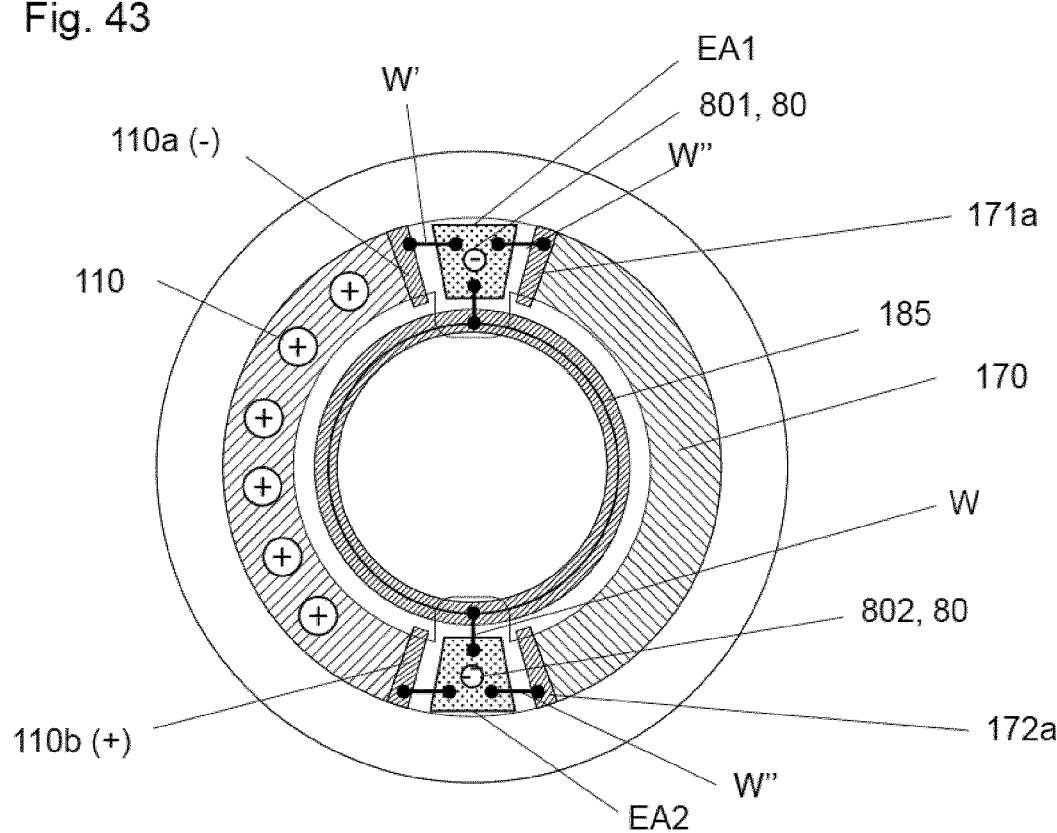
FIGS. 43-44 show a modification of the embodiment shown in FIG. 40.

As further shown in FIG. 43 the lens 1 may comprises a sensor assembly 80 (such a sensor assembly may also be present in all other embodiments of the osmotic pumping lens 1) configured to detect one of: an eye lid movement, a fully closed eyelid, or a partially closed eye lid and to generate a corresponding control signal that is indicative of said detected movement or eye lid state (fully or partially closed) Preferably, the sensor assembly 80 is configured to perform a capacitive, inductive, or impedance measurement.

Particularly, as shown in FIG. 43 the sensor assembly 80 comprises two spaced apart sensors 801, 802 (e.g. photodiodes) that are particularly diametrically arranged with respect to one another such that they can be used for differential sensing, so as to compensate for ambient conditions such as external lightening, humidity changes in the air, chemical changes (e.g. ion concentration) in the tear fluid.

Furthermore, in order to control adjustment of the focal power of the lens 1, the lens 1 particularly comprises a processing unit 190 (such a unit 190 may also be present in all other embodiments of the osmotic pumping lens 1) that is configured to control the electro-osmotic pumps 170, 270 depending on said control signal of the sensor assembly 80 and/or depending on a control signal in the form of a modulated power supply signal received by said power interface 185.

Preferably, as shown in FIGS. 43 and 44, the power interface 185, the sensor assembly 80, and the processing unit 190 are mounted to the ring member 30.

According to a specific embodiment, the power interface 185, the sensor assembly 80 and the processing unit 190 may be mounted on a carrier 186 that is preferably formed by a flexible printed circuit board (FPC), wherein the ring member 30 is also mounted on this carrier 186 or is formed by the carrier 186.

As shown in FIGS. 43 and 44, further (e.g. electrical) components of the lens 1 may be integrated on the carrier (e.g. FPC) 186 and/or may be arranged in a dedicated installation space EA1, EA2 on the base element 10 (e.g. in the channel(s) 177). Such components EC can be: one or several sensors 801, 802 of the sensor assembly 80, the whole sensor assembly 80, a power converter, a rectifier circuit, a voltage stabilization circuit, a battery charging circuit, a data storage device (e.g. EEPROM), circuitry for detection and control of timing for eyelid movement synchronized functions such as eyelid induced charging, eye lid assisted liquid pumping etc. Also functions like automatic standby mode or sleep mode with reduced power consumption (e.g. from maximal switching voltage down to minimum hold voltage), or malfunction detection (e.g. short circuits, empty battery) may be integrated onto said carrier.

Particularly, said carrier 186 may comprise one, two or several protruding regions 186a for carrying the above components EC, particularly individual sensors 801, 802.

Such a protruding region, which is also denoted as wing herein, is shown in FIG. 44 in detail. Here, said wing 186a protrudes from a section of the carrier 186 (e.g. FPC) that carries (or forms) the ring member 30 as well as carries the power interface 185. Such a wing 186a may comprise contact members 187 (e.g. solder pads or press contacts) for electrically connecting the components EC on the wing 186a to the battery or osmotic membrane assembly 170. The wing 186a may be arranged in a channel 177 of the lens 1.

In case the carrier 186 comprises two such wings 186a, these wings 186a may be arranged in the opposing channels 177 of the embodiment shown in FIG. 43 when the carrier 186 is mounted to the base element 10, namely at the regions EA1, EA2. Alternatively, as shown in FIG. 43 instead of wings 186a with integrated contact members 187, also a discrete wiring using individual conductors W, W', W" may be used to wire the contacts 110a, 110b of the battery 110 to the components EC in the regions EA1, EA2 or to the pump 170.

Figure 45:
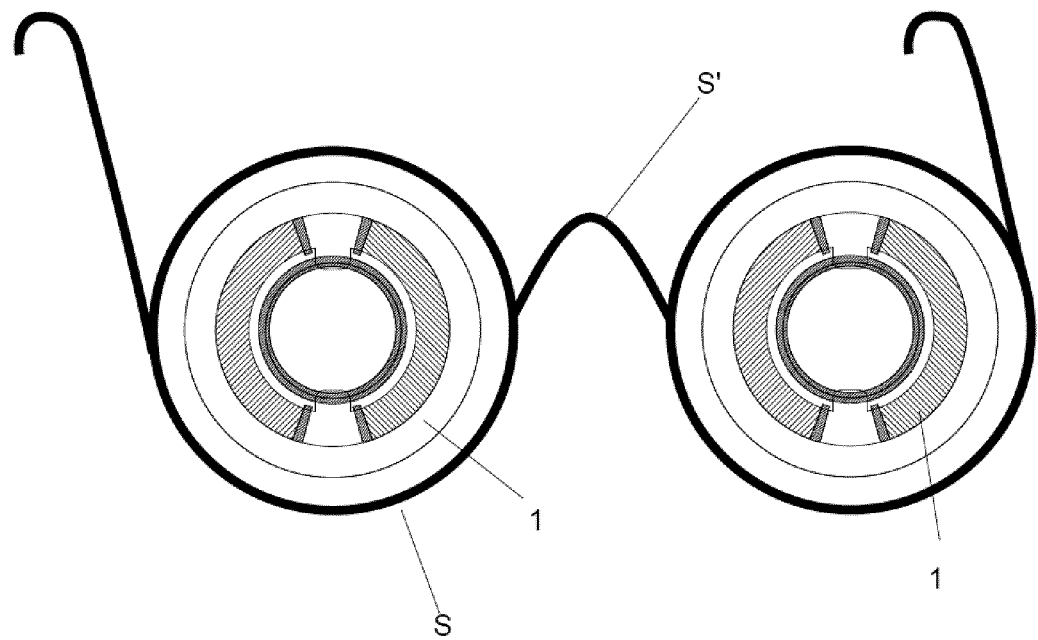
FIG. 45 schematically shows an embodiment of the present invention in the form of spectacles which comprise two lenses according to the invention, one for each eye of a person that wears the spectacles, and FIG. 46 schematically shows a storage container with a lens according to the invention that is arranged in the storage container, wherein the storage container comprises an inductive coil for inductive charging of the battery of the lens via the power interface of the lens (wireless recharging of the lens battery).

FIG. 45 shows yet another aspect of the present invention, namely an optical device, here in the form of spectacles for vision correction, which spectacles comprise two lenses 1 according to the invention that may be held by a spectacle frame S'.

Figure 46:
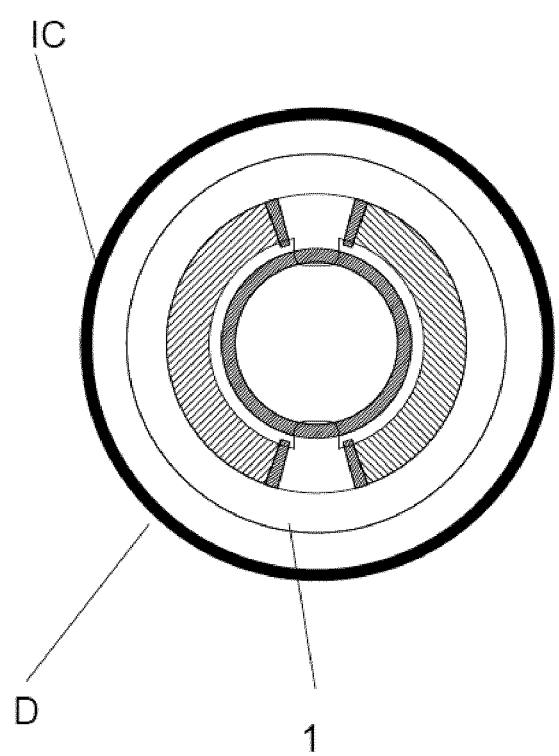

Further FIG. 46 shows an aspect of the present invention in the form of a storage container D with a lens 1 according to the invention that is arranged in the storage container D, wherein the storage container D comprises an inductive coil IC for inductive charging of the battery 110 of the lens 1 via the power interface 185 of the lens 1.

The use of the lens according to the invention is very versatile and further includes without limitation devices such as: vision systems, ophthalmic lenses (contact lenses and intraocular lenses), ophthalmology equipment such as phoropter, refractometer, fundus cameras, ppt. biometrie, perimeter, refractometer, tonometer, anomaloskop, kontrastometer, endothelmicroscope, anomaloscope, binoptometer, OCT, rodatest, ophthalmoscope, RTA, slitlamp microscope, surgical microscope, auto-refractometer, keratograph, confocal imager, Scheimpflug camera, wavefront aberrometer, pupillometer, skin laser, eye laser, otoscope, laryngoscope, Raman spectrometer, portable spectrometer, photodynamic diagnosis; as well as lighting devices, lighting fixtures, devices for machine vision, laser processing devices, devices for conducting a light show, printers, metrology devices, (e.g. head-worn) glasses, augmented reality or virtual reality displays, medical devices, robot cams, motion tracking devices, microscopes, telescopes, endoscopes, binoculars, surveillance cameras, automotive devices, projectors, range finder, bar code readers, and web cams, fiber coupling, biometric devices, electronic magnifiers, motion tracking, intraocular lenses, mobile phones, military, digital still cameras, web cams, microscopes, telescopes, endoscopes, binoculars, research, industrial applications.

While there are shown and described presently preferred embodiments of the invention, it is to be distinctly understood that the invention is not limited thereto but may be otherwise variously embodied and practiced within the scope of the following claims.

The invention claimed is:

1. A lens (1) for vision correction, wherein the lens (1) comprises:
   a transparent base element (10) having a back side (12), and a front side (11) facing away from the back side (12),
   a transparent and elastically expandable membrane (20) connected to said base element (10), wherein said membrane (20) comprises a back side (22) that faces said front side (11) of the base element (10),
   a ring member (30) connected to said the membrane (20) so that the ring member (30) defines a curvature-adjustable area (23) of the membrane (20), and
   wherein the lens (1) comprises a lens volume (41) adjacent said curvature-adjustable area (23) of the membrane (20), which lens volume (41) is delimited by the ring member (30), and wherein the lens (1) comprises a reservoir volume (42) arranged in a boundary region (24) of the lens (1), wherein said two volumes (41, 42) are each filled with a transparent liquid (50, 50a, 50b), and
   a pumping means (700) configured to transfer transparent liquid (50) from the reservoir volume (42) to the lens volume (41) or vice versa such that the curvature of said curvature-adjustable area (23) of the membrane (20) changes and the focal length of the lens (1) changes, characterized in that
   the pumping means (700) comprises or is formed as at least a first electro-osmotic pump (170), which first electro-osmotic pump comprises a porous membrane (173), a first electrode (171), and a second electrode (172), wherein the porous membrane (173) is arranged between said electrodes (171, 172) respectively.

2. The lens according to claim 1, characterized in that the lens (1) further comprises a protecting means (31; 75; 33; 34) that is configured to reduce or prevent an effect of an eyelid of the user on said focal length when said eyelid rests on said boundary region (24) of the lens (1).

3. The lens according to claim 2, characterized in that said protecting means (31; 75; 33; 34) is a rigid support structure (31) that is configured to reduce or prevent compression of the reservoir volume (42) when an eyelid of the user rests on said boundary region (24) of the lens.

4. Lens according to claim 3, characterized in that said support structure (31) comprises a plurality of ridges (32).

5. Lens according to claim 4, characterized in that said ridges (32) divide the reservoir volume (42) into a plurality of separate sectors (420), wherein each sector (420) is arranged between two neighboring ridges (32).

6. Lens according to one of the claim 3, characterized in that said support structure (31) comprises a rigid top (34) covering the reservoir volume (42) at least in sections from above and a rigid bottom (33) covering the reservoir volume (42) at least in sections form below.

7. The lens according to claim 2, characterized in that said protecting means of the lens (1) comprises at least one valve (75) for closing and opening a flow connection between the reservoir volume (42) and the lens volume (41).

8. The lens according to claim 2, characterized in that the lens (1) comprises at least one reservoir channel (422) forming part of the reservoir volume (42), via which reservoir channel (422) the reservoir volume (42) can be fluidly connected to the lens volume (41).

9. The lens according to claim 8, characterized in that the pumping means (700) comprises a ring-shaped actuator element (701), preferably in the form of a Piezo element (701), which is configured to be actuated such that liquid residing in the reservoir volume (42) is pressed into the lens volume (41), wherein said actuator element (701) is configured to expand outwards in a radial direction (R) running perpendicular an optical axis (z) of the lens (1) when being actuated, such that said actuator element (701) compresses a circumferential reservoir section (421) of the reservoir volume (42), which circumferential reservoir section (421) is fluidly connected to the lens volume (41) via the at least one reservoir channel (422), so as to push liquid from the reservoir volume (42) into the lens volume (41).

10. The lens according to claim 8, characterized in that the actuator elements (701) are arranged along the at least one reservoir channel (422) and are configured to bend towards the at least one reservoir channel (422) when being actuated so as to compress the at least one reservoir channel (422) upon bending of the respective actuator element (701) such that liquid (50) is pushed from the reservoir volume (42) into the lens volume (41).

11. The lens according to claim 8, characterized in that reservoir volume (42) comprises at least one chamber (426) that is connected via the at least one reservoir channel (422) to the lens volume (41), wherein the pumping means (700) comprises at least one actuator element (701), preferably in the form of a Piezo element (701), which is configured to bend towards the chamber (426) when being actuated so as to compress the chamber (42) upon bending of the respective actuator element (701) such that liquid (50) is pushed from the chamber (424) into the lens volume (41).

12. The lens according to claim 2, characterized in that the pumping means (700) comprises a plurality of actuator elements (701), preferably in the form of Piezo elements (701), which are configured to be actuated such that liquid (50) residing in the reservoir volume (42) is pressed into the lens volume (41) or vice versa.

13. The lens according to claim 12, characterized in that the actuator elements (701) are arranged along the at least one reservoir channel (422) and are configured to press against a deformable wall (423) of the at least one reservoir channel (422) so as to push liquid (50) from the reservoir volume (42) into the lens volume (41).

14. The lens according to claim 12, characterized in that the actuator elements (701) are formed as ring-shaped Piezo elements which are coaxially arranged with respect to the optical axis (z) of the lens (1), wherein the Piezo elements are arranged radially further out than an outermost edge of the lens volume.

15. The lens according to claim 14, characterized in that said actuator elements (701) are configured to expand in an axial direction coinciding with said optical axis (z) when being actuated, such that said actuator elements (701) press against a deformable wall (423) of the at least one reservoir channel (422) so as to push liquid from the reservoir volume (42) into the lens volume (41).

16. The lens according to claim 14, characterized in that said actuator elements (701) are configured to expand in a radial direction (R) running perpendicular to said optical axis (z) when being actuated, such that said actuator elements (701) deform a deformable wall (423) of the at least one reservoir channel (422) so as to push liquid from the reservoir volume (42) into the lens volume (41).

17. Lens according to claim 1, characterized in that the pumping means (700) comprises an actuator means (70) that is configured to press liquid (50) from the reservoir volume (42) into the lens volume (41) or vice versa.

18. Lens according to claim 17, characterized in that the actuator means (70) is configured to compress at least one of said sectors (420), a selection of said sectors (420), or all of said sectors (420), so as to transfer liquid (50) from the respective sector (420) into the lens volume (41).

19. Lens according to claim 17, characterized in that the actuator means (70) is configured to compress the individual sector (420) continuously so as to adjust said focal length in a continuous fashion, or that the actuator means (70) is configured to compress the individual sector (420) at once so as to adjust said focal length in a discrete manner.

20. The lens according to claim 17, characterized in that the actuator means (70) comprises a plurality of first electrodes (71) each being attached to an associated first wall (200) and a corresponding number of second electrodes (72) each being attached to an associated second wall (100) such that pairs of first and second electrodes (71, 72) are formed in each sector (420), wherein each pair of electrodes (71, 72) delimits an associated gap (74) arranged between the respective first and second electrode (71, 72) in the respective sector (420), which associated gap (74) is closable by means of a voltage applied to the respective pair of electrodes such that, when the respective gap (74) is closed, liquid (50) is pressed from the respective sector (420) into the lens volume (41), and wherein, when the voltage applied to the respective pair of electrodes (71, 72) is decreased or turned off, the respective gap (74) opens and a tension of the membrane (20) causes a corresponding amount of liquid (50) to flow back from the lens volume (41) into the respective sector (420) of the reservoir volume (42).

21. Lens according to claim 1, characterized in that said sectors (420) are each delimited by a first wall (200) and a second wall (100) that faces the associated first wall (200), wherein the first walls (200) are preferably formed by the membrane (20), and wherein the second walls (100) are preferably formed by the base element (10) or by the support structure (31).

22. The lens according to claim 1, characterized in that the transparent liquid residing in the lens volume (41) is a hydrophobic liquid (50a), and wherein the liquid residing in the reservoir volume (42) is a hydrophilic liquid (50b) such that in each sector (420) an interface (50c) is formed between the hydrophilic liquid (50a) and the hydrophobic liquid (50b), wherein the pumping means (700) is configured to apply a voltage between the hydrophilic liquid (50b) residing in the respective sector (420) and a surrounding electrode (425a) embedded in a wall (425) enclosing the respective sector (420), wherein said electrode (425a) is electrically insulated towards the hydrophilic liquid (50b), such that the respective interface (50c) is moved towards the lens volume (41) thus pushing hydrophobic liquid (50a) into the lens volume (41) such that the curvature of said curvature-adjustable area (23) of the membrane (20) increases and the focal length of the lens decreases, wherein when said voltage is decreased or turned off, a tension of the membrane (20) causes a corresponding amount of hydrophobic liquid (50a) to flow back from the lens volume (41) into the reservoir volume (42).

23. The lens according to claim 22, characterized in that the sectors (420) are in flow connection with each other by means of a circumferential reservoir section (421) formed by the reservoir volume (42), wherein said reservoir section (421) comprises a meandering shape at least in sections.

24. The lens according to claim 1, characterized in that the lens (1) comprises a sensor means (80), a processing unit (90), a battery (110), and an actuator (70).

25. The lens according to claim 1, characterized in that the lens (1) comprises a sensor means (80) configured to sense a signal, preferably in the form of a movement of the person wearing the lens (1), and to provide an output signal in response to said signal, wherein particularly said movement is a movement of one of: a crystalline lens, an eyelid (4), or of an eye (2) of said person.

26. The lens according to claim 25, characterized in that the lens (1) further comprises a processing unit (90) that is configured to control the pumping means (700) and/or said at least one valve (75), so as to transfer liquid (50) from the reservoir volume into the lens volume or vice versa in response to the output signal provided by the sensor (80) or in response to an output signal provided by an external device (81).

27. The lens according to claim 1, characterized in that the ring member (30) includes one or multiple channels (60) which fluidly connect the reservoir volume (42) and the lens volume (41).

28. The lens according to claim 1, characterized in that the first and/or the second electrode comprise or are formed out of one of the following materials: carbon nanotubes, carbon black, carbon grease, conducting greases, metal ions, liquid metals, metallic powders, in particular metallic nanoparticles, metal films, or conducting polymers.

29. The lens according to claim 1, characterized in that an anti-stiction coating or layer is provided on at least one of: the first wall, the second wall, the first electrodes, the second electrodes.

30. Lens according to claim 1, characterized in that said first electro-osmotic pump (170) separates (170) an upper compartment (174) of the reservoir volume (42) from a lower compartment (175) of the reservoir volume (42), which compartments (174, 175) are arranged on top of one another, wherein the upper compartment (174) is arranged between said first electro-osmotic pump (170) and said membrane (20); or that said porous membrane (173) separates (170) an upper compartment (174) of the reservoir volume (42) from a lower compartment (175) of the reservoir volume (42), which compartments (174, 175) are arranged on top of one another, wherein the upper compartment (174) is arranged between said porous membrane (173) and said membrane (20).

31. Lens according to claim 30, characterized in that said first electro-osmotic pump (170) is configured to pump liquid (50) from the upper compartment (174) into the lower compartment (175) or from the lower compartment (175) to the upper compartment (174) depending on a voltage applied to said electrodes (171, 172) so as to transfer liquid (50) between the lens volume (41) and the reservoir volume (42).

32. Lens according to claim 30, characterized in that the lower compartment (175) or the upper compartment (174) is connected to the lens volume (41) via at least one channel (177).

33. The lens according to claim 30, characterized in that the lens (1) comprises a further ring member (300) surrounding the upper compartment (174), wherein said first electro-osmotic pump (170) is connected to a lower face side (30c) of the ring member (30) and/or to a lower face side (300c) of the further ring member (300).

34. The lens according to claim 30, characterized in that the lens (1) comprises a support structure (182) arranged in the lower compartment (175) for supporting said first electro-osmotic pump (170) or said porous membrane (173), and/or a support structure (181) arranged in the upper compartment (174) for supporting said first electro-osmotic pump (170) or said porous membrane (173).

35. The lens according to claim 30, characterized in that the base element (10) comprises a recess (10a), wherein said lower compartment (175) is arranged in said recess (10a), wherein particularly said recess (10a) is a curved and/or circumferential recess (10a).

36. The lens according to claim 35, characterized in that the recess (10a) comprises two opposing steps (10b) for aligning said first electro-osmotic pump (170) with respect to the recess (10a).

37. Lens according to claim 1, characterized in that said first electro-osmotic pump (170) is arranged adjacent a lateral surface (30a) of the ring member (30), which lateral surface (30a) connects an upper face side (30b) of the ring member (30), via which upper face side (30b) the ring member (30) is connected to the membrane (20), to a lower face side (30c) of the ring member (30), which lower face side (30c) faces away from said upper face side (30b).

38. Lens according to claim 1, characterized in that said first electro-osmotic pump (170) is connected to a lower face side (30c) of the ring member (30), which lower face side (30c) faces away from an upper face side (30b) of the ring member (30), via which upper face side (30b) the ring member (30) is connected to said membrane (20).

39. The lens according to claim 1, characterized in that said first electro-osmotic pump (170) comprises a first contact lead (171a) for connecting a battery (110) to the first electrode (171), and a second contact lead (172a) for connecting said battery (110) to the second electrode (172).

40. The lens according to claim 1, characterized in that the first electro-osmotic pump (170) comprises a curved shape.

41. The lens according to claim 1, characterized in that the base element (10) comprises a circumferential step (10c) for aligning the ring member (30) with respect to the base element (10).

42. The lens according to claim 1, characterized in that the lens comprises a battery (110).

43. The lens according to claim 42, characterized in that the battery (110) is arranged outside the lower and upper compartments (174, 175), or that the battery (110) is arranged in the lower compartment (175).

44. The lens according to claim 42, characterized in that the lens (1) comprises a power interface (185) configured for inductive charging of the battery (110).

45. The lens according to claim 44, characterized in that the lens (1) comprises a processing unit (190) configured to control the first electro-osmotic pump (170) depending on said control signal of a sensor assembly (80) and/or depending on a control signal in the form of a modulated power supply signal received by said power interface (185).

46. The lens according to claim 44, characterized in that the power interface (185), a sensor assembly (80), and a processing unit (190) are mounted to the ring member (30).

47. The lens according to claim 44, characterized in that the power interface (185), a sensor assembly (80) and a processing unit (190) are mounted on a carrier (186), wherein the ring member (30) is also mounted on the carrier (186) or is formed by the carrier (186).

48. The lens according to claim 1, characterized in that the lens (1) comprises a sensor assembly (80) configured to detect one of: an eye lid movement, a fully closed eyelid, a partially closed eye lid and to generate a corresponding control signal.

49. The lens according to claim 1, characterized in that the lens (1) comprises a second electro-osmotic pump (270), which second electro-osmotic pump (270) comprises a porous membrane (273), a first electrode (271), and a second electrode (272), wherein the porous membrane (273) of the second electro-osmotic pump (270) is arranged between said electrodes (271, 272) of the second electro-osmotic pump (270) respectively.

50. Lens according to claim 49, characterized in that said second electro-osmotic pump (270) separates a further upper compartment (274) of the reservoir volume (42) from a further lower compartment (275) of the reservoir volume (42), which further compartments (274, 275) are arranged on top of one another, wherein the further upper compartment (274) is arranged between said second electro-osmotic pump (270) and said membrane (20); or that said porous membrane (273) of the second electro-osmotic pump (270) separates a further upper compartment (274) of the reservoir volume (42) from a further lower compartment (275) of the reservoir volume (42), which further compartments (274, 275) are arranged on top of one another, wherein the further upper compartment (274) is arranged between said porous membrane (273) and said membrane (20).

51. Lens according to claim 50, characterized in that said second electro-osmotic pump (270) is configured to pump liquid (50) from the further upper compartment (274) into the further lower compartment (275), or from the further lower compartment (275) to the further upper compartment (274) depending on a voltage applied to said electrodes (271, 272) of the second electro-osmotic pump (270), so as to transfer liquid (50) between the lens volume (41) and the reservoir volume (42).

52. Lens according to claim 50, characterized in that the lens (1) comprises two opposing channels (177), wherein the lower compartments (175, 275) or the upper compartments (174, 274) of the two electro-osmotic pumps (170, 270) are in fluid communication with the lens volume (41) via both channels (177).

53. Lens according to claim 52, characterized in that the lens (1) comprises a support structure (183*a*, 183*b*) arranged in each channel (177) for supporting the ring member (30) and/or said membrane (20).

54. Lens according to claim 1, characterized in that the lens (1) is configured to be one of:
   placed directly on the surface of an eye (2) of a person,
   placed inside an eye (2) of a person,
   placed in front of an eye (2) of a person, particularly spaced apart from said eye (2).

55. Optical assembly, comprising: a lens (1) according to claim 1, and a transparent enclosure, wherein said lens (1) is arranged or embedded in said enclosure, and wherein preferably said enclosure forms or comprises a further lens.

\* \* \* \* \*